US012799147B2

(12) United States Patent
Kelleher et al.

(10) Patent No.: US 12,799,147 B2
(45) Date of Patent: Nov. 17, 2026

(54) RIBONUCLEIC ACID PURIFICATION

(71) Applicant: ModernaTX, Inc., Cambridge, MA (US)

(72) Inventors: Bill Kelleher, Cambridge, MA (US); Michael Shamashkin, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 764 days.

(21) Appl. No.: 18/036,992

(22) PCT Filed: Nov. 18, 2021

(86) PCT No.: PCT/US2021/059944
§ 371 (c)(1),
(2) Date: May 15, 2023

(87) PCT Pub. No.: WO2022/109171
PCT Pub. Date: May 27, 2022

(65) Prior Publication Data

US 2024/0025935 A1 Jan. 25, 2024

Related U.S. Application Data

(60) Provisional application No. 63/115,446, filed on Nov. 18, 2020.

(51) Int. Cl.
*C07H 1/06* (2006.01)
*C07H 21/02* (2006.01)

(52) U.S. Cl.
CPC ............... *C07H 1/06* (2013.01); *C07H 21/02* (2013.01)

(58) Field of Classification Search
CPC ...... C07H 15/1006; C07H 1/06; C07H 21/02; C12N 15/10006
See application file for complete search history.

(56) References Cited

U.S. PATENT DOCUMENTS

| | | | | | |
|---|---|---|---|---|---|
| 5,030,352 | A * | 7/1991 | Varady | B01J 20/3272 210/198.2 |
| 6,812,341 | B1 | 11/2004 | Conrad | |
| 10,533,045 | B2 | 1/2020 | Allison et al. | |
| 11,377,470 | B2 | 7/2022 | Issa et al. | |
| 11,845,772 | B2 | 12/2023 | Issa et al. | |
| 2006/0216816 | A1 | 9/2006 | Ohnishi | |
| 2013/0165539 | A1 | 6/2013 | Carbonell et al. | |
| 2016/0024140 | A1* | 1/2016 | Issa | C12Q 1/6806 536/25.41 |
| 2019/0358230 | A1* | 11/2019 | Gmachl | C07D 403/10 |
| 2020/0308569 | A1 | 10/2020 | Geldhof | |

OTHER PUBLICATIONS

Engel et al., "Purification of poly-dA oligonucleotides and mRNA-protein fusions with dT25-OAS resin," available in PMC Feb. 15, 2021, published in final edited form as: Bioorg Med Chem Lett. 30(4):126934 (Feb. 2020) (11 pages).

* cited by examiner

*Primary Examiner* — Jane J Zara
(74) *Attorney, Agent, or Firm* — Clark + Elbing LLP

(57) ABSTRACT

The present invention relates to compositions and methods for the purification of ribonucleic acids including a polyA tail. The compositions and methods include a polystyrene divinylbenzene particle, a linker, and a poly-deoxythymidine oligonucleotide.

13 Claims, 43 Drawing Sheets

Specification includes a Sequence Listing.

| Factors | Effect | P |
|---|---|---|
| dT/resin charge (mg/mL) | 0.123 | 0.152 |
| EP 450 resin slurry concentration (%) | 0.044 | 0.556 |
| Phosphate concentration in formulation solution (M) | 0.128 | 0.14 |
| pH in formulation solution | 0.033 | 0.663 |
| Coupling time (hours) | 0.134 | 0.112 |
| Coupling temperature (°C) | 0.212 | 0.029 |

| Factors | Effect | P |
|---|---|---|
| **dT/resin charge (mg/mL)** | 0.26658 | 0.207 |
| **EP 450 resin slurry concentration (%)** | 0.16568 | 0.388 |
| **Phosphate concentration in formulation solution (M)** | -0.171 | 0.394 |
| **pH in formulation solution** | 0.006 | 0.977 |
| **Coupling time (hours)** | 0.269 | 0.185 |
| **Coupling temperature (°C)** | 0.364 | 0.092 |

850 nt mRNA Langmuir model fit $$C_R = \frac{Q_m C_S}{K_d + C_S}$$

$$C_R = \frac{Q_m C_S}{K_d + C_S}$$

Lineweaver-Burk double-reciprocal equation:

$$\frac{1}{C_R} = \frac{K_d}{Q_m}\frac{1}{C_S} + \frac{1}{Q_m}$$

| | 850 nt mRNA | 4000 nt mRNA |
|---|---|---|
| 1/Qm | 0.14 | 0.21 |
| Qm, mg/mL | 7.13 | 4.87 |
| Kd/Qm | 0.03 | 0.07 |
| Kd, mg/mL | 0.23 | 0.36 |

FIG. 23

| Conjugates prepared and characterized in earlier Examples | | | | From Lineweaver-Burk plot | | | | From JMP Langmuir isotherm fit | | | | DBC (mg/mL) | |
|---|---|---|---|---|---|---|---|---|---|---|---|---|---|
| | | | | $Q_m$ (mg/mL) | | $K_d$ (mg/mL) | | $Q_m$ (mg/mL) | | $K_d$ (mg/mL) | | | |
| Sample No. | dT/resin charge (mg/mL) | Ionic Capacity (μmol/mL) | dA 40mer SBC, mg/ml | 850 nt nRNA | 4000 nt mRNA | 850 nt mRNA | 4000 nt mRNA | 850 nt mRNA | 4000 nt mRNA | 850 nt mRNA | 4000 nt mRNA | 850 nt mRNA | 4000 nt mRNA |
| 1 | 3.0 | 5.1 | 0.69 | 6.42 | 4.55 | 0.20 | 0.20 | 4.8 | 3.9 | 0.01 | 0.06 | 4.1 | 2.0 |
| 2 | 3.0 | 9.2 | 0.93 | 5.00 | 2.27 | 0.01 | 0.11 | 5.5 | 5.1 | 0.02 | 0.59 | | |
| 3 | 3.0 | 8.2 | 1.05 | 7.02 | 5.35 | 0.17 | 0.32 | 5.4 | 4.5 | 0.01 | 0.16 | 4.9 | 1.8 |
| 4 | 3.0 | 10.7 | 0.77 | 3.24 | 1.46 | 0.09 | 0.45 | 4.3 | 2.6 | 0.19 | 0.95 | | |
| 5 | 3.0 | 15 | 0.80 | 3.15 | 1.10 | 0.18 | 0.48 | 4.5 | | 0.39 | | | |
| 6 | 3.0 | 10.5 | 0.14 | | | | | | | | | | |
| 7 | 4.5 | 7.8 | 0.91 | 7.24 | 4.94 | 0.25 | 0.31 | 5.2 | 3.9 | 0.02 | 0.11 | | |
| 8 | 4.5 | 10.5 | 1.11 | 7.02 | 5.16 | 0.05 | 0.61 | 6.9 | 5.7 | 0.05 | 0.72 | | |
| 9 | 4.5 | 10.3 | 1.56 | 7.15 | 6.09 | 0.12 | 0.43 | 5.8 | 4.9 | 0.02 | 0.22 | | |
| 10 | 4.5 | 12 | 1.13 | 5.28 | 0.90 | 0.35 | 0.25 | 4.9 | 5.9 | 0.24 | 4.42 | | |
| 11 | 4.5 | 16.8 | 1.42 | 2.87 | 0.59 | 0.20 | 0.29 | 3.3 | | 0.25 | | | |
| 12 | 4.5 | 9.5 | 0.14 | | | | | | | | | | |
| 13 | 5.0 | 6.7 | 0.79 | 7.13 | 4.87 | 0.23 | 0.36 | 5.1 | 3.8 | 0.01 | 0.12 | | |
| 14 | 5.0 | 9.5 | 0.97 | 7.72 | 3.66 | 0.08 | 0.54 | 6.8 | 6.0 | 0.03 | 1.17 | 5.5 | 1.0 |

Target 3000 Å

Target 4000 Å

Target 5000 Å

RIBONUCLEIC ACID PURIFICATION

SEQUENCE LISTING

The instant application contains a Sequence Listing which has been submitted electronically in ASCII format and is hereby incorporated by reference in its entirety. Said ASCII copy, created on Nov. 18, 2021, is named 50858-115WO2_Sequence_Listing_11_18_21_ST25 and is 416 bytes in size.

FIELD OF THE INVENTION

The invention relates to the field of compositions and methods for the purification of RNA having a poly-adenosine (polyA) sequence.

BACKGROUND OF THE INVENTION

RNA purified from biological samples is utilized extensively in medical, molecular biology, and environmental fields, and there have been considerable achievements in the development of methods for RNA purification over the past three decades. However, commercially available RNA purification technologies are typically optimized for small scale (e.g., <1 mg) RNA isolations on a bench top from crude cell/tissue extracts or blood. Common surfaces utilized for small-scale RNA purification are cellulose, latex particles, and magnetic beads. Such compositions are not generally viable for large scale chromatographic processes designed for the cGMP (Current Good Manufacturing Practice) manufacture of therapeutic mRNAs. In particular, cellulose-based surfaces often produce leached ligand, contain fine particulates, and have poor flow properties for column chromatography. In terms of RNA quality and purity, cellulose surfaces have been shown to yield eluted RNA with substantial contamination, for example, contamination from endotoxins. Furthermore, RNA generated using these commercially available surfaces typically must be processed with additional separation methods to ensure RNA quality for clinical and therapeutic use. Endotoxin contamination in particular has become a critical issue in biomanufacturing because the presence of endotoxins in therapeutic biomolecules, e.g., mRNA, is detrimental to patient safety.

Hence, there remains a need for large-scale RNA purification methods that eliminate contaminants.

SUMMARY OF THE INVENTION

The present invention features compositions and methods for the purification of RNA (e.g., mRNA) including a polystyrene divinylbenzene particle and thymine oligomers (e.g., poly-deoxythymidine oligonucleotides).

In an aspect, the disclosure features a composition containing a plurality of conjugates including the structure of Formula I:

A-L-B    Formula I, wherein:

A is a surface containing a polystyrene divinylbenzene (PSDVB) particle;

L is a linker including the structure:

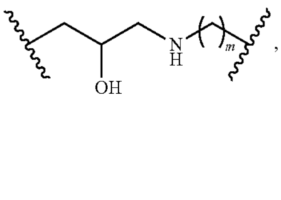, m is 1, 2, 3, 4, 5, 6, 7, 8, 9, or 10; and

B is an oligomer containing a poly-deoxythymidine oligonucleotide;

wherein the plurality of conjugates:

(i) has an epoxide density of from about 30 to about 60 μmol/mL;

(ii) has a poly-deoxythymidine oligonucleotide density of from about 0.1 to about 0.5 μmol/mL;

(iii) has a dT/resin charge of less than about 5 mg/mL;

(iv) has an ionic capacity of greater than about 5 μmol/mL; and/or (v) has a dynamic binding capacity of greater than about 1.5 μmol/mL.

In some embodiments, the plurality of conjugates has an epoxide density of 30 to 60 μmol/mL (e.g., 30 μmol/mL, 31 μmol/mL, 32 μmol/mL, 33 μmol/mL, 34 μmol/mL, 35 μmol/mL, 36 μmol/mL, 37 μmol/mL, 38 μmol/mL, 39 μmol/mL, 40 μmol/mL, 41 μmol/mL, 42 μmol/mL, 43 μmol/mL, 44 μmol/mL, 45 μmol/mL, 46 μmol/mL, 47 μmol/mL, 48 μmol/mL, 49 μmol/mL, 50 μmol/mL, 51 μmol/mL, 52 μmol/mL, 53 μmol/mL, 54 μmol/mL, 55 μmol/mL, 56 μmol/mL, 57 μmol/mL, 58 μmol/mL, 59 μmol/mL, or 60 μmol/mL).

In some embodiments, the plurality of conjugates has an epoxide density of 40 to 60 μmol/mL (e.g., 40 μmol/mL, 41 μmol/mL, 42 μmol/mL, 43 μmol/mL, 44 μmol/mL, 45 μmol/mL, 46 μmol/mL, 47 μmol/mL, 48 μmol/mL, 49 μmol/mL, 50 μmol/mL, 51 μmol/mL, 52 μmol/mL, 53 μmol/mL, 54 μmol/mL, 55 μmol/mL, 56 μmol/mL, 57 μmol/mL, 58 μmol/mL, 59 μmol/mL, or 60 μmol/mL).

In some embodiments, the plurality of conjugates has a poly-deoxythymidine oligonucleotide density of 0.1 to 0.5 μmol/mL (e.g., 0.1 μmol/mL, 0.2 μmol/mL 0.3 μmol/mL 0.4 μmol/mL, or 0.5 μmol/mL).

In some embodiments, the plurality of conjugates has a poly-deoxythymidine oligonucleotide density of about 0.3 μmol/mL.

In some embodiments, the plurality of conjugates has a dT/resin charge of less than 5 mg/mL (e.g., 1 mg/mL, 2 mg/mL, 3, mg/mL, or 4 mg/mL). In some embodiments, the plurality of conjugates has a dT/resin charge of about 3 mg/mL.

In some embodiments, the plurality of conjugates has an ionic capacity of greater than 5 μmol/mL. In some embodiments, the plurality of conjugates has an ionic capacity of 5 to 10 μmol/mL (e.g., 5 μmol/mL, 6 μmol/mL, 7 μmol/mL, 8 μmol/mL, 9 μmol/mL, or 10 μmol/mL).

In some embodiments, the plurality of conjugates has a dynamic binding capacity of greater than 1.5 μmol/mL (e.g., 1.5 to 5 μmol/mL, such as 1.5 μmol/mL, 2 μmol/mL, 2.5 μmol/mL, 3, μmol/mL, 3.5 μmol/mL, 4 μmol/mL, 4.5 μmol/mL, or 5 μmol/mL).

In an aspect, the disclosure features a composition including a plurality of conjugates including the structure of Formula I:

A-L-B    Formula I, where:

A is a polystyrene divinylbenzene particle;

L is a linker including the structure:

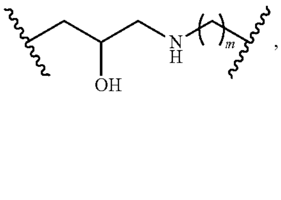, where m is 1, 2, 3, 4, 5, 6, 7, 8, 9, or 10; and

B includes a poly-deoxythymidine oligonucleotide.

In an aspect, the disclosure features a composition including a plurality of conjugates including the structure of Formula I:

A-L-B Formula I, where:

A is a polystyrene divinylbenzene particle;

L is a linker including the structure:

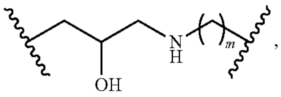, where m is 1, 2, 3, 4, 5, 6, 7, 8, 9, or 10; and

B includes a poly-deoxythymidine oligonucleotide, where the plurality of conjugates has a mean particle size of 40 to 60 μm.

In an aspect, the disclosure features a composition including a plurality of conjugates including the structure of Formula I:

A-L-B Formula I where:

A is a polystyrene divinylbenzene particle;

L is a linker including the structure:

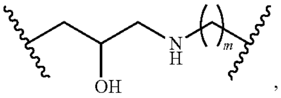, where m is 1, 2, 3, 4, 5, 6, 7, 8, 9, or 10; and

B includes a poly-deoxythymidine oligonucleotide, where the plurality of conjugates has a mean pore size of greater than 1000 Å.

In an aspect, the disclosure features a composition including a plurality of conjugates including the structure of Formula I:

A-L-B Formula I where:

A is a polystyrene divinylbenzene particle;

L is a linker including the structure:

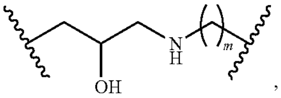, where m is 1, 2, 3, 4, 5, 6, 7, 8, 9, or 10; and

B includes a poly-deoxythymidine oligonucleotide, where the plurality of conjugates has an ionic capacity of greater than 5 μmol/mL.

In some embodiments, m is 2, 3, 4, 5, or 6. In particular embodiments, m is 6.

In some embodiments, L includes the structure:

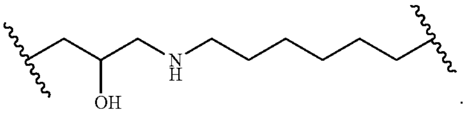 [SMILES: *CCCCCCNCC(O)C*].

In some embodiments, the poly-deoxythymidine oligonucleotide includes from 5 to 200 (e.g., 5 to 20, 5 to 50, 5 to 100, 10 to 30, 15 to 25, 20 to 40, 20 to 100, 20 to 200, 100 to 200, or 150 to 200) deoxythymidines. In some embodiments, the poly-deoxythymidine oligonucleotide includes 20 to 40 deoxythymidines (e.g., 20, 21, 22, 23, 24, 25, 26, 27, 28, 29, 30, 31, 32, 33, 34, 35, 36, 37, 38, 39, or 40 deoxythymidines). In some embodiments, the poly-deoxythymidine oligonucleotide includes 20 deoxythymidines. In some embodiments, the poly-deoxythymidine oligonucleotide consists of 20 deoxythymidines.

In some embodiments, the polystyrene divinylbenzene particle is an epoxide-functionalized polystyrene divinylbenzene particle.

In some embodiments, the plurality of conjugates has an epoxide density of from 30 to 60 μmol/mL (e.g., 30 to 40 μmol/mL, 40 to 50 μmol/mL, 50 to 60 μmol/mL, or 40 to 60 μmol/mL). In some embodiments, the plurality of conjugates has an epoxide density of 30 μmol/mL. In some embodiments, the plurality of conjugates has an epoxide density of 40 to 60 μmol/mL.

In some embodiments, the plurality of conjugates has an epoxide density of about 30 μmol/mL (e.g., an epoxide density of 30 μmol/mL). In some embodiments, the plurality of conjugates has an epoxide density of about 31 μmol/mL (e.g., an epoxide density of 31 μmol/mL). In some embodiments, the plurality of conjugates has an epoxide density of about 32 μmol/mL (e.g., an epoxide density of 32 μmol/mL). In some embodiments, the plurality of conjugates has an epoxide density of about 33 μmol/mL (e.g., an epoxide density of 33 μmol/mL). In some embodiments, the plurality of conjugates has an epoxide density of about 34 μmol/mL (e.g., an epoxide density of 34 μmol/mL). In some embodiments, the plurality of conjugates has an epoxide density of about 35 μmol/mL (e.g., an epoxide density of 35 μmol/mL). In some embodiments, the plurality of conjugates has an epoxide density of about 36 μmol/mL (e.g., an epoxide density of 36 μmol/mL). In some embodiments, the plurality of conjugates has an epoxide density of about 37 μmol/mL (e.g., an epoxide density of 37 μmol/mL). In some embodiments, the plurality of conjugates has an epoxide density of about 38 μmol/mL (e.g., an epoxide density of 38 μmol/mL). In some embodiments, the plurality of conjugates has an epoxide density of about 39 μmol/mL (e.g., an epoxide density of 39 μmol/mL). In some embodiments, the plurality of conjugates has an epoxide density of about 40 μmol/mL (e.g., an epoxide density of 40 μmol/mL). In some embodiments, the plurality of conjugates has an epoxide density of about 41 μmol/mL (e.g., an epoxide density of 41 μmol/mL). In some embodiments, the plurality of conjugates has an epoxide density of about 42 μmol/mL (e.g., an epoxide density of 42 μmol/mL). In some embodiments, the plurality of conjugates has an epoxide density of about 43 μmol/mL (e.g., an epoxide density of 43 μmol/mL). In some embodiments, the plurality of conjugates has an epoxide density of about 44 μmol/mL (e.g., an epoxide density of 44 μmol/mL). In some embodiments, the plurality of conjugates has an epoxide density of about 45 μmol/mL (e.g., an epoxide density of 45 μmol/mL). In some embodiments, the plurality of conjugates has an epoxide density of about 46 μmol/mL (e.g., an epoxide density of 46 μmol/mL). In some embodiments, the plurality of conjugates has an epoxide density of about 47 μmol/mL (e.g., an epoxide density of 47 μmol/mL). In some embodiments, the plurality of conjugates has an epoxide density of about 48 μmol/mL (e.g., an epoxide density of 48 μmol/mL). In some embodiments, the plurality of conjugates has an epoxide density of about 49 μmol/mL (e.g., an epoxide density of 49 μmol/mL). In some embodiments, the plurality of conjugates has an epoxide density of about 50 μmol/mL (e.g., an epoxide density of 50 μmol/mL). In some embodiments, the plurality of conjugates has an epoxide density of about 51 μmol/mL (e.g., an epoxide density of 51 μmol/mL). In some embodiments, the plurality of conjugates has an epoxide density of about 52 μmol/mL (e.g., an epoxide density of 52 μmol/mL). In some embodiments, the plurality of conjugates has an epoxide density of about 53 μmol/mL (e.g., an epoxide density of 53 μmol/mL). In some embodiments, the plurality of conjugates has an epoxide density of about 54 μmol/mL (e.g., an epoxide density of 54 μmol/mL). In some embodiments, the plurality of conjugates has an epoxide density of about 55 μmol/mL (e.g., an epoxide density of 55 μmol/mL). In some embodiments, the plurality of conjugates has an epoxide density of about 56 μmol/mL (e.g., an epoxide density of 56 μmol/mL). In some embodiments, the plurality of conjugates has an epoxide density of about 57 μmol/mL (e.g., an epoxide density of 57 μmol/mL). In some embodiments, the plurality of conjugates has an epoxide density of about 58 μmol/mL (e.g., an epoxide density of 58 μmol/mL). In some embodiments, the plurality of conjugates has an epoxide density of about 59 μmol/mL (e.g., an epoxide density of 59 μmol/mL). In some embodiments, the plurality of conjugates has an epoxide density of about 60 μmol/mL (e.g., an epoxide density of 60 μmol/mL).

In some embodiments, the plurality of conjugates has a poly-deoxythymidine oligonucleotide density of from 0.1 to 0.5 μmol/mL (e.g., 0.1 to 0.3 μmol/mL, 0.2 to 0.4 μmol/mL, or 0.3 to 0.5 μmol/mL). In some embodiments, the plurality of conjugates has a poly-deoxythymidine oligonucleotide density of about 0.1 μmol/mL (e.g., a poly-deoxythymidine oligonucleotide density of 0.1 μmol/mL). In some embodiments, the plurality of conjugates has a poly-deoxythymidine oligonucleotide density of about 0.2 μmol/mL (e.g., a poly-deoxythymidine oligonucleotide density of 0.2 μmol/mL). In some embodiments, the plurality of conjugates has a poly-deoxythymidine oligonucleotide density of about 0.3 μmol/mL (e.g., a poly-deoxythymidine oligonucleotide density of 0.3 μmol/mL). In some embodiments, the plurality of conjugates has a poly-deoxythymidine oligonucleotide density of about 0.4 μmol/mL (e.g., a poly-deoxythymidine oligonucleotide density of 0.4 μmol/mL). In some embodiments, the plurality of conjugates has a poly-deoxythymidine oligonucleotide density of about 0.5 μmol/mL (e.g., a poly-deoxythymidine oligonucleotide density of 0.5 μmol/mL).

In some embodiments, the plurality of conjugates has a mean particle size of from 40 to 60 μm (e.g., 40 to 50 μm, 50 to 60 μm, or 45 to 55 μm). In some embodiments, the plurality of conjugates has a mean particle size of about 40 μm (e.g., a mean particle size of 40 μm). In some embodiments, the plurality of conjugates has a mean particle size of about 41 μm (e.g., a mean particle size of 41 μm). In some embodiments, the plurality of conjugates has a mean particle size of about 42 μm (e.g., a mean particle size of 42 μm). In some embodiments, the plurality of conjugates has a mean particle size of about 43 μm (e.g., a mean particle size of 43 μm). In some embodiments, the plurality of conjugates has a mean particle size of about 44 μm (e.g., a mean particle size of 44 μm). In some embodiments, the plurality of conjugates has a mean particle size of about 45 (e.g., a mean particle size of 45 μm). In some embodiments, the plurality of conjugates has a mean particle size of about 46 μm (e.g., a mean particle size of 46 μm). In some embodiments, the plurality of conjugates has a mean particle size of about 47 μm (e.g., a mean particle size of 47 μm). In some embodiments, the plurality of conjugates has a mean particle size of about 48 μm (e.g., a mean particle size of 48 μm). In some embodiments, the plurality of conjugates has a mean particle size of about 49 μm (e.g., a mean particle size of 49 μm). In some embodiments, the plurality of conjugates has a mean particle size of about 50 μm (e.g., a mean particle size of 50 μm). In some embodiments, the plurality of conjugates has a mean particle size of about 51 μm (e.g., a mean particle size of 51 μm). In some embodiments, the plurality of conjugates has a mean particle size of about 52 μm (e.g., a mean particle size of 52 μm). In some embodiments, the plurality of conjugates has a mean particle size of about 53 μm (e.g., a mean particle size of 53 μm). In some embodiments, the plurality of conjugates has a mean particle size of about 54 μm (e.g., a mean particle size of 54 μm). In some embodiments, the plurality of conjugates has a mean particle size of about 55 μm (e.g., a mean particle size of 55 μm). In some embodiments, the plurality of conjugates has a mean particle size of about 56 μm (e.g., a mean particle size of 56 μm). In some embodiments, the plurality of conjugates has a mean particle size of about 57 μm (e.g., a mean particle size of 57 μm). In some embodiments, the plurality of conjugates has a mean particle size of about 58 μm (e.g., a mean particle size of 58 μm). In some embodiments, the plurality of conjugates has a mean particle size of about 59 μm (e.g., a mean particle size of 59 μm). In some embodiments, the plurality of conjugates has a mean particle size of about 60 μm (e.g., a mean particle size of 60 μm).

In particular embodiments, the plurality of conjugates has a mean particle size of about 50 μm (e.g., a mean particle size of 50 μm).

In some embodiments, less than 10% (e.g., less than 9%, less than 8%, less than 7%, less than 6%, less than 5%, less than 4%, less than 3%, less than 2%, or less than 1%) of the plurality of conjugates have a particle size of less than 20 μm.

In some embodiments, the plurality of conjugates has a mean pore size of greater than 1000 Å (e.g., greater than 2000 Å, greater than 3000 Å, greater than 4000 Å, greater than 5000 Å, or greater than 10,000 Å).

In some embodiments, the plurality of conjugates has a mean pore size of from 1000 to 4000 Å (e.g., 1000 to 2000 Å, 2000 to 3000 Å, 3000 to 4000 Å, 1000 to 3000 Å, or 2000 to 4000 Å). In some embodiments, the plurality of conjugates has a mean pore size of about 1000 Å. In some embodiments, the plurality of conjugates has a mean pore size of about 1100 Å. In some embodiments, the plurality of conjugates has a mean pore size of about 1200 Å. In some embodiments, the plurality of conjugates has a mean pore size of about 1300 Å. In some embodiments, the plurality of conjugates has a mean pore size of about 1400 Å. In some embodiments, the plurality of conjugates has a mean pore size of about 1500 Å. In some embodiments, the plurality of conjugates has a mean pore size of about 1600 Å. In some embodiments, the plurality of conjugates has a mean pore size of about 1700 Å. In some embodiments, the plurality of conjugates has a mean pore size of about 1800 Å. In some embodiments, the plurality of conjugates has a mean pore size of about 1900 Å. In some embodiments, the plurality of conjugates has a mean pore size of about 2000 Å. In some embodiments, the plurality of conjugates has a mean pore size of about 2100 Å. In some embodiments, the plurality of conjugates has a mean pore size of about 2200 Å. In some embodiments, the plurality of conjugates has a mean pore size of about 2300 Å. In some embodiments, the plurality of conjugates has a mean pore size of about 2400 Å. In some embodiments, the plurality of conjugates has a mean pore size of about 2500 Å. In some embodiments, the plurality of conjugates has a mean pore size of about 2600 Å. In some embodiments, the plurality of conjugates has a mean pore size of about 2700 Å. In some embodiments, the plurality of conjugates has a mean pore size of about 2800 Å. In some embodiments, the plurality of conjugates has a mean pore size of about 2900 Å. In some embodiments, the plurality of conjugates has a mean pore size of about 3000 Å. In some embodiments, the plurality of conjugates has a mean pore size of about 3100 Å. In some embodiments, the plurality of conjugates has a mean pore size of about 3200 Å. In some embodiments, the plurality of conjugates has a mean pore size of about 3300 Å. In some embodiments, the plurality of conjugates has a mean pore size of about 3400 Å. In some embodiments, the plurality of conjugates has a mean pore size of about 3600 Å. In some embodiments, the plurality of conjugates has a mean pore size of about 3600 Å. In some embodiments, the plurality of conjugates has a mean pore size of about 3700 Å. In some embodiments, the plurality of conjugates has a mean pore size of about 3800 Å. In some embodiments, the plurality of conjugates has a mean pore size of about 3900 Å. In some embodiments, the plurality of conjugates has a mean pore size of about 4000 Å.

In particular embodiments, the plurality of conjugates has a mean pore size of about 2000 Å.

In some embodiments, the plurality of conjugates has a dT/resin charge of less than 5 mg/mL (e.g., less than 4 mg/mL, less than 3 mg/mL, less than 2 mg/mL, less than 1 mg/mL, or less than 0.5 mg/mL).

In some embodiments, the plurality of conjugates has a dT/resin charge of about 3 mg/mL (e.g., a dT/resin charge of 3 mg/mL).

In some embodiments, the plurality of conjugates has an ionic capacity of greater than 5 μmol/mL.

In some embodiments, the plurality of conjugates has an ionic capacity of from 5 to 10 μmol/mL (e.g., 5 to 7 μmol/mL, 6 to 8 μmol/mL, 7 to 9 μmol/mL, or 8 to 10 μmol/mL). In some embodiments, the plurality of conjugates has an ionic capacity of about 5 μmol/mL (e.g., an ionic capacity of 5 μmol/mL). In some embodiments, the plurality of conjugates has an ionic capacity of about 6 μmol/mL (e.g., an ionic capacity of 6 μmol/mL). In some embodiments, the plurality of conjugates has an ionic capacity of about 7 μmol/mL (e.g., an ionic capacity of 7 μmol/mL). In some embodiments, the plurality of conjugates has an ionic capacity of about 8 μmol/mL (e.g., an ionic capacity of 8 μmol/mL). In some embodiments, the plurality of conjugates has an ionic capacity of about 9 μmol/mL (e.g., an ionic capacity of 9 μmol/mL). In some embodiments, the plurality of conjugates has an ionic capacity of about 10 μmol/mL (e.g., an ionic capacity of 10 μmol/mL).

In some embodiments, the plurality of conjugates has a dynamic binding capacity of greater than 1.5 μmol/mL (e.g., greater than 2 μmol/mL, greater than 3 μmol/mL, greater than 4 μmol/mL, greater than 5 μmol/mL, or greater than 10 μmol/mL). In some embodiments, the plurality of conjugates has a dynamic binding capacity of from 1.5 μmol/mL to 10 μmol/mL. In some embodiments, the plurality of conjugates has a dynamic binding capacity of about 2 μmol/mL (e.g., a dynamic binding capacity of 2 μmol/mL). In some embodiments, the plurality of conjugates has a dynamic binding capacity of about 2.5 μmol/mL (e.g., a dynamic binding capacity of 2.5 μmol/mL). In some embodiments, the plurality of conjugates has a dynamic binding capacity of about 3 μmol/mL (e.g., a dynamic binding capacity of 3 μmol/mL). In some embodiments, the plurality of conjugates has a dynamic binding capacity of about 3.5 μmol/mL (e.g., a dynamic binding capacity of 3.5 μmol/mL). In some embodiments, the plurality of conjugates has a dynamic binding capacity of about 4 μmol/mL (e.g., a dynamic binding capacity of 4 μmol/mL). In some embodiments, the plurality of conjugates has a dynamic binding capacity of about 4.5 μmol/mL (e.g., a dynamic binding capacity of 4.5 μmol/mL). In some embodiments, the plurality of conjugates has a dynamic binding capacity of about 5 μmol/mL (e.g., a dynamic binding capacity of 5 μmol/mL). In some embodiments, the plurality of conjugates has a dynamic binding capacity of about 5.5 μmol/mL (e.g., a dynamic binding capacity of 5.5 μmol/mL). In some embodiments, the plurality of conjugates has a dynamic binding capacity of about 6 μmol/mL (e.g., a dynamic binding capacity of 6 μmol/mL). In some embodiments, the plurality of conjugates has a dynamic binding capacity of about 6.5 μmol/mL (e.g., a dynamic binding capacity of 6.5 μmol/mL). In some embodiments, the plurality of conjugates has a dynamic binding capacity of about 7 μmol/mL (e.g., a dynamic binding capacity of 7 μmol/mL). In some embodiments, the plurality of conjugates has a dynamic binding capacity of about 7.5 μmol/mL (e.g., a dynamic binding capacity of 7.5 μmol/mL). In some embodiments, the plurality of conjugates has a dynamic binding capacity of about 8 μmol/mL (e.g., a dynamic binding capacity of 8 μmol/mL). In some embodiments, the plurality of conjugates has a dynamic binding capacity of about 8.5 μmol/mL (e.g., a dynamic binding capacity of 8.5 μmol/mL). In some embodiments, the plurality of conjugates has a dynamic binding capacity of about 9 μmol/mL (e.g., a dynamic binding capacity of 9 μmol/mL). In some embodiments, the plurality of conjugates has a dynamic binding capacity of about 9.5 μmol/mL (e.g., a dynamic binding capacity of 9.5 μmol/mL). In some embodiments, the plurality of conjugates has a dynamic binding capacity of about 10 μmol/mL (e.g., a dynamic binding capacity of 10 μmol/mL).

In another aspect, the disclosure features a method of purifying a ribonucleic acid (RNA) transcript including a poly-adenosine tail, the method including:

(a) obtaining a first sample including the RNA transcript, where the first sample includes at least 5% impurities;
(b) contacting the first sample with the composition of any of the foregoing embodiments of the disclosure under conditions such that the RNA transcript binds to a conjugate in the composition;
(c) eluting the RNA transcript from the composition; and
(d) collecting the RNA transcript in a second sample.

In some embodiments, the second sample includes less than 5% impurities (e.g., less than 4.5% impurities, less than 4% impurities, less than 3.5% impurities.

In some embodiments, the method further includes washing the composition with a surface with a solution after step (b).

In some embodiments, the method further includes preheating the first sample before step (b).

In some embodiments, the first sample includes deoxyribonucleic acid (DNA) and the first sample has not been subjected to DNase treatment.

In some embodiments, the one or more impurities include an RNA that does not include a poly-adenosine tail, DNA, a carbohydrate, a toxin, a polypeptide, and/or a nucleotide.

In some embodiments, the DNA is plasmid DNA. In other embodiments, the DNA is polymerase chain reaction product DNA. In still other embodiments, the DNA includes non-amplified DNA template.

In some embodiments, the toxin is lipopolysaccharide. In particular embodiments, the lipopolysaccharide is an endotoxin.

In some embodiments, the contacting step is performed at a temperature of about 65° C.

In some embodiments, the contacting step is performed at a rate of 100 cm/h.

In some embodiments, the first sample includes a salt solution. In particular embodiments, the salt solution is a sodium chloride solution.

In some embodiments, the washing step includes applying one or more solutions including a salt.

In particular embodiments, the salt is sodium chloride or potassium chloride.

In some embodiments, the elution step is performed with an elution buffer. In particular embodiments, the elution buffer is salt-free.

In some embodiments, the elution step is performed at a temperature of about 65° C.

In some embodiments, the RNA transcript is the product of in vitro transcription using a non-amplified DNA template.

In some embodiments, the RNA transcript is at least 1000 nucleotides in length. In some embodiments, the RNA transcript is from 1000 nucleotides to 9000 nucleotides in length. In some embodiments, the RNA transcript is from 1000 nucleotides to 8000 nucleotides in length. In some embodiments, the RNA transcript is from 1000 nucleotides to 7000 nucleotides in length. In some embodiments, the RNA transcript is from 1000 nucleotides to 6000 nucleotides in length. In some embodiments, the RNA transcript is from 1000 nucleotides to 5000 nucleotides in length. In some embodiments, the RNA transcript is from 1000 nucleotides to 4000 nucleotides in length. In some embodiments, the RNA transcript is from 1000 nucleotides to 3000 nucleotides in length.

DEFINITIONS

In this application, unless otherwise clear from context, (i) the term "a" may be understood to mean "at least one"; (ii) the term "or" may be understood to mean "and/or"; and (iii) the terms "including" and "including" may be understood to encompass itemized components or steps whether presented by themselves or together with one or more additional components or steps.

As used herein, the terms "about" and "approximately" refer to a value that is within 10% above or below the value being described. For example, the term "about 50 μm" indicates a range of from 45 μm to 55 nM.

As used herein, "binding capacity" refers to the amount of RNA that can bind to a surface per unit volume of the surface as measured in 0.5 M NaCl 10 mM Tris HCl 1 mM EDTA pH 7.4 at 25° C. In particular embodiments of measuring binding capacity, RNA is preheated to 65° C. for 15 minutes and is then adjusted with binding buffer to contain 0.5M NaCl, 10 mM Tris HCl, 1 mM EDTA, pH 7.4, at less than 1.5 mg RNA/mL; the RNA solution is contacted with the surface, heated with the surface as a slurry to 65° C. for 15 minutes, and then allowed to cool and hybridize under continuous mixing in a batch reactor for 30 minutes at 20° C.; the resin is washed, with 0.5 M NaCl, 10 mM Tris HCl, 1 mM EDTA, followed by a subsequent wash with 0.1 M NaCl, 10 mM Tris HCl, 1 mM EDTA; and RNA is eluted at 65° C. in 10 mM Tris HCl and 1 mM EDTA and then quantified by UV spectrophotometry at 260 nm, using 1 OD=40 μg at 1 cm pathlength as the conversion factor for OD to mass (mg) for, where binding capacity equals the total mg of eluted RNA (mg)/volume of surface (mL).

As used herein, "DNase treatment" refers to the addition of an endonuclease to a solution containing nucleic acids. The related activity of the endonuclease is the nonspecific degradation of DNA to release dinucleotide, trinucleotide, and oligonucleotide products with 5-phosphorylated and 3'-hydroxylated ends. DNase acts on single-stranded and double-stranded DNA and RNA:DNA hybrids.

As used herein, a "DNA template" refers to a nucleic acid template for RNA polymerase. Typically, a DNA template includes the sequence for a gene of interest linked to a RNA polymerase promoter sequence. DNA template may include non-amplified DNA.

As used herein, a "linker" refers to a moiety connecting two or more molecules or entities (e.g., a surface (e.g., polystyrene divinylbenzene particle) and an oligomer (e.g., an oligonucleotide (e.g., poly-deoxythymidine oligonucleotide))). Examples of such a linker include, but are not limited to, a linker including the structure:

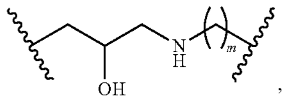, where m is 1, 2, 3, 4, 5, 6, 7, 8, 9, or 10.

As used herein, "nucleic acid" refers to a molecule of two or greater nucleotides or alternative or modified nucleotides. The term, "nucleotide" refers to a compound containing a sugar molecule (e.g., a pentose or ribose) or derivative thereof in combination with an organic base (e.g., a purine or pyrimidine) or a derivative thereof, and a phosphate group, or alternative group as described herein. Nucleic acids include DNA, RNA, tRNA (transfer RNA), mRNA (messenger RNA), siRNA (small interfering RNA), miRNA (micro RNA), shRNA (short hairpin RNA), ncRNA (non-coding RNA), aptamers, ribozymes, and shorter oligonucleotide sequences of any of the foregoing. Alterations of the base, sugar, and phosphate moiety of a nucleotide are encompassed by this definition. Exemplary nucleic acids include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), and hybrids thereof.

As used herein, an "oligomer" refers to a molecule that consists of repeating structural units. In the present invention, examples of oligomers include, but are not limited to, those having at least two thymines. Oligomers can include thymidine, deoxy thymidine, and combinations thereof. Oligomers of thymine can include other 5-carbon or 6-carbon sugars, such as, arabinose, xylose, glucose, galactose, or deoxy derivatives thereof or other mixtures of sugars. Included are analogs thereof and oligomers of various lengths. The oligomer can include one or more modifications such as: locked nucleic acid (LNA), peptide nucleic acid (PNA), morpholino nucleic acids, 2' modified RNAs, carbohydrates or derivatives thereof, or any combination of any of the above.

As used herein, the terms "polyA" or "polyA sequence" refer to a chain of adenine nucleotides. Typically, the polyA sequence is a polyA tail. As described in more detail below, a polyA sequence is typically 5-300 nucleotides in length. An RNA having a polyA sequence typically includes the coding sequence for a gene of interest. The adenosine may be naturally occurring adenosine or a derivatized version, e.g., N6-methyladenosine, capable of hybridizing to thymine. As is described herein, with respect to nucleic acids generally, the polyA sequence may also include alterations to the sugar or phosphate moiety, e.g., 2'-OMe adenosine.

As used herein, RNA that does not include "an accessible polyA sequence" refers to RNA lacking or missing sufficient polyA sequence or structure to bind to an oligomer of thymine and/or uracil. In exemplary aspects, RNA that does not include "an accessible polyA sequence" refers to RNA lacking or missing a polyA sequence and/or to RNA having a polyA sequence that is bound to another species, e.g., another nucleic acid such as RNA, DNA, or hybrids, and/or bound to itself so that the polyA sequence cannot bind to an oligomer of thymine and/or uracil; and/or that otherwise exhibits a structure, e.g., secondary structure, that prevents the polyA sequence from binding to an oligomer of thymine and/or uracil. In exemplary embodiments, RNA that does not include "an accessible polyA sequence" can also be referred to herein as RNA having or including an inaccessible polyA sequence, e.g., RNA having a polyA sequence that is bound to another species, e.g., another nucleic acid such as RNA, DNA, or hybrids, and/or bound to itself so that the polyA sequence cannot bind to an oligomer of thymine; and/or that otherwise exhibits a structure, e.g., secondary structure, that prevents the polyA sequence from binding to an oligomer of thymine.

As used herein, the term "polynucleotide" is interchangeable with nucleic acid, and includes any compound and/or substance that comprise a polymer of nucleotides. RNA transcripts produced by the method of the invention and DNA templates used in the methods of the invention are polynucleotides. Exemplary polynucleotides include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

As used herein, the term "purification" refers to the isolation of nucleic acids (e.g., ribonucleic acid) from solutions including target nucleic acids and contaminant chemical or biological material (e.g., endotoxins). Purification includes removing any unreacted product or agent in a reaction mixture that may reduce the activity of a chemical or biological component in successive steps. As used herein, purification of RNA having a polyA sequence results in the removal of sample impurities including, but not limited to, DNA (e.g., plasmid, polymerase chain reaction product, or non-amplified template), carbohydrates, toxins (e.g., lipopolysaccharide (e.g., endotoxin)), polypeptides, and RNA lacking an accessible polyA tail.

As used herein, an "RNA transcript" refers to a ribonucleic acid produced by an in vitro transcription reaction using a DNA template and an RNA polymerase. An RNA transcript typically includes the coding sequence for a gene of interest and a polyA tail. RNA transcript includes an mRNA. The RNA transcript can include modifications, e.g., modified nucleotides.

As used herein, the term "surface" refers to a part of a solid or semi-solid structure that is accessible to contact with one or more reagents or oligomers (e.g., oligonucleotides (e.g., poly-deoxythymidine oligonucleotides)).

BRIEF DESCRIPTION OF THE DRAWINGS

FIG. 23 is a table with the dT/resin charge, ionic capacity, and SBC to dA 40mer oligonucleotide, and the calculated $K_d$ and $Q_m$ values for conjugate samples 1-14.

DETAILED DESCRIPTION

Figure 1:
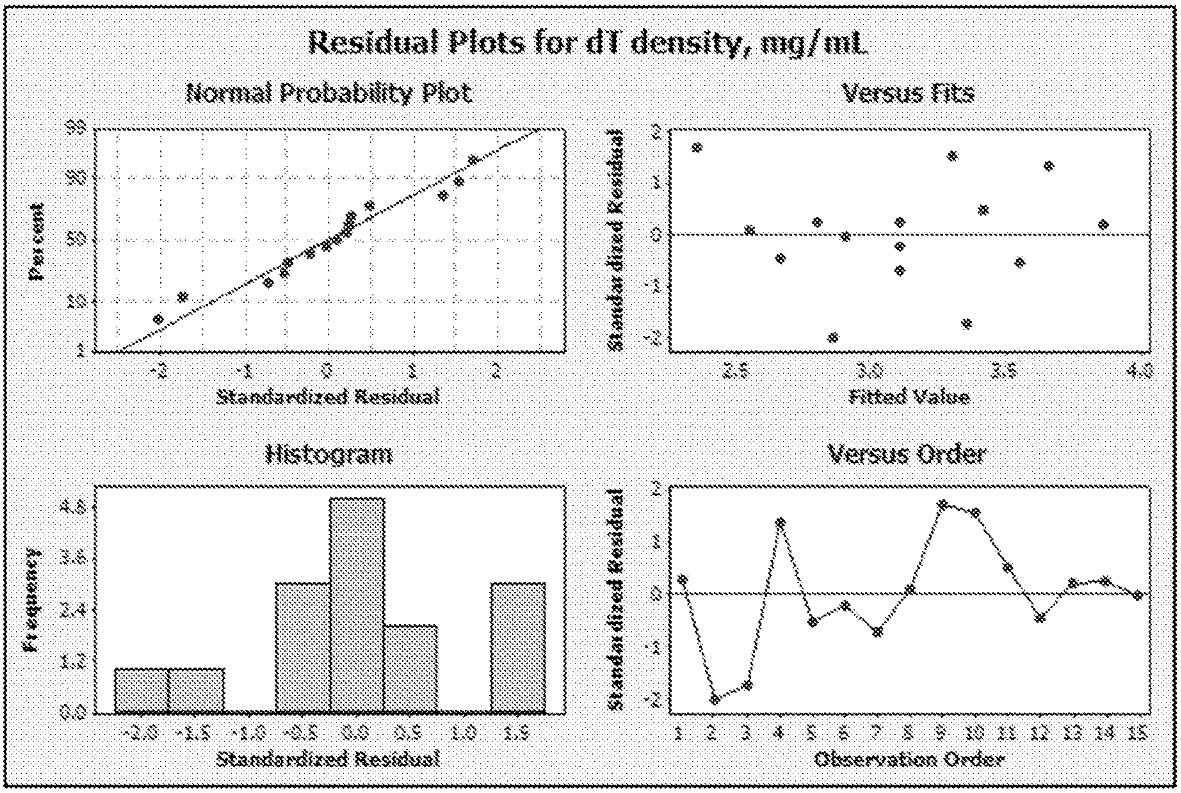
FIG. 1 illustrates the dT density of the samples in Table 1.
Figure 2:
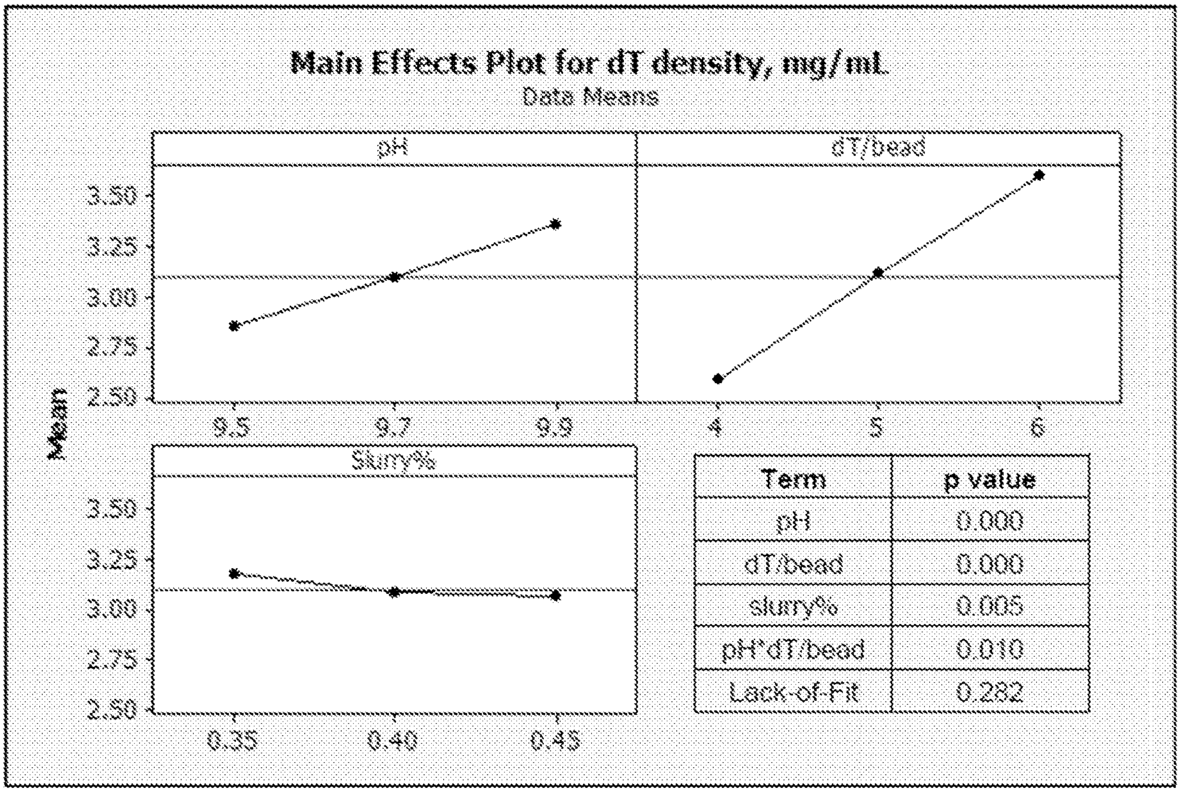
FIG. 2 illustrates the effect of pH, dT/bead ratio, and slurry concentration (%) on dT density. All three variables significantly impacted dT density. The effects were in the order of ligand offered per mL of bead=pH>slurry concentration. A higher dT density was predicted when higher amounts of ligand offered per mL of bead, higher pH, and a lower slurry concentration are used for resin synthesis.
Figure 3A:
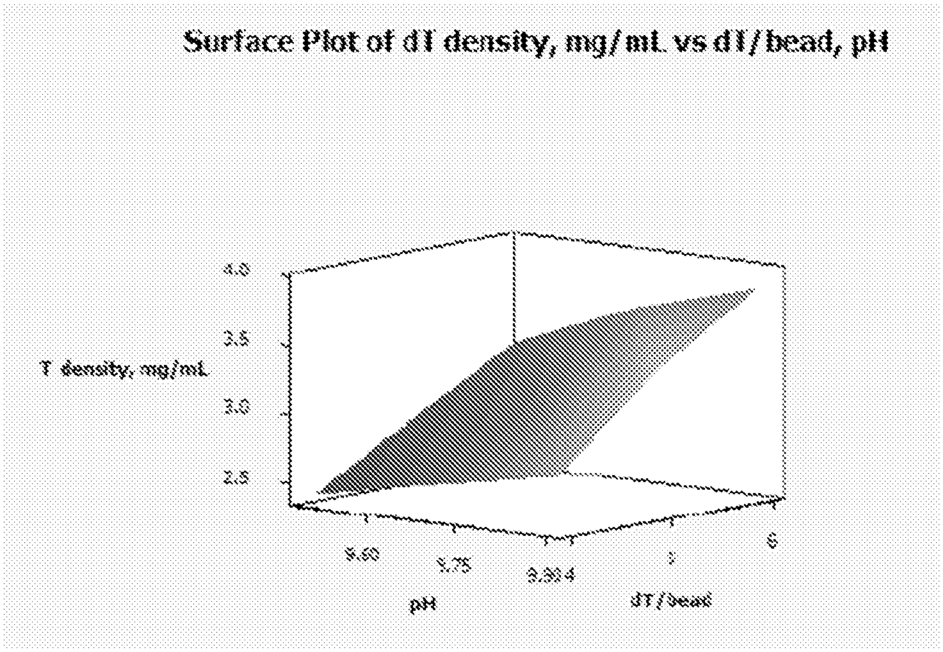
FIG. 3A, FIG. 3B, and FIG. 3C are surface plots that suggest a higher dT density is possible at a coupling pH of 9.9 and when the amount of ligand offered is >6 mg/mL of resin.
Figure 3B:
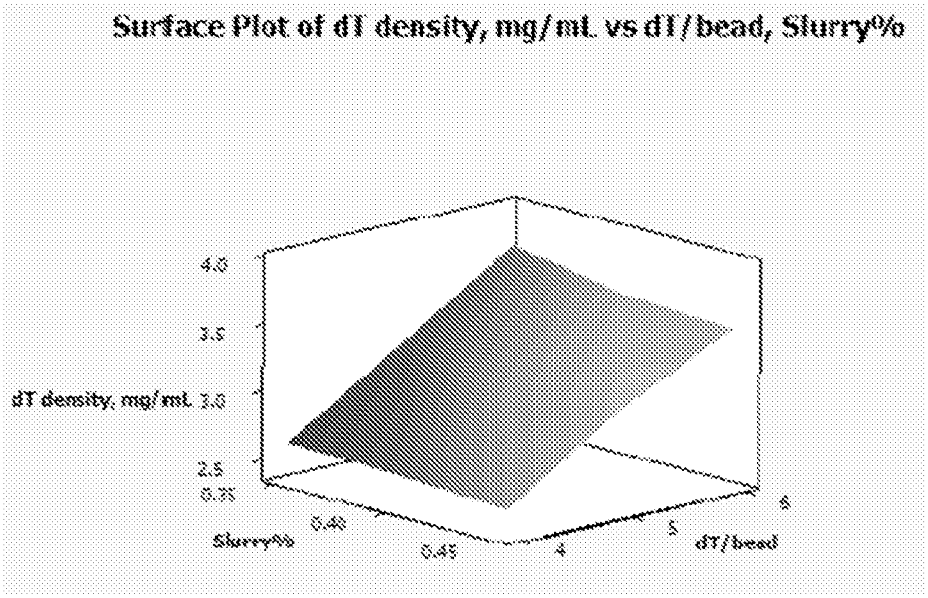
Figure 3C:
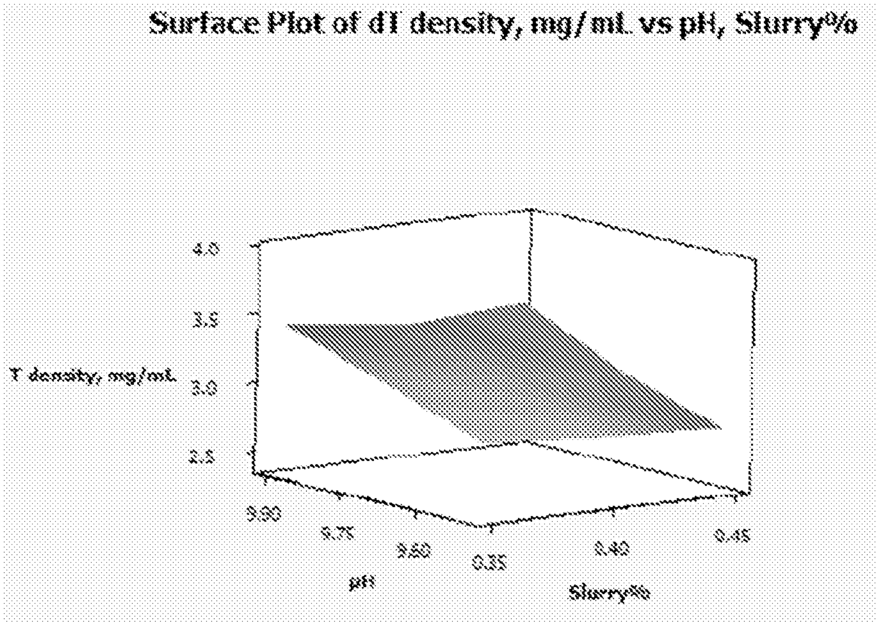
Figure 4:
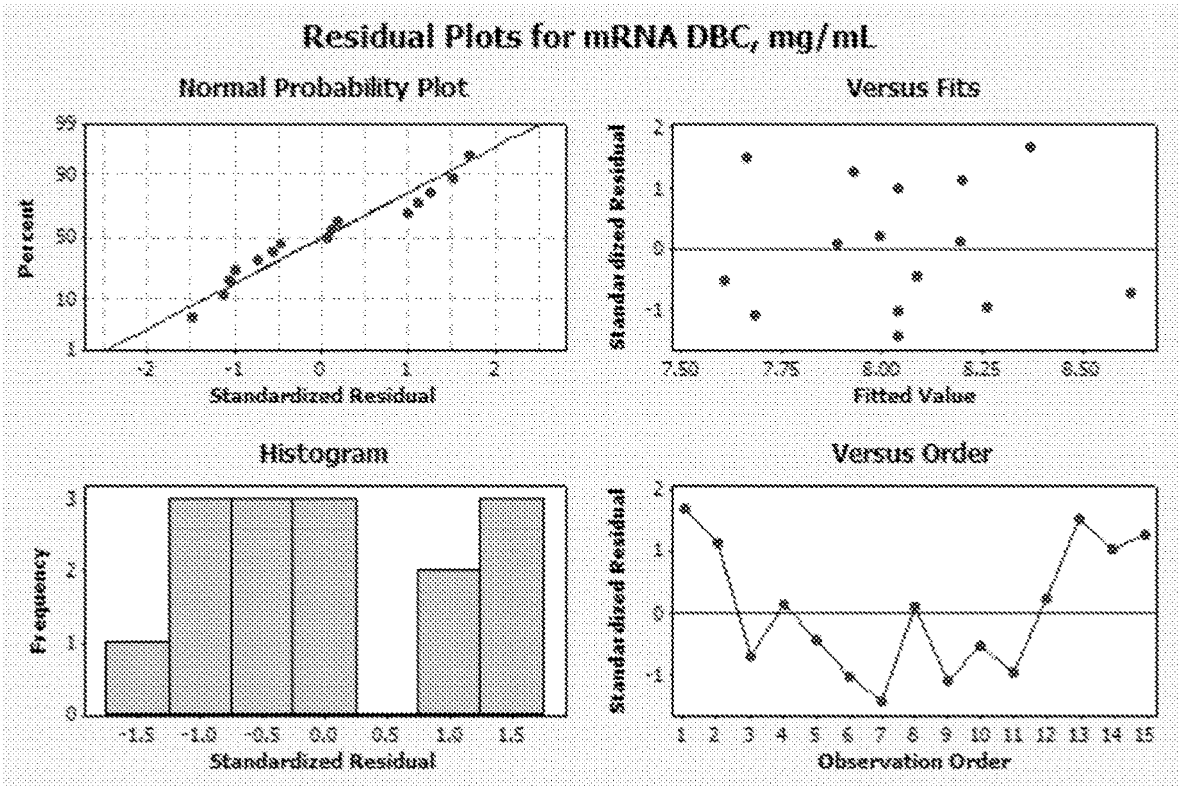
FIG. 4 illustrates residual plots for mRNA DBC (binding capacity).
Figure 5A:
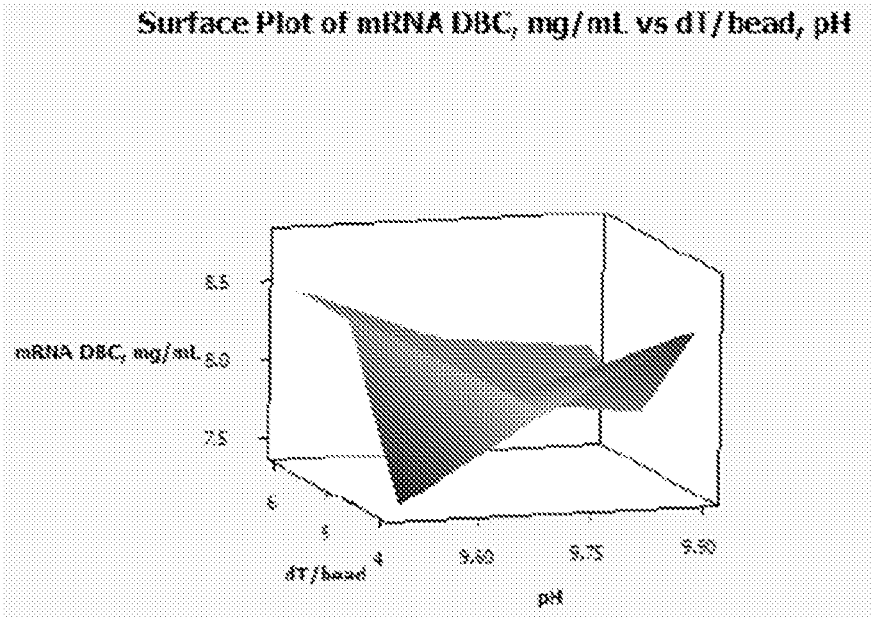
FIG. 5A, FIG. 5B, and FIG. 5C are surface plots of mRNA DBC versus dT/bead ratio and pH; mRNA DBC versus pH and slurry concentration (%); and mRNA DBC versus dT/bead ratio and slurry concentration (%). There was no correlation between the mRNA binding capacity and these three variables.
Figure 5B:
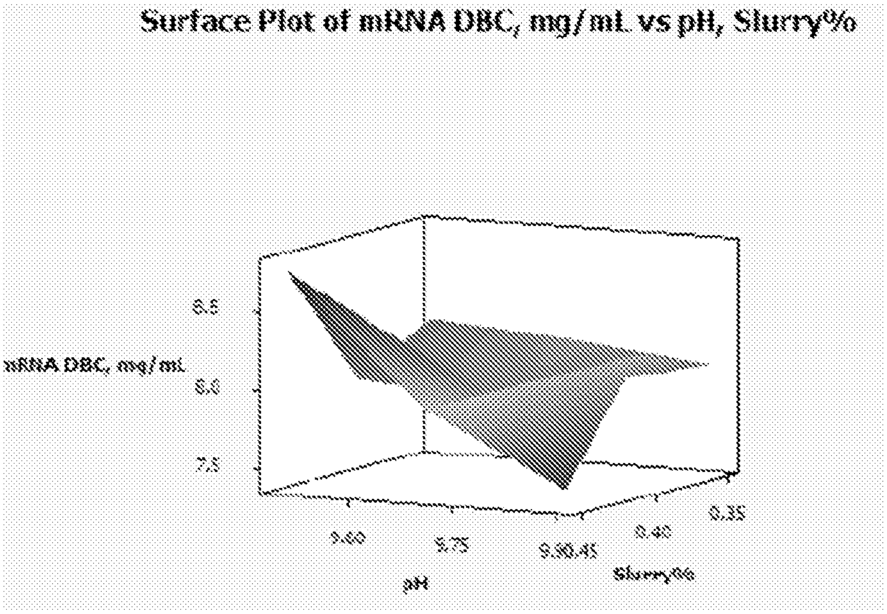
Figure 5C:
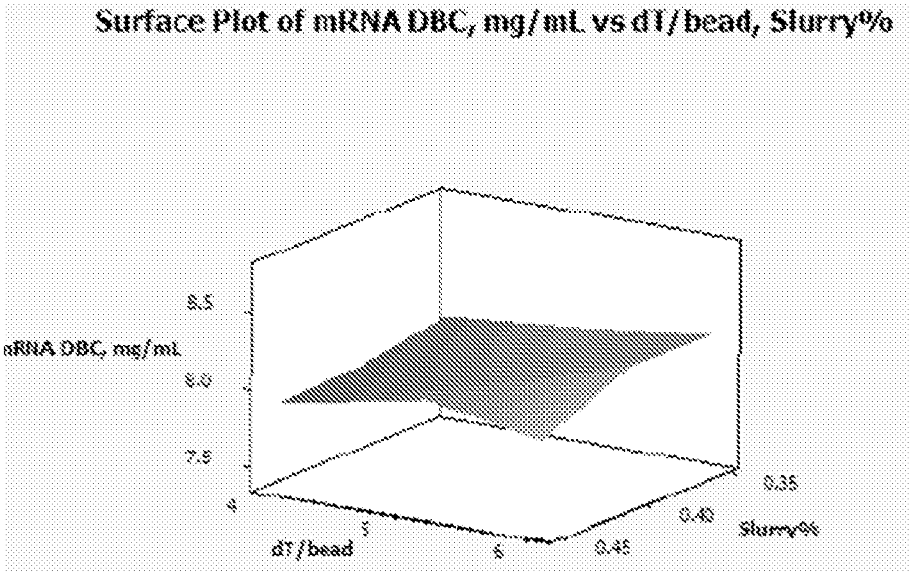
Figure 6:
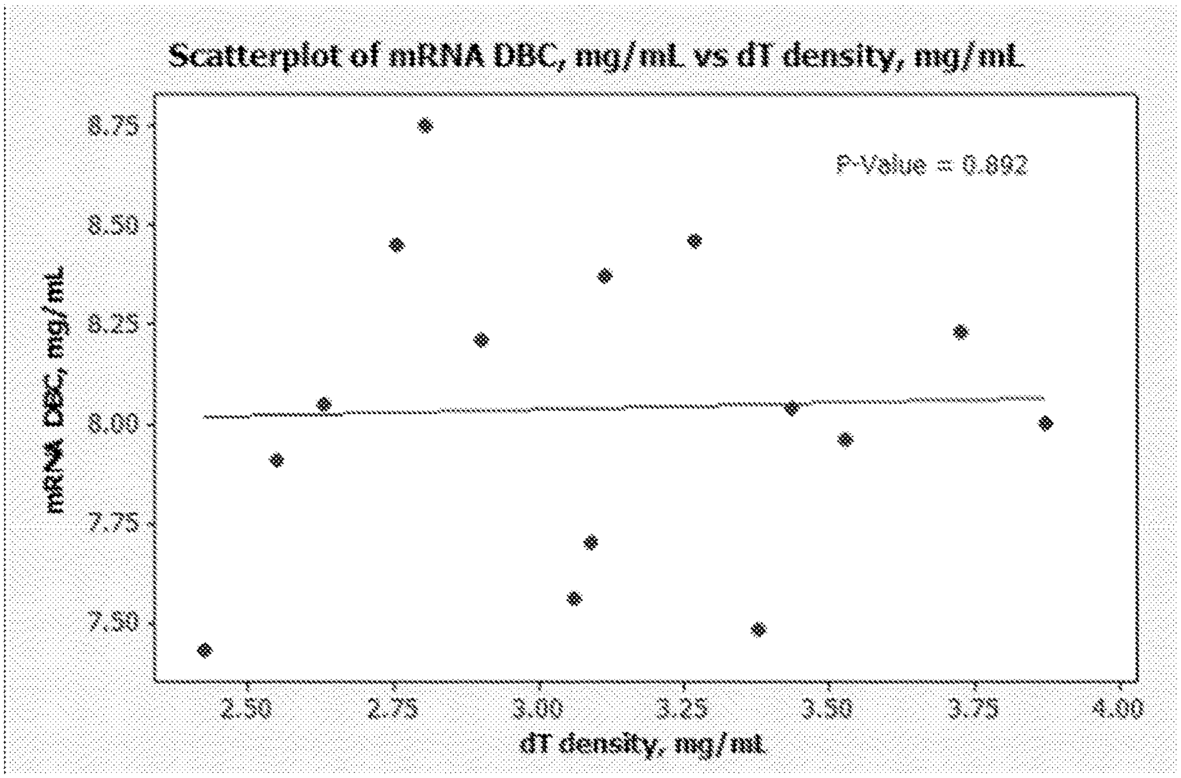
FIG. 6 is a scatterplot of mRNA DBC versus dT density. There was no significant correlation between mRNA binding capacity and dT density.

The present invention provides compositions and methods for RNA purification featuring thymine oligomers (e.g., poly-deoxythymidine oligonucleotides) linked to a surface (e.g., polystyrene divinylbenzene particle). Purification of RNA at a large scale is of great interest in the fields of molecular biology and medicine, especially for therapeutic applications. Compositions of the invention exhibit an advantageously increased binding capacity for RNA having a polyA sequence than previous compositions and allow for the purification of RNA at a large scale. Methods are also described herein for the purification of RNA comprising a polyA sequence using these compositions and for the synthesis of these surfaces linked to thymine oligomers (e.g., poly-deoxythymidine oligonucleotides).

Compositions

Compositions of the invention include a plurality of conjugates including the structure of Formula I:

A-L-B    Formula I, where A is a surface comprising a polystyrene divinylbenzene particle; L is a linker comprising the structure:

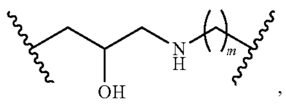
, where m is 1, 2, 3, 4, 5, 6, 7, 8, 9, or 10; and B is an oligomer comprising a poly-deoxythymidine oligonucleotide.

The poly-deoxythymidine oligonucleotides can be immobilized, coated, bound, stuck, adhered, or attached to the surface covalently. In one embodiment, the surface contains sites that can be used to attach the oligomer to a discrete site or location on the surface. Points of attachment of the oligomers may include chemical functional groups including amino groups or epoxy groups that can be used to covalently attach oligomers, which generally also contain corresponding reactive functional groups. Examples of chemically reactive groups that may be natively found on a surface or added to a surface include amino, epoxy, and/or nucleoside derivatives or any combination thereof.

The RNA binding capacity of the compositions is preferably >1 mg RNA/mL, e.g., 2-15 mg RNA/mL or >5 mg RNA/mL, >10 mg RNA/mL, >20 mg RNA/mL, >30 mg RNA/mL, or >40 mg RNA/mL.

The plurality of conjugates preferably has a mean particle size of from 40 to 60 μm (e.g., 40 to 50 μm, 50 to 60 μm, or 45 to 55 μm); a mean pore size of greater than 1000 Å (e.g., greater than 2000 Å, greater than 3000 Å, greater than 4000 Å, greater than 5000 Å, or greater than 10,000 Å); and/or an ionic capacity of from 5 to 10 μmol/mL (e.g., 5 to 7 μmol/mL, 6 to 8 μmol/mL, 7 to 9 μmol/mL, or 8 to 10 μmol/mL).

Surface

A single resin or a mixture of several resins can form a surface useful in the invention. A resin may be porous or non-porous.

In particular, the compositions and methods of the invention feature a porous surface including a polystyrene divinylbenzene particle (e.g., a polystyrene divinylbenzene particle functionalized with an epoxide). The shape, form, materials, and modifications of the polystyrene divinylbenzene particle can be selected from a range of options depending on the application.

The surface can be in the form of a bead, box, column, cylinder, disc, dish (e.g., glass or Petri dish), fiber, film, filter, microtiter plate (e.g., 96-well microtiter plate), multi-bladed stick, net, pellet, plate, ring, rod, roll, sheet, slide, stick, tray, tube, or vial. The surface can be substantially flat or planar.

Alternatively, the surface can be rounded or contoured. Exemplary contours that can be included on a surface are wells, depressions, pillars, ridges, channels or the like. Surfaces may be porous or non-porous. In one embodiment, the surface contains channels, patterns, layers, or other configurations (e.g., a patterned surface). The surface can be a singular discrete body (e.g., a single tube, a single bead), any number of a plurality of surfaces (e.g., a rack of 10 tubes, several beads), or combinations thereof (e.g., a tray comprises a plurality of microtiter plates, a column filled with beads, a microtiter plate filed with beads).

In some embodiments, a surface includes one or more pores. In some embodiments, the pore size is 1,000 to 4,000 Å (e.g., 1,000 to 2,000 Å, 2,000 to 3,000 Å, 3,000 to 4,000 Å, or 1,000 to 3,000 Å).

In some embodiments, a surface includes one or more particles (e.g., polystyrene divinylbenzene particles). In some embodiments, the particle size is 5-500 μm (e.g., 20-300 μm, 30-100 μm, 30-100 μm, 30-100 μm, 30-100 μm). In some embodiments, the particle size is 25, 30, 35, 40, 45, 50, 55, 60, 70, 80, 90, 100, 110, 120, 130, 140, 150, 160, 170, 180, 190, or 200 μm in diameter.

Poly-Deoxythymidine Oligonucleotide

As described above, compositions of the invention include a poly-deoxythymidine oligonucleotide. In certain embodiments, the poly-deoxythymidine oligonucleotide comprises 5 to 200 deoxythymidines (e.g., 5 to 20, 5 to 50, 5 to 100, 10 to 30, 15 to 25, 20 to 40, 20 to 100, 20 to 200, 100 to 200, or 150 to 200 deoxythymidines).

In some embodiments, one or more bases of the poly-deoxythymidine oligonucleotide can be modified. In some embodiments, the poly-deoxythymidine oligonucleotide can be modified to increase its chemical stability, e.g., pH or thermal stability. In certain embodiments, the poly-deoxythymidine oligonucleotide can include a 2'-oligonucleotide modification, a 5'-oligonucleotide modification, a phosphorothioate, an LNA, a PNA, a morpholino, other alternative backbones, or combinations or derivatives thereof.

Suitable poly-deoxythymidine oligonucleotides can include a naturally occurring nucleoside, e.g., thymidine, substituted deoxynucleoside, or combinations thereof. The nucleosides can also be unnatural nucleosides. The nucleosides can be joined by phosphodiester linkages or modified linkages. The nucleosides can also be joined by phosphorothioate, phosphorodithioate, or methylphosphonate linkages.

In some embodiments, the poly-deoxythymidine oligonucleotides can include pyrimidine derivatives, such as thymidine analogs, uridine analogs, and/or heterocyclic modifications, such as moieties that help maintain hybridization with adenosine.

In various embodiments, the poly-deoxythymidine oligonucleotides comprises 5 to 200 deoxythymidines (e.g., 20 to 40 deoxythymidines (e.g., 20 deoxythymidines)).

Poly-deoxythymidine oligonucleotides may be produced by any method known in the art including solid phase nucleic acid synthesis.

Linker

As described above, compositions of the invention include a linker including the structure:

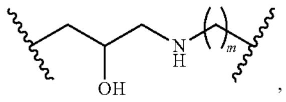

, where m is 1, 2, 3, 4, 5, 6, 7, 8, 9, or 10.

In certain embodiments, the linker can be at the 5' end of the poly-deoxythymidine oligonucleotide. In alternative embodiments, the linker can be at the 3' end of the poly-deoxythymidine oligonucleotide. In particular embodiments, the linker can be located between the ends of the poly-deoxythymidine oligonucleotide. Internal linkers can include spacer derivatives with or without modifications or nucleoside derivatives with or without modifications.

Methods of the Invention

The compositions of the invention may be used in methods for purification of RNA having a polyA sequence, e.g., on a large scale or a preparative scale.

Purification of RNA

The purification methods involve contacting the RNA with a surface including a polystyrene divinylbenzene particle that is linked to an oligomer including a polystyrene divinylbenzene particle via a linker having the structure:

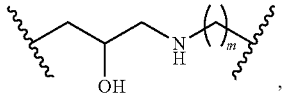

, where m is 1, 2, 3, 4, 5, 6, 7, 8, 9, or 10. The method includes optionally washing the surface and eluting the RNA from the surface. Typically, the salt concentration of the solutions is decreased from step to step.

In some embodiments, the RNA is in a composition including one or more impurities. The impurities may be 1%, 5%, 10%, 20%, 30%, 40%, 50%, 60%, 70%, 80%, 90%, 91%, 92%, 93%, 94%, 95%, 96%, 97%, 98%, or 99% of the composition, excluding solvent. In certain embodiments, one or more impurities include RNA that does not include an accessible polyA sequence, DNA, carbohydrate, toxin (e.g., lipopolysaccharide (LPS) (e.g., endotoxin)), polypeptide, and/or nucleotide. In particular embodiments, the DNA is plasmid, a polymerase chain reaction (PCR) product, or non-amplified DNA template. In any of the above embodiments, the DNA may or may not have been subjected to DNase treatment. The methods may be used to reduce impurities by at least 1%, 5%, 10%, 20%, 30%, 40%, 50%, 60%, 70, %, 80%, 90%, 95%, 99%, or 99.9%.

In some embodiments, the contacting step is performed at a temperature of 4 to 90° C., e.g., 20 to 70° C. In specific embodiments, the contacting step is performed at 4° C., 25° C., 35° C., 45° C., 55° C., 65° C., 70° C., 75° C., 80° C., 85° C., or 90° C.

In some embodiments, the contacting step is performed at a rate of 5 to 7000 cm/h, e.g., 50 to 500 cm/h. In particular aspects, the contacting step can be performed in a recirculation mode.

In some embodiments, the RNA is contacted with the surface in a composition that promotes hybridization. Such compositions may include water, salts, organic solvents, excipients, and/or buffering agents. In certain embodiments, the salt concentration is 0.1-5 M, 0.3-2.5 M, or 0.5-1 M. In further embodiments, the salt is NaCl, KCl, $MgCl_2$, $CaCl_2$, $MnCl_2$, LiCl, ammonium sulfate, potassium phosphate, or another lyotropic salt. Organic solvents include acetonitrile, alcohols (e.g., ethanol and isopropanol), dimethylsulfoxide, N,N-dimethylformamide, and other polar aprotic solvents. Excipients include DTT, detergents (e.g., Triton X), and chelating agents (e.g., EDTA). Examples of suitable buffers are provided herein.

In some embodiments, the method can further include washing the surface with a solution after RNA binding. In various embodiments, the washing solution includes a salt. In particular embodiments, the salt can be a sodium salt, potassium salt, magnesium salt, lithium salt, calcium salt, manganese salt, cesium salt, ammonium salt, and/or alkylammonium salt, e.g., NaCl, KCl, $MgCl_2$, $CaCl_2$, $MnCl_2$, and/or LiCl.

In some embodiments, the washing step includes applying a first salt buffer and a second salt buffer, wherein the first salt buffer has a higher salt concentration than the second salt buffer, and wherein the first salt buffer is applied before the second salt buffer. In specific embodiments, the first salt buffer includes 0.5M NaCl, 10 mM Tris, and 1 mM EDTA, and has a pH of 7.4. In various embodiments, the pH can be 4 to 9, e.g., 6 to 8. In particular embodiments, the second salt buffer includes 0.1M NaCl, 10 mM Tris, and 1 mM EDTA, and has a pH of 7.4. In certain embodiments, the pH can be 4 to 9, e.g., 6 to 8.

In some embodiments, the first salt buffer is applied to the surface at a temperature of 4 to 90° C., e.g., 25 to 65° C. In certain embodiments, the first salt buffer is applied to the surface twice, wherein the first application is at a higher first temperature, e.g., 65±5° C., and wherein the second application is at a lower second temperature, e.g., 25±5° C. In particular embodiments, the second salt buffer is applied to the surface at a temperature of 4 to 90° C., e.g., 25±5° C.

In some embodiments, the elution step is performed with an elution buffer. The elution buffer may include salts, organic solvents, and/or a competitive polyA oligomer. Suitable salts include guanidinium thiocyanate, guanidinium HCl, sodium perchlorate, lithium perchlorate, sodium iodide, and other chaotropic salts. Suitable organic solvents include acetonitrile, alcohols (e.g., ethanol and isopropanol), and polar aprotic solvents (e.g., N-methyl pyrrolidone, DMSO, DMF, and formamide). Suitable competitive polyA oligomers include 2'F or 2'OMe polyA or polyA LNA. In certain embodiments, the elution buffer is salt-free. In specific embodiments, the elution buffer includes 10 mM Tris and 1 mM EDTA, and has a pH of 7.4. In some embodiments, the elution buffer includes a low ionic strength un-buffered salt solution. In alternative aspects, the elution buffer includes a low ionic strength buffered salt solution. In some embodiments, the elution step is performed at a temperature of 4 to 95° C., e.g., 25 to 80° C. In certain embodiments, the elution step is performed at a temperature of 25° C. to 65° C. In specific embodiments, the elution step is performed at a temperature of 45° C. to 70° C.

Examples of buffers that can be used for any step in the method include ACES, acetate, ADA, AMP (2-amino-2-methyl-1-propanol), AMPD (2-amino-2-methyl-1,3-propanediol), AMPSO, BES, BICINE, bis-tris, BIS-TRIS propane, borate, cacodylate, carbonate, CHES, citrate, DIPSO, EPPS, HEPPS, ethanolamine, formate, glycine, glycylglycine, HEPBS, HEPES, HEPPSO, histidine, hydrazine, imidazole, malate, MES, MOBS, MOPS, MOPSO, phosphate, piperazine, piperidine, PIPES, POPSO, propionate, pyridine, pyrophosphate, succinate, TABS, TAPS, TAPSO, taurine (AES), TES, Tricine, triethanolamine (TEA), and Trizma (tris).

Any RNA having a polyA sequence may be purified using the methods of the invention. Typically, the polyA sequence is a polyA tail at the 3' end, but the methods are also applicable to accessible polyA sequences at the 5' end or in the interior of the molecule. The RNA may be naturally produced or isolated. In some embodiments, the RNA is the product of in vitro transcription using a non-amplified DNA template or chemical synthesis or combination thereof. The RNA may or may not include modifications to the sugar, base, or backbone moieties. RNA molecules may also be derivatized, e.g., by chemical linkage to another moiety. Examples of such modification are provided in U.S. application Ser. No. 13/791,922. In further embodiments, the RNA is 100 to 10,000 nucleotides in length. In various embodiments, the RNA is 500 to 4,000 nucleotides in length. In particular embodiments, the RNA is 800 to 3,000 nucleotides in length.

In some embodiments, the method is repeated 2, 3, 4, 5, 6, 7, 8, 9, 10, 15, 20, 25, 30, 35, 40, 45, 50, or greater than 50 times with the same surface.

In some embodiments, the RNA is heated prior to elution, e.g., to 25° C., 35° C., 45° C., 55° C., 65° C., 70° C., 75° C., 80° C., 85° C., or 90° C.

In some embodiments, one or more steps are performed using a batch process. In various embodiments, one or more steps of the method are performed using a column. In certain embodiments, the column can be heated and/or jacketed.

Surface Synthesis

Also disclosed herein are methods of surface synthesis and attachment of oligomers. The methods involve providing a surface including first reactive groups and contacting the surface with a plurality of oligomers including thymine and second reactive groups, under conditions so that the first and second reactive groups react to bind the oligomers to the surface. It will be understood that one or both of the reactive groups are provided by a linker bound to the oligomer or surface. Exemplary reactive groups are provided herein. In other embodiments, the first group is an epoxide, the second group is a primary amino group, and the groups are reacted under conditions for ring opening of the epoxide to a secondary amine substituted with a hydroxyl group.

EXAMPLES

Below are examples of specific embodiments for carrying out the present invention. The examples are offered for illustrative purposes only and are not intended to limit the scope of the present invention in any way.

Example 1—Synthesis of Conjugate Using Poros EP 450 Resin, 5 Hexylamine Linker, and 20Mer dT Oligonucleotide ("Conjugate EP 450")

Poros EP 450 is a porous cross-linked poly(styrene-divinylbenzene) resin activated with an epoxide functionality with a particle size of 40 μm and a pore size of 1000 Å. Poros EP 450 was utilized to immobilize a 20mer poly deoxythymidine oligonucleotide ("20mer poly dT oligo") ligand containing a 5' hexylamine linker 5'-$NH_2$—$(CH_2)_6$-TTTTTTTTTTTTTTTTTTTT-3' (SEQ ID NO:1) using the following method.

dT coupling: First, the following buffers were prepared: coupling buffer (16 mM sodium carbonate, 3 M potassium phosphate, pH 9.5 or 9.7; or 55 mM sodium carbonate, 3 M potassium phosphate, pH 9.9); washing buffer (0.1 M sodium phosphate, pH 7.0 or 7.5); dT coupling solution (determine UV convert ratio of dT ligand; then prepare 50 mg/mL dT stock aqueous solution and perform OD260 measurement to measure actual dT concentration; calculate volume of coupling buffer to prepare formulation solution); blocking buffer (1 M Tris, pH 8.0); and storage solution (20% ethanol/80% water).

Poros EP 450 resin was resuspended in 0.2 M sodium carbonate/bicarbonate buffer. Resin buffer was exchanged in 4.4 M potassium phosphate, 24 mM sodium carbonate/bicarbonate. The resin then re-slurried with 5 M potassium phosphate (50% of total volume of $PO_4$ in coupling reaction) and transferred to reaction vessel A 50 mL glass reactor was sterilized with 0.5 M NaOH solution and rinsed with process water to a neutral pH and air dried. Then 8 mL of the Poros EP 450 resin solution was charged into the 50 mL glass reactor. The mixture was shaken at 25° C. and 165 rpm for 48 hours.

Then, the appropriate amount of formulated ligand solution was charged to the reactor. After coupling, the sample was filtered and washed with 0.1 M sodium phosphate buffer (pH=7.0) on a Nalgene™ Rapid-Flow Sterile Disposable Filter (5×25 mL). The filtrate and washings were collected, combined, and used to evaluate the yield of the coupling.

Blocking: The coupled sample was washed with 1 M Tris buffer (pH=8.0; 2×25 mL) and then charged with 25 mL of 1 M Tris buffer (pH=8.0) in a 50 mL glass reactor and shaken at 25° C. at 165 rpm for 24 hours.

Final finish: After blocking, the coupled sample was washed with 0.1 M Tris buffer (pH—7.5, 2×25 mL). Then the sample was sieved through a 25 μm screen and washed with 30% ethanol (2×25 mL). The coupled sample was formulated in 20% ethanol to a slurry concentration of 50% and stored at 2-8° C.

The following samples of Conjugate EP 450 (Table 1) were synthesized using the method described above. PGP-33312

TABLE 1

| Sample No. | pH of coupling reaction | 20mer poly dT oligo/EP 450 resin ratio (mg/mL) | Slurry Conc. (%) | poly dT oligo density (mg/mL) | Coupling yield (%) | binding capacity (mg/mL) |
|---|---|---|---|---|---|---|
| 1A | 9.5 | 6 | 40 | 3.27 | 54.5 | 8.46 |
| 1B | 9.5 | 5 | 45 | 2.81 | 56.1 | 8.75 |
| 1C | 9.5 | 5 | 35 | 2.90 | 58.0 | 8.21 |
| 1D | 9.7 | 6 | 45 | 3.53 | 58.8 | 7.96 |
| 1E | 9.5 | 4 | 40 | 2.43 | 60.7 | 7.43 |
| 1F | 9.7 | 5 | 40 | 3.06 | 61.2 | 7.56 |
| 1G | 9.7 | 5 | 40 | 3.09 | 61.8 | 7.70 |
| 1H | 9.7 | 6 | 35 | 3.73 | 62.1 | 8.23 |
| 1I | 9.7 | 5 | 40 | 3.12 | 62.3 | 8.37 |
| 1J | 9.7 | 4 | 45 | 2.55 | 63.7 | 7.91 |
| 1K | 9.9 | 6 | 40 | 3.87 | 64.5 | 8.00 |
| 1L | 9.7 | 4 | 35 | 2.63 | 65.7 | 8.05 |
| 1M | 9.9 | 5 | 45 | 3.38 | 67.6 | 7.48 |
| 1N | 9.9 | 5 | 35 | 3.44 | 68.7 | 8.04 |
| 1O | 9.9 | 4 | 40 | 2.76 | 68.9 | 8.45 |

Figure 7:
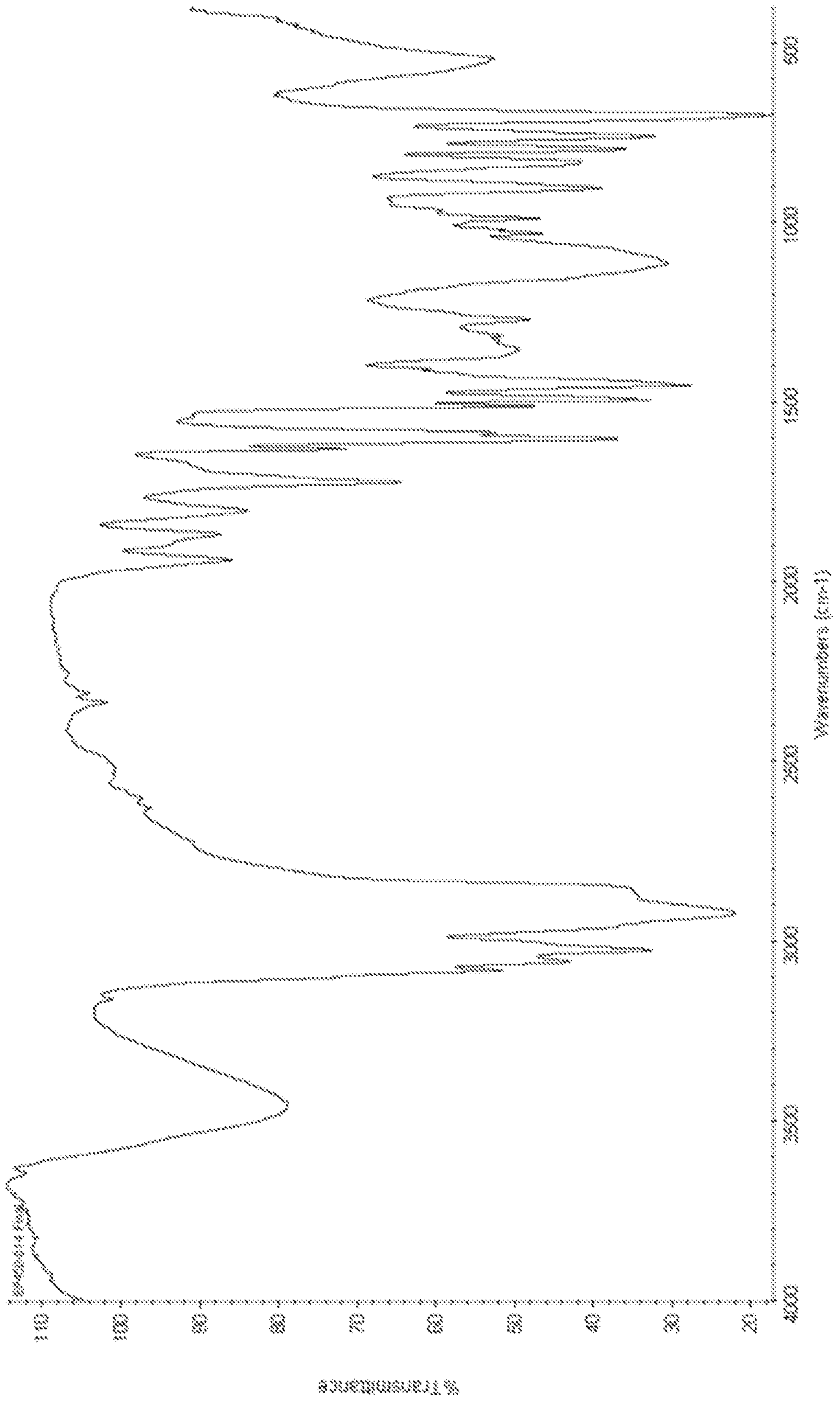
FIG. 7 is a FT-IR spectrum of Conjugate EP 450 (sample No. 11 in Table 1 of Example 1).

Results: Table 1 and FIG. 1, FIG. 2, FIG. 3A, FIG. 3B, FIG. 30, FIG. 4, FIG. 5A, FIG. 5B, FIG. 5C, and FIG. 6 illustrates the dT density, coupling yield, and mRNA binding capacity of samples with varying poly dT oligo/EP 450 resin ratio, pH of coupling reaction, and slurry concentration. In general, the poly dT oligo density ranged from 2.43-3.87 mg/mL; the coupling yield ranged from 54.5%-68.7%; and the mRNA binding capacity ranged from 7.43-8.75 mg/mL. The FT-IR spectrum of sample 11 is shown in FIG. 7.

The preferred process conditions for synthesizing the Poros EP 450 conjugate was determined to be as shown in Table 2.

TABLE 2

| Parameter | Target | Tolerance |
|---|---|---|
| Slurry Concentration | 40% | ±1% |
| pH | 9.9 | ±0.1 |
| Offered dT | 5 mg/mL | ±0.2 mg/mL |
| Time | 48 hours | +0.5 hours |
| Temperature | 25° C. | ±2° C. |

Example 2—Production Scale Synthesis of Poros EP 450 Conjugate

Figure 8A:
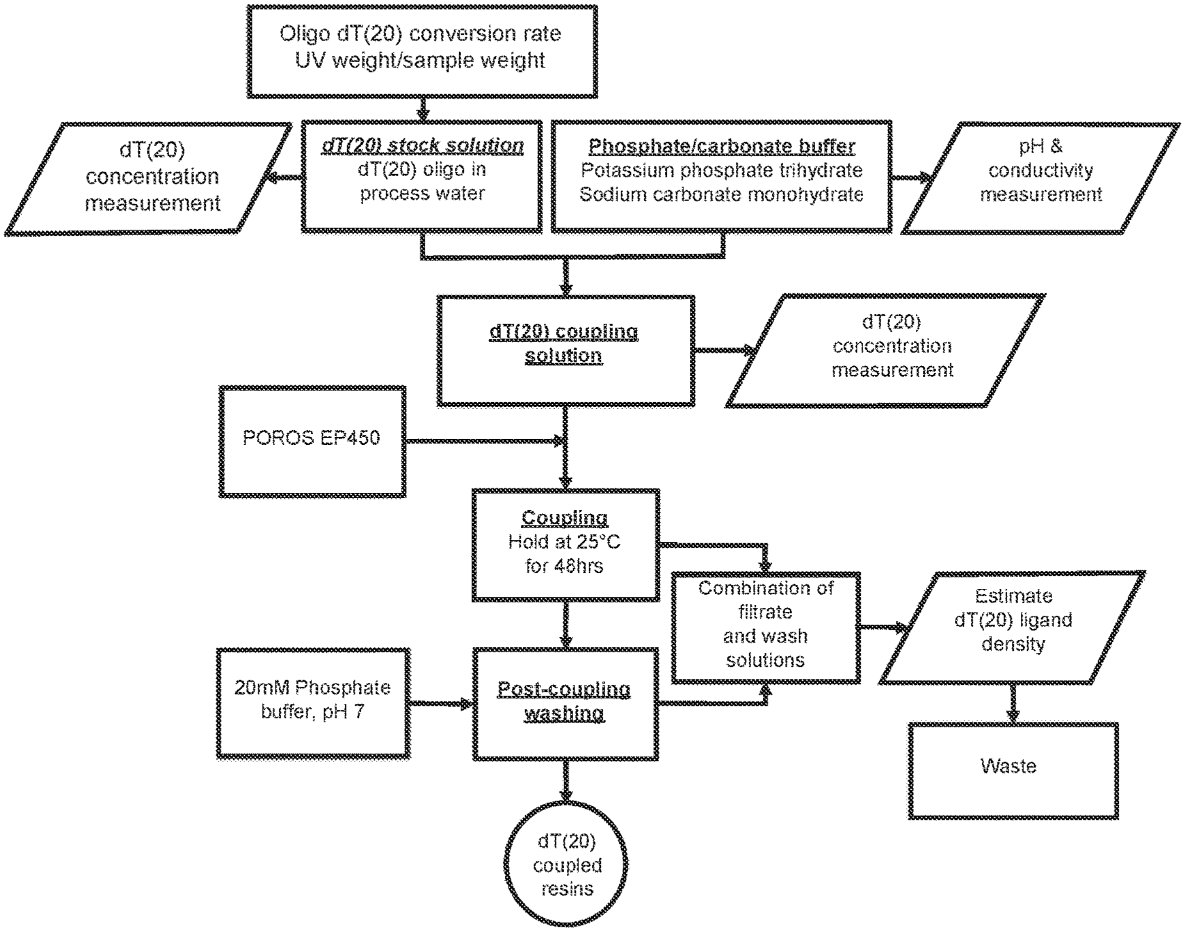
FIG. 8A and FIG. 8B illustrate the process for the synthesis of Conjugate EP 450 on production scale.
Figure 8B:
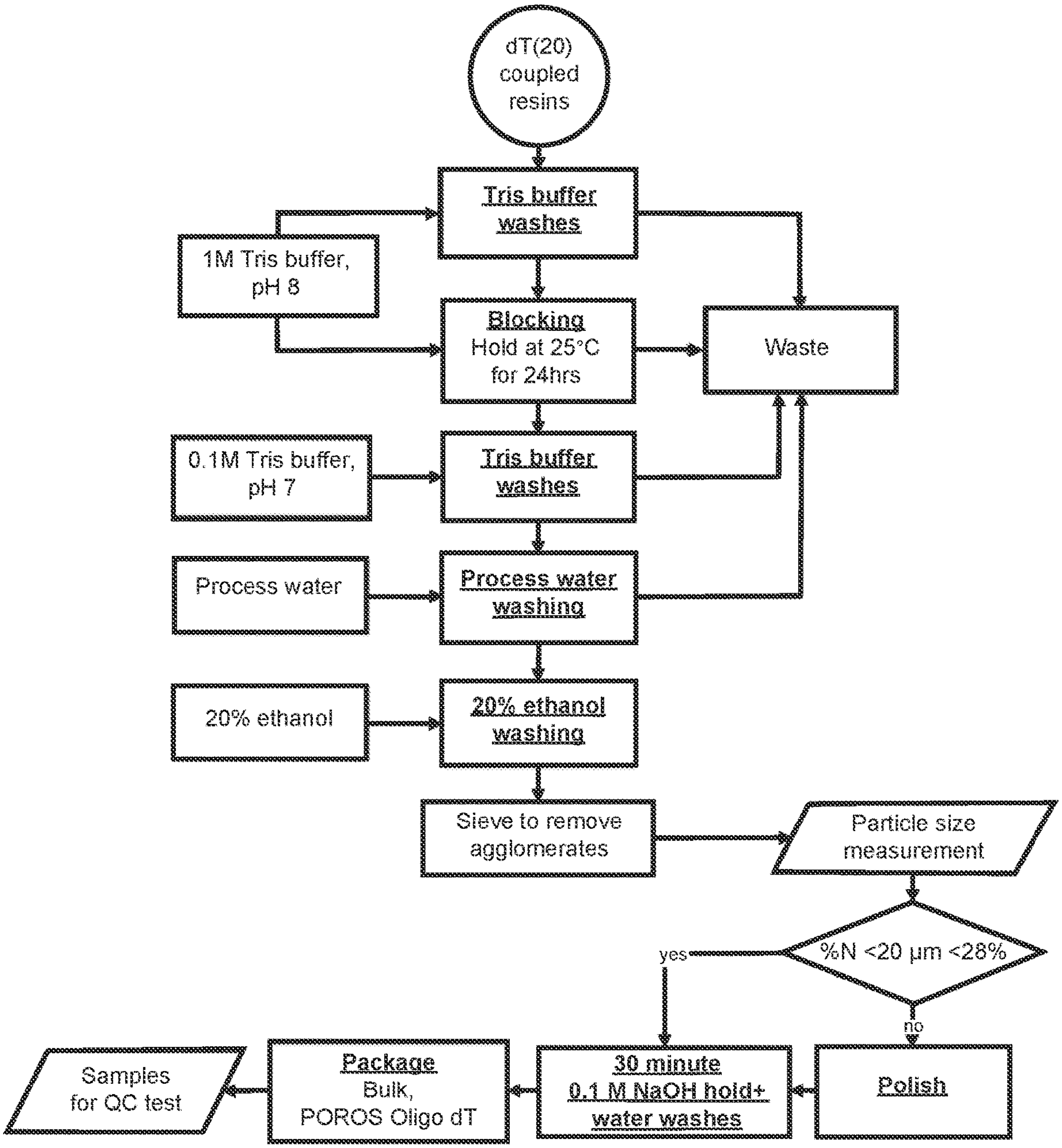

The synthesis of Conjugate EP 450 described in Example 1 was successfully completed on a production scale of 800 mL and 10 L (FIG. 8A and FIG. 8B). The following table (Table 3) shows the optimized inputs of the production scale synthesis.

TABLE 3

| Input Variable | Optimized Condition |
|---|---|
| 20mer dT oligo concentration in stock solution | 50 ± 5 mg/mL |
| 20mer dT oligo ligand/EP450 resin | 5.0 ± 0.2 mg/mL |
| 20mer dT oligo ligand concentration in coupling buffer | 3.6 ± 0.3 mg/mL |
| pH of coupling solution | 9.9 ± 0.2 |
| Conductivity of coupling solution | 165 ± 10 mS/cm |

TABLE 3-continued

| Input Variable | Optimized Condition |
|---|---|
| Time of coupling reaction | 48.0 ± 0.5 hours |
| Temperature of coupling reaction | 25 ± 2° C. |
| pH of blocking solution | 8.0 ± 0.2 |
| Conductivity of blocking solution | 32 ± 5 mS/cm |
| Time of blocking reaction | 24.0 ± 0.5 hours |
| Temperature of blocking reaction | 25 ± 2° C. |

The following table (Table 4) shows the input parameters of the production scale runs of the production scale synthesis of Poros EP 450 conjugate.

TABLE 4

| Parameters for production scale synthesis | Proposed range | 2A | 2B | 2C | 2D |
|---|---|---|---|---|---|
| Batch Size (mL) | — | 800 | 800 | 800 | 10,000 |
| [20mer poly dT oligo] in stock solution (mg/mL) | 50.0 ± 5.0 | 49.7 | 49.5 | 49.8 | 50.3 |
| 20mer poly dT oligo/mL of EP 450 resin (mg/mL) | 5.0 ± 0.2 | 5.0 | 5.0 | 5.0 | 5.0 |
| [20mer poly dT oligo] in coupling buffer (mg/mL) | 3.6 ± 0.3 | 3.6* | 3.6* | 3.6* | 3.6 |
| EP 450 Slurry Concentration (%) | 40 ± 2 | 40* | 40* | 40* | 41 |
| pH of coupling solution | 9.9 ± 0.2 | 9.9 | 9.9 | 10.1 | 10.0 |
| Conductivity of coupling solution (mS/cm) | 165 ± 10 | 168 | 165 | 165 | 158 |
| Time of coupling reaction (hours) | 48.0 ± 0.5 | 48.0 | 48.0 | 48.0 | 48.0 |
| Temperature of coupling reaction (° C.) | 25 ± 2 | 25 | 25 | 25 | 25 |
| pH of blocking solution | 8.0 ± 0.2 | 8.0 | 8.0 | 8.0 | 8.0 |
| Conductivity of blocking solution (mS/cm) | 32 ± 5 | 32 | 31 | 33 | 32 |
| Time of blocking reaction (hours) | 24.0 ± 0.5 | 24.0 | 24.0 | 24.0 | 24.0 |
| Temperature of blocking reaction (° C.) | 25 ± 2 | 25 | 25 | 25 | 25 |

*based on calculation from the batch record

Figure 9:
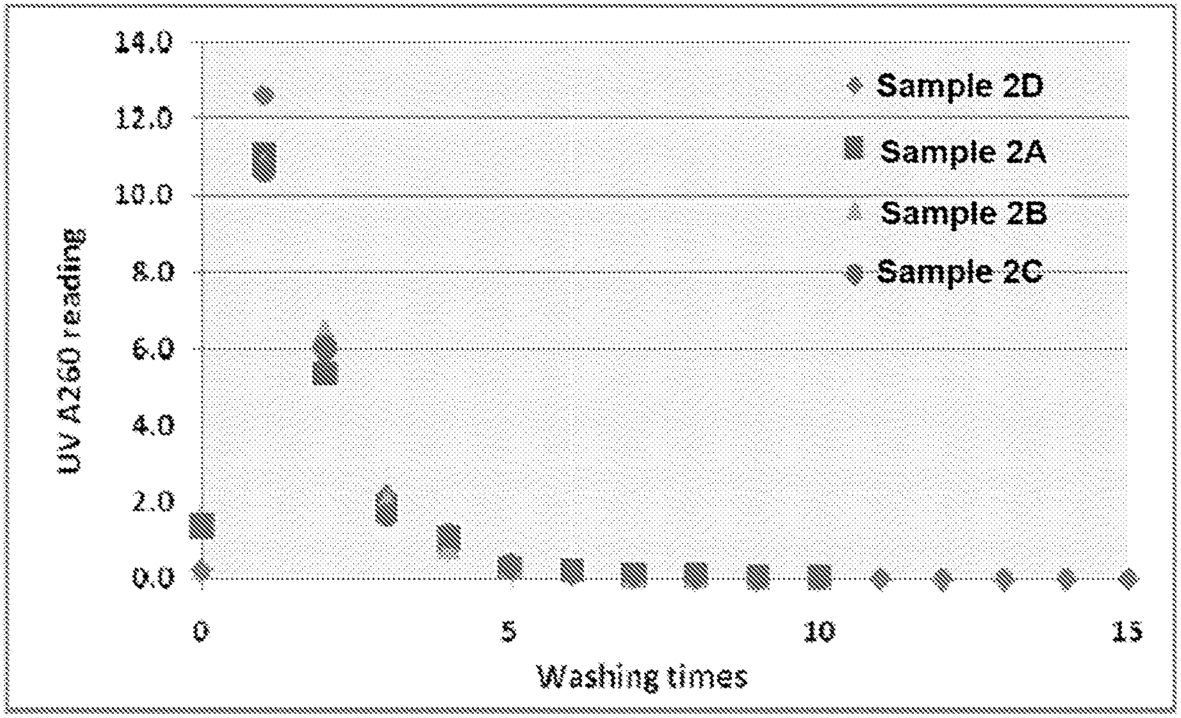
FIG. 9 illustrates the amount of unbound 20mer dT oligo after phosphate buffer washes.

The 20mer poly dT oligo content of the filtrate from the coupling reaction and buffer from each washing step was assessed by A260 measurements (FIG. 9). The ligand holds up in the pores of the resin at both the 800 mL scale and the 10,000 mL scale. Nine washes with phosphate buffer removed unbound 20mer poly dT oligo ligand for the 800 mL bath preparation. A total of fifteen phosphate buffer washes were used to ensure removal of unbound 20mer dT oligo from the 10 L production scale. A mass balance assessment by measuring the ligand in the combined filtrate and wash solutions was used to estimate immobilized ligand density.

Figure 10:
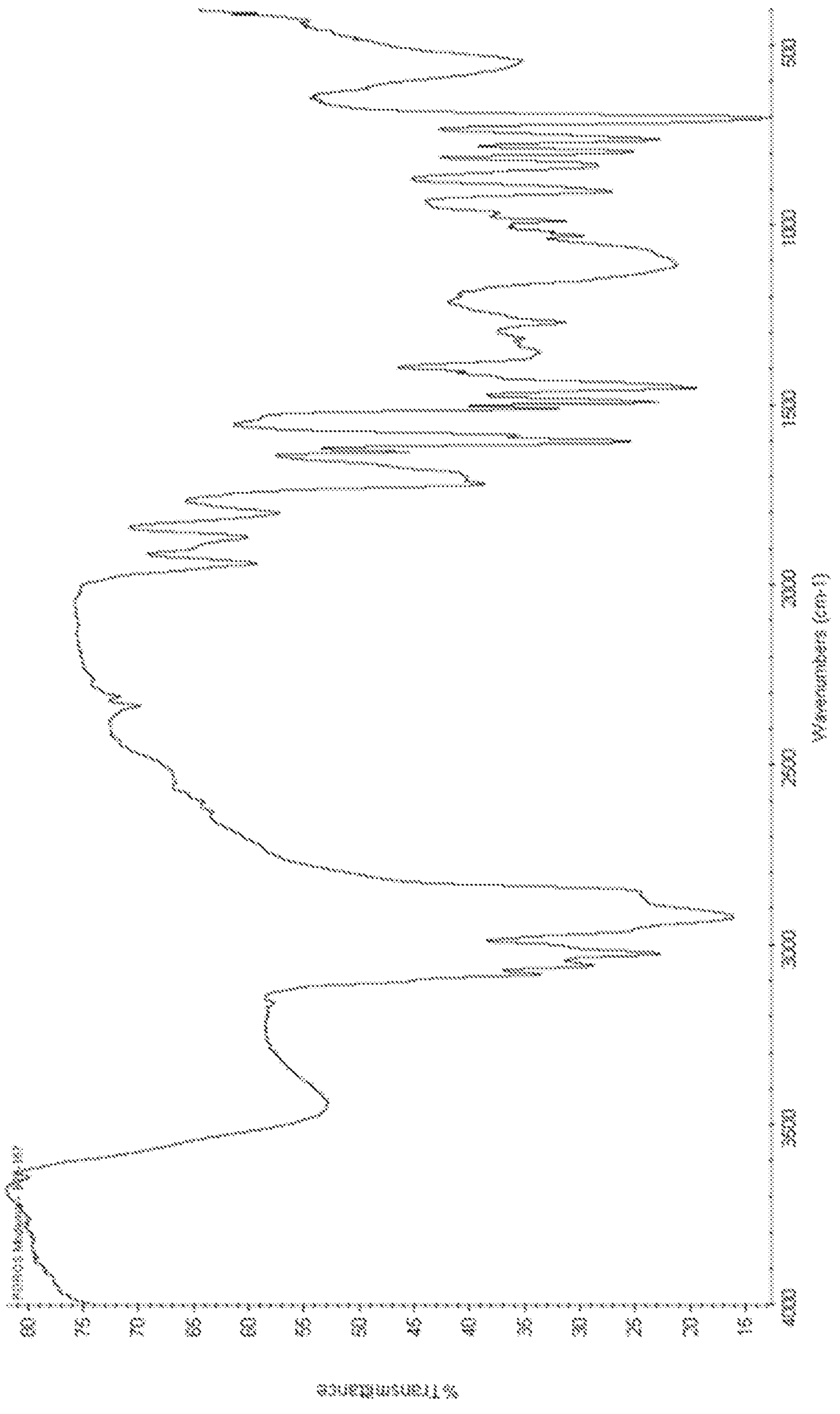
FIG. 10 is a FT-IR spectrum of Conjugate EP 450 (sample No. 2B in Table 4 from Example 2).

The following table (Table 5) shows the oligo density; coupling yield; mean particle size of the conjugate, which is calculated by multiplying Coulter mean particle size volume by 50 and dividing by 37 (i.e., correction factor of approximately 1.35); and endotoxin levels for the production scale syntheses of conjugate EP 450. The coupling reaction used to synthesize conjugate EP 450 is performed with a charge of 5 mg/mL. Product consistency was demonstrated across two production scale syntheses. The FT-IR spectrum of sample 2B is shown in FIG. 10.

TABLE 5

| Test | Unit of Measure | 2A | 2B | 2C | 2D |
|---|---|---|---|---|---|
| Oligo density | mg/mL | 3.8 | 3.9 | 3.7 | 3.7 |
| Coupling Yield | % | 75.1 | 77.7 | 73.3 | 75.4 |
| Mean Particle size | μm | 41.4 | 42.3 | 42.2 | 43.8 |
| Standard deviation | μm | 7.4 | 7.6 | 7.9 | 9.1 |

TABLE 5-continued

| Test | Unit of Measure | 2A | 2B | 2C | 2D |
|---|---|---|---|---|---|
| % Number <20 μm | % | 7.6 | 8.5 | 6.9 | 22.5 |
| Bioburden | cfu | Not tested | Not tested | Not tested | 12.8 |
| Endotoxin | EU/mL (Endotoxin Units/mL) | Not tested | Not tested | Not tested | <0.5 |

Example 3—Stability of Conjugate EP 450

The stability of conjugate EP 450 in 20% ethanol was studied under accelerated conditions (Kennon, L., Use of models determining chemical pharmaceutical stability J. of Pharmaceutical Sciences 5:815-818 (1964)). The accelerated stability samples were stored at 600° C. for 15.7 days (equivalent to 18 months storage at 25° C.) and sampled at 2.6 days at 60° C. (equivalent to 3 months at 25° C.) and at 10.6 days at 60° C. (equivalent to 12 months at 25° C.). Control sample was stored at 2-8° C. All samples were stored in 20% (v/v) ethanol. The activity of the samples was measured using plate-based HT assay to obtain the static binding capacity (SBC) using 40mer dA oligonucleotide (Table 6).

TABLE 6

| Sample No. | Days at 60° C. | Months at 25° C. | SBC* (mg/mL) | % change from control | $C_{50}$ (μmol/mL) | % change from control |
|---|---|---|---|---|---|---|
| Control | 0 | 0 | 1.56 | 0 | 10.36 | 0 |
| 3A | 2.6 | 3 | 1.63 | 4.5 | 9.90 | −4.4 |
| 3B | 10.6 | 12 | 1.50 | −3.8 | 9.47 | −8.6 |
| 3C | 15.7 | 18 | 1.39 | −10.9 | 9.28 | −10.4 |

*Conjugate activity including second elution

Figure 11A:
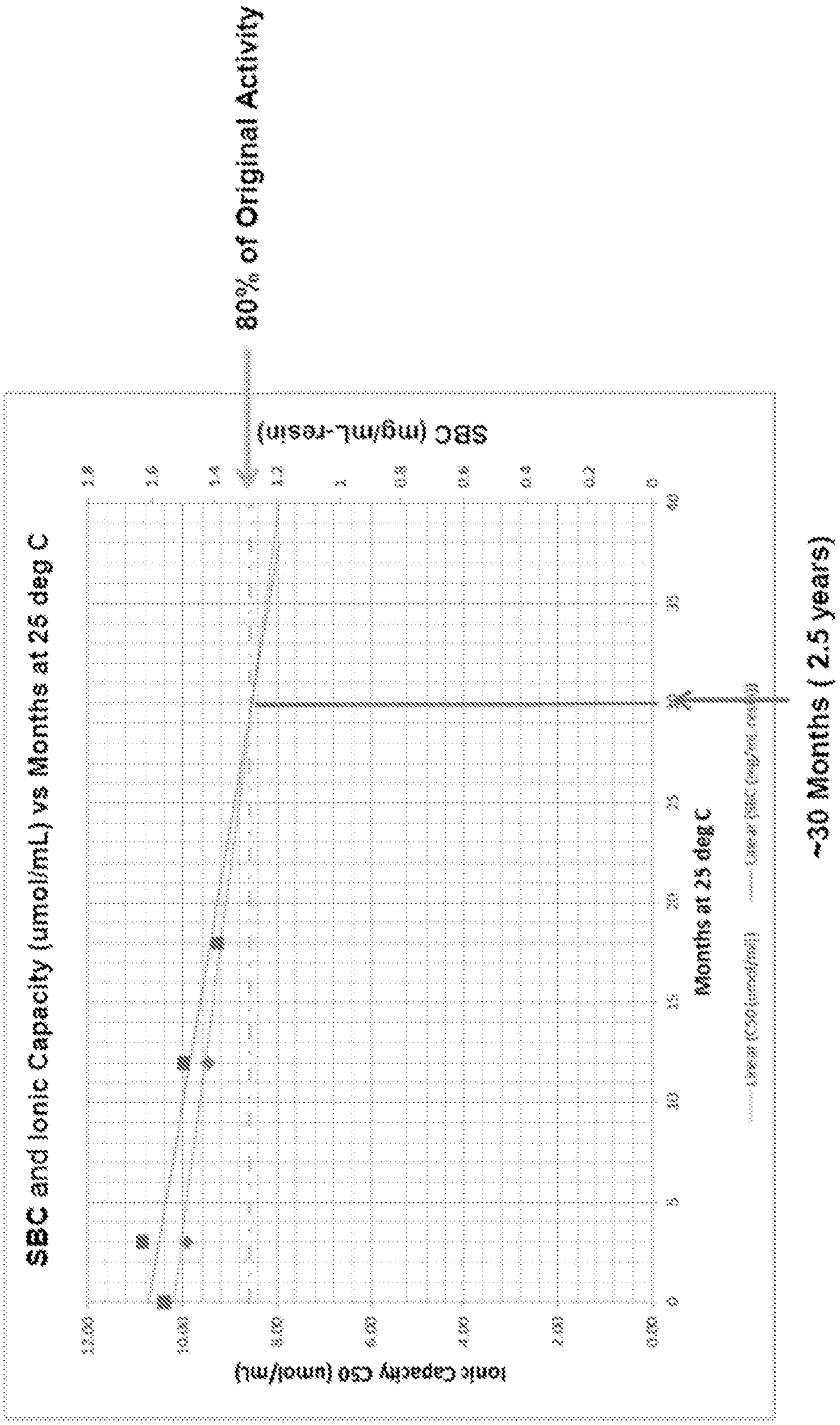
FIG. 11A and FIG. 11B illustrate that the predicted stability of conjugate EP 450 studied under accelerated conditions and based on ionic capacity and static binding capacity (SBC) measurements. Extrapolation of both the ionic capacity and static binding capacity (SBC) suggest that about 80% of the original activity will be retained for up to about 30 months if the conjugate EP 450 is stored at 25° C. in 20% ethanol (FIG. 11A). Extrapolation of SBC suggest that about 90% of the original activity will be retained for up to 205 months if the conjugate EP 450 is stored at 5° C. in 20% ethanol (FIG. 11B).
Figure 11B:
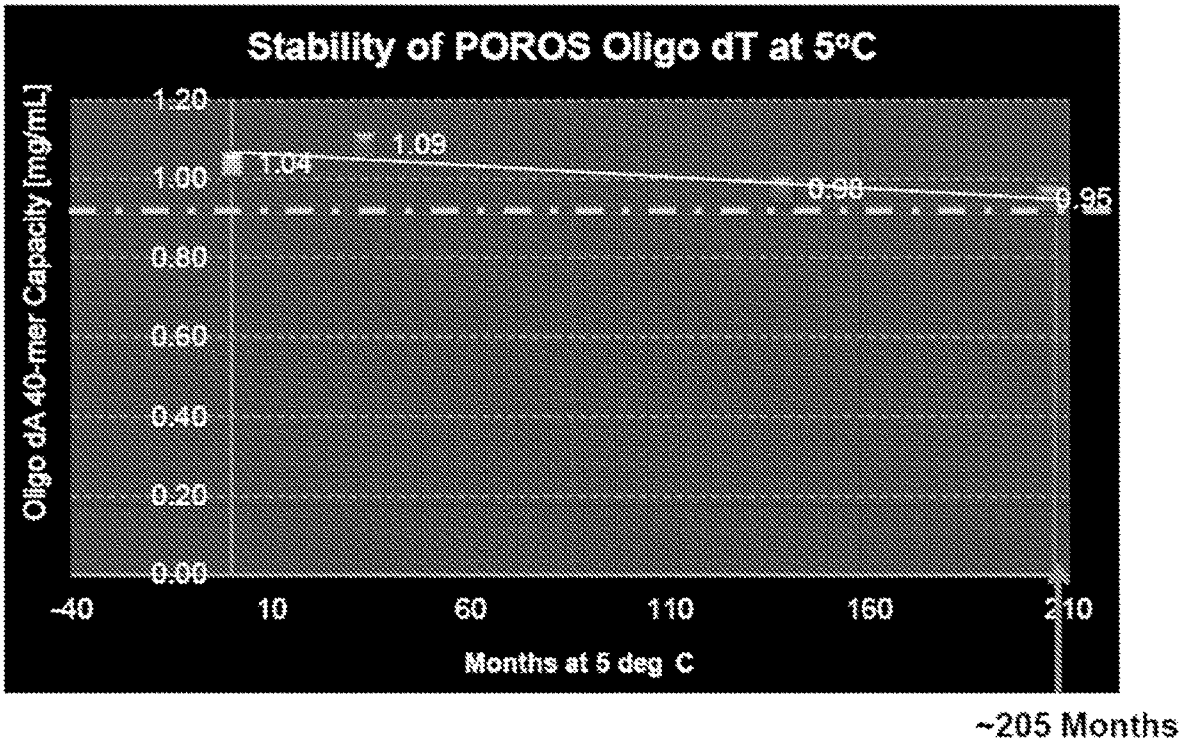
Figure 12:
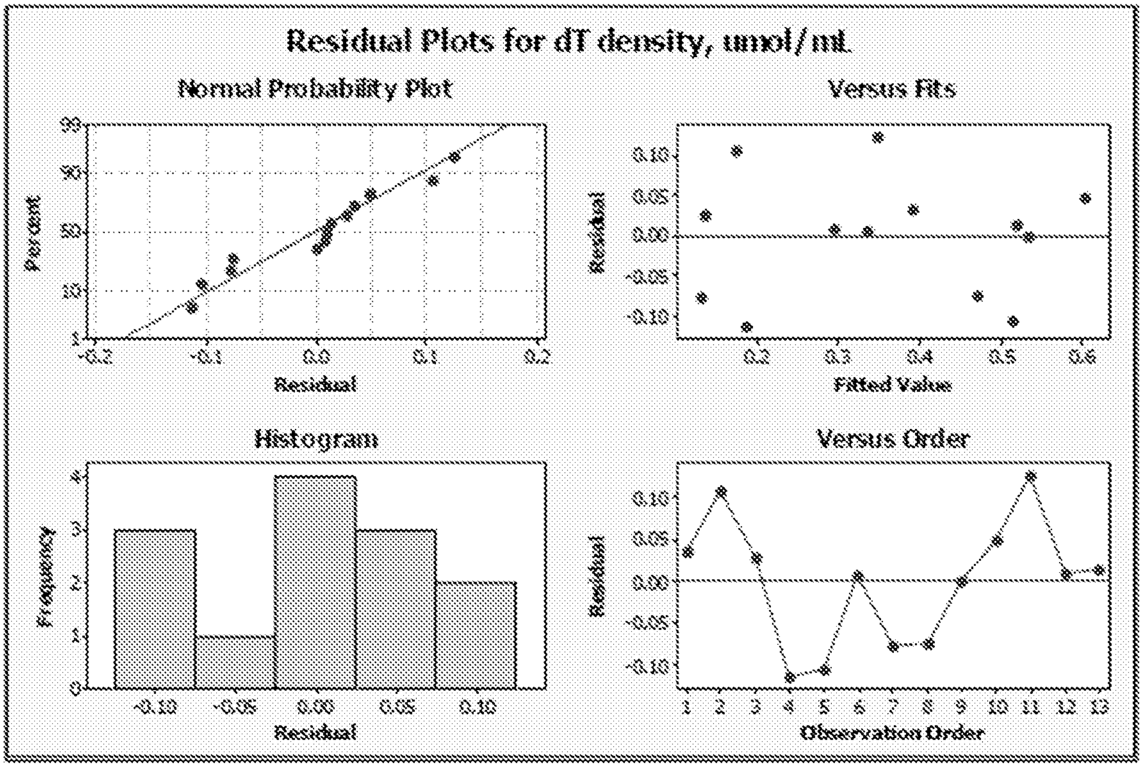
FIG. 12 illustrates the ionic capacity of the samples in Table 7.
Figures 13A, 13B:
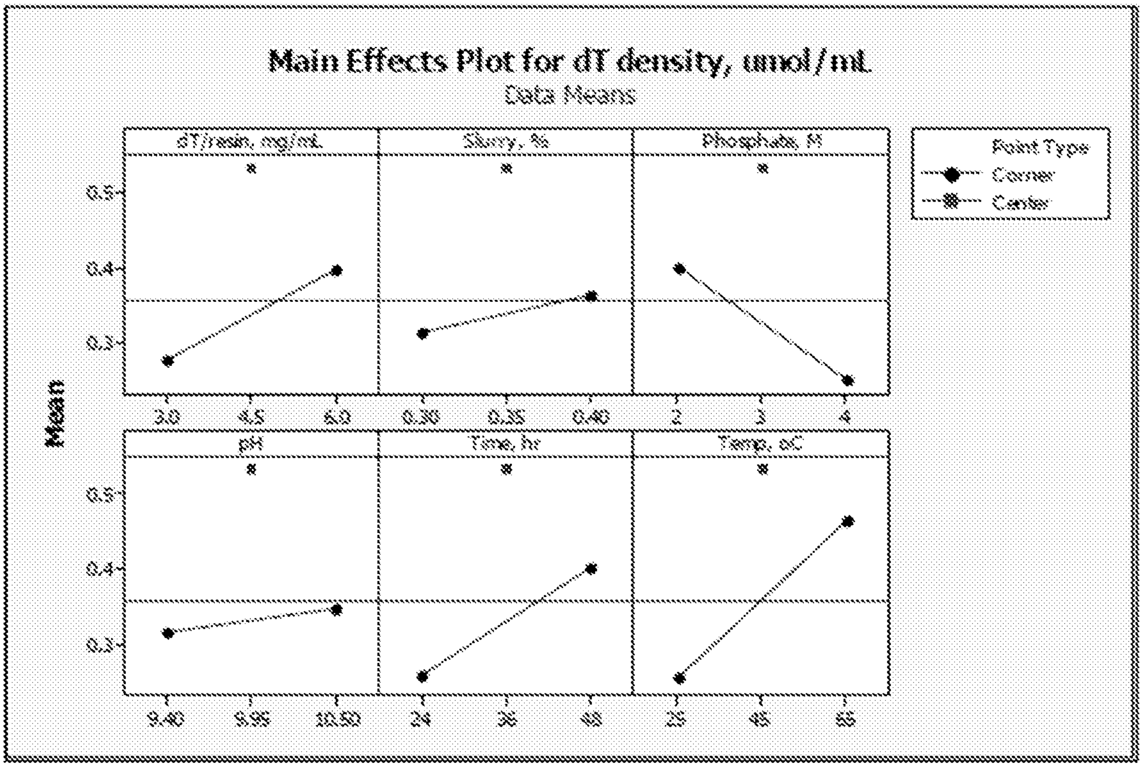
FIG. 13A and FIG. 13B illustrate that the coupling temperature impacted the ionic capacity, whereas pH and slurry concentration had minimum impact on ionic capacity. Additionally, the coupling time, phosphate concentration, and dT/resin ratio had marginal impact on dT density.
Figure 14:
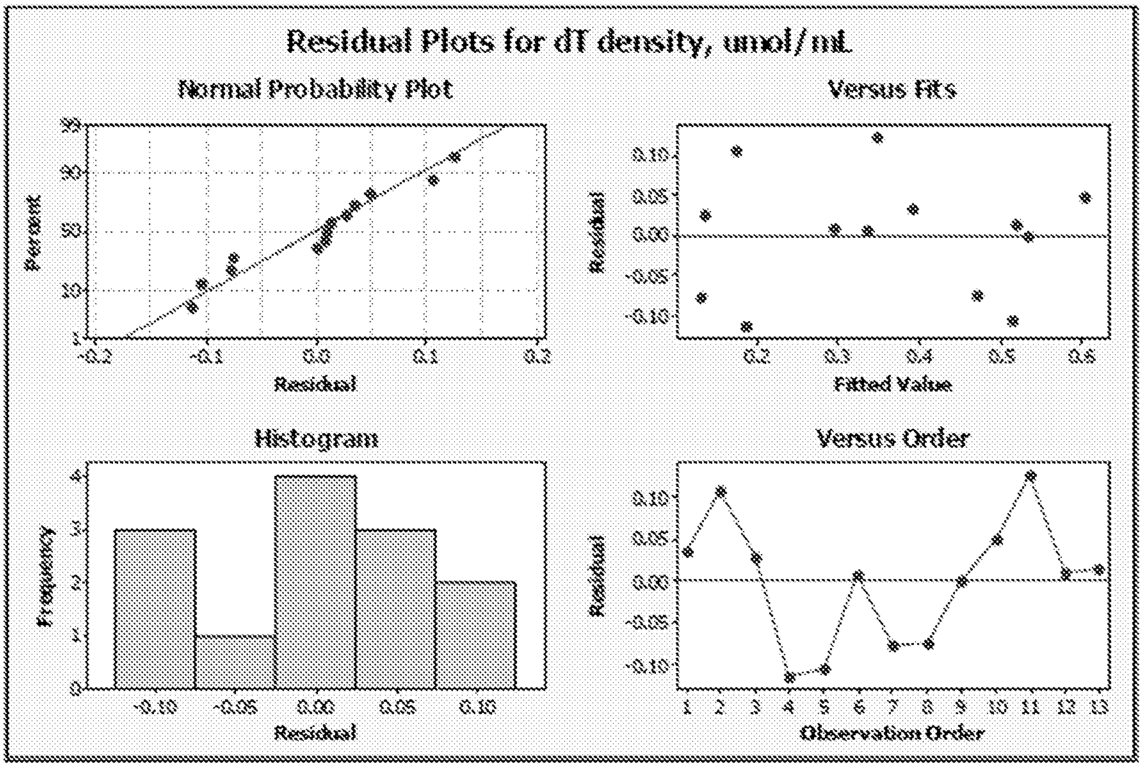
FIG. 14 illustrate the 40mer dA binding capacity of the samples in Table 7.
Figures 15A, 15B:
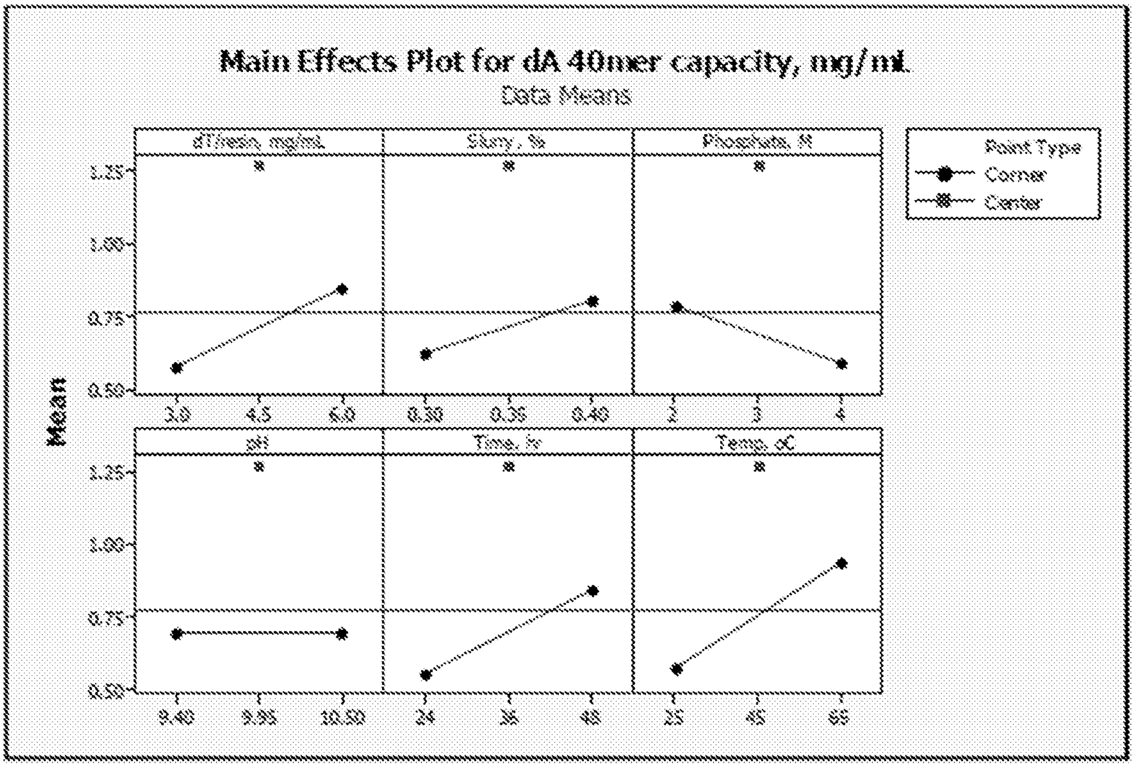
FIG. 15A and FIG. 15B illustrate that the coupling temperature impacted the 40mer dA binding capacity. The coupling time and dT/resin ration had marginal impact on 40mer dA binding capacity. The pH, phosphate concentration, and slurry concentration had minimum impact on the 40mer dA binding capacity.
Figure 16A:
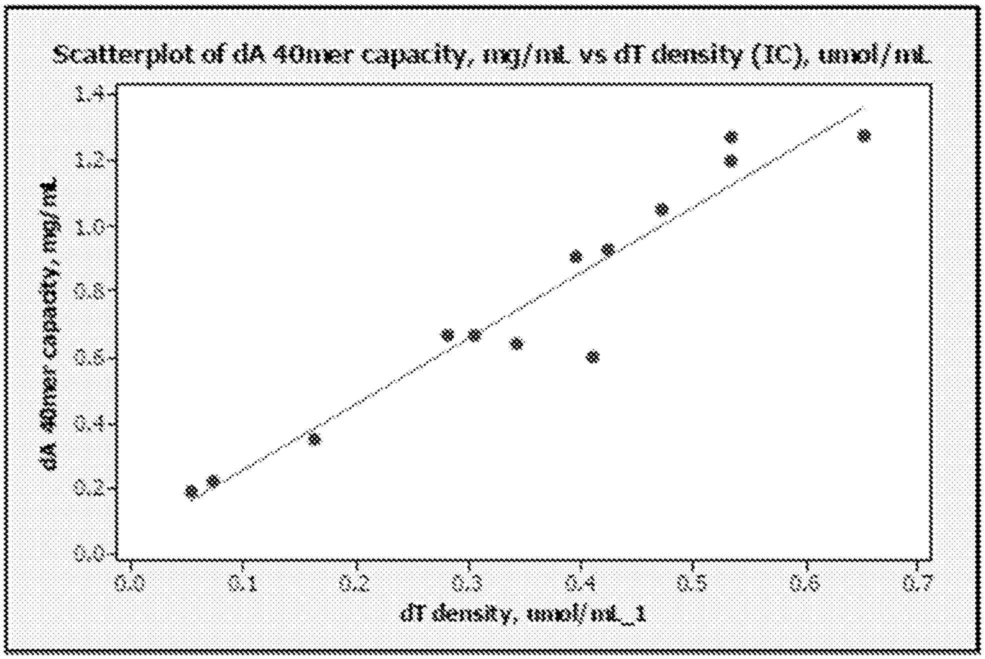
FIG. 16A and FIG. 16B are scatterplots that demonstrate the on-bead densities from ionic capacity values and 40mer dA binding capacity values fit a linear relationship. The increase of coupled dT on bead surface increases the 40mer dA binding capacity. The dT density and dT activity demonstrate that a higher coupled dT density causes a lower activity of coupled dT ligand.
Figure 16B:
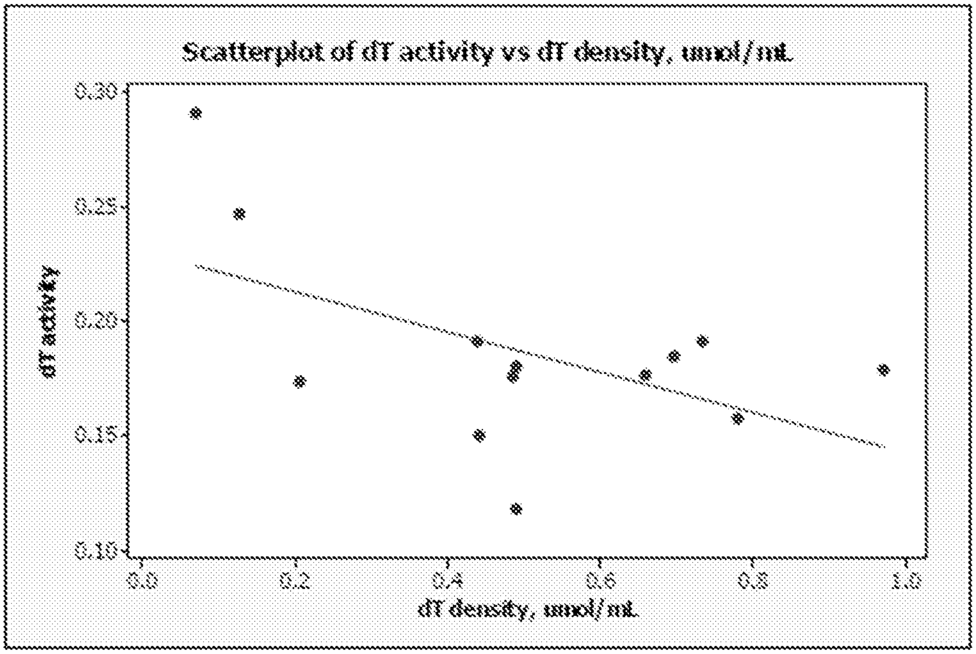

Results of the study predicted that the activity of the conjugate EP 450 will decline about 11% after 18 months of storage at 25° C. in 20% ethanol (FIG. 11A and FIG. 11B).

Example 4—Optimization of Synthesis of Conjugate ("Conjugate EP 450") Using Poros EP 450 Resin, 5' Hexylamine Linker, and 20Mer dT Oligonucleotide Poros EP 450 resin is a porous cross-linked poly(styrene-divinylbenzene) resin activated with an epoxide functionality with a particle size of 45 μm and a pore size of 1000 Å. Poros EP450 was utilized to immobilize a 20mer poly deoxythymidine oligonucleotide ("poly dT oligo") ligand containing a 5' hexylamine linker 5'-$NH_2$—$(CH_2)_6$-TTTTTTTTTTTTTTTTTTTT-3' (SEQ ID NO:1) using the following methods.

Optimization of dT coupling: A 50 mL glass reactor was sterilized with 0.5 M NaOH solution and rinsed with process water. Then 4 mL of EP450 solution was charged into the 50 mL glass reactor. The appropriate amount of formulated ligand solution was charged to the reactor. Then the mixture was shaken at various temperatures and 165 rpm for varying amounts of time (Table 7).

TABLE 7

| Factors | Center | Low | High |
|---|---|---|---|
| dT/resin charge (mg/mL) | 4.5 | 6 | 3 |
| EP 450 resin Slurry (%) | 35 | 30 | 40 |
| Phosphate concentration in formulation solution (M) | 3 | 4 | 2 |
| pH in formulation solution | 9.9 | 10.5 | 9.4 |
| Coupling time (hours) | 38 | 48 | 24 |
| Coupling temperature (° C.) | 45 | 25 | 65 |

After coupling, the sample was washed with 150 mL of 0.1 M sodium phosphate buffer (pH=7.0) on a Nalgene™ Rapid-Flow Sterile Disposable Filter (7×10 mL). 00260 measurements of the filtrate and washings were conducted to evaluate coupling yield. Then the sample was washed with 1 M Tris blocking buffer (2×25 mL). The resins were then mixed with 10 mL 1M Tris blocking buffer for 18 hours at 25° C. Then the sample was washed with 0.1 M Tris buffer (2×10 mL), followed by 0.1 M phosphate buffer (3×10 mL, and then followed by 20% ethanol (3×10 mL). The sample was stored in 20% ethanol at 2-8° C. for further evaluation.

The following samples of conjugate EP 450 in Table 7 were synthesized using the optimized conditions described above, and the ionic capacity and 40mer dA binding capacity of each sample was measured (Table 8, FIG. 12, FIG. 13A, FIG. 13B, FIG. 14, FIG. 15A, FIG. 15B, FIG. 16A, and FIG. 16B).

TABLE 8

| Sample No. | 20mer poly dT oligo/EP 450 resin ratio (mg/mL) | Slurry (%) | Phosphate concentration (M) | pH of coupling reaction | Time (hours) | Temperature (° C.) |
|---|---|---|---|---|---|---|
| 8-1 | 3 | 0.4 | 2 | 9.4 | 24 | 65 |
| 8-2 | 3 | 0.3 | 4 | 10.5 | 72 | 25 |
| 8-3 | 3 | 0.3 | 2 | 9.4 | 24 | 25 |
| 8-4 | 3 | 0.4 | 4 | 9.4 | 72 | 25 |
| 8-5 | 3 | 0.3 | 2 | 10.5 | 72 | 65 |
| 8-6 | 6 | 0.4 | 2 | 10.5 | 24 | 25 |
| 8-7 | 6 | 0.3 | 4 | 9.4 | 24 | 25 |
| 8-8 | 6 | 0.4 | 2 | 10.5 | 72 | 25 |
| 8-9 | 4.5 | 0.35 | 3 | 9.95 | 48 | 45 |
| 8-10 | 6 | 0.3 | 2 | 9.4 | 72 | 65 |
| 8-11 | 6 | 0.3 | 4 | 10.5 | 24 | 65 |
| 8-12 | 3 | 0.4 | 4 | 10.5 | 24 | 65 |
| 8-13 | 6 | 0.4 | 4 | 9.4 | 72 | 65 |
| 8-14 | 5 | 0.4 | 3 | 9.9 | 48 | 25 |

Results: Sample No. 8-1 (dT/resin charge of 3 mg/mL) maintained about 90% of 40mer dA binding capacity. Sample No. 8-9 (dT/resin charge of 4.5 mg/mL) immobilized at 45° C. and had about 30% higher 40mer dA binding capacity.

Example 5—Varying Particle Size and Pore Mode of Resin

Figure 17:
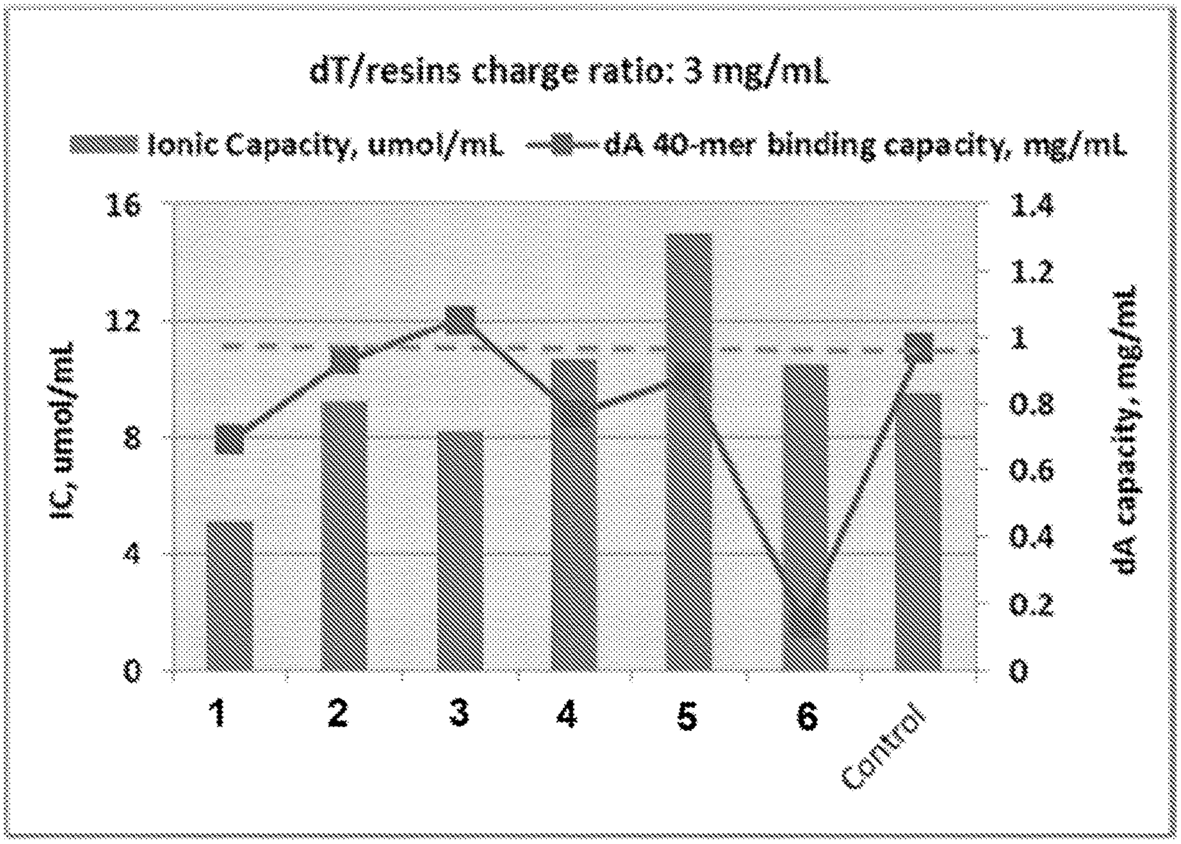
FIG. 17 is a graph depicting the ionic capacity and dA 40mer binding capacity of sample R1, R2, R3, R4, R5, and R6 (Table 11). Sample No. 1 (base bead: OH150) exhibited the lowest ionic capacity and dA 40mer binding capacity, likely due to its lower specific area. Resins with smaller pore modes/sizes (e.g., sample 4, sample 5, and sample 6) showed higher ionic capacity values but their dA 40mer binding capacity values were lower. Sample 6 (with the smallest pore mode/size of 100 Å) showed the lowest dA 40mer binding capacity, likely due to the limited access of dA molecules to the smaller pores. Sample No. 3 (base bead: OH550) exhibited the highest dA 40mer binding capacity among conjugates synthesized using Condition 1.
Figure 18:
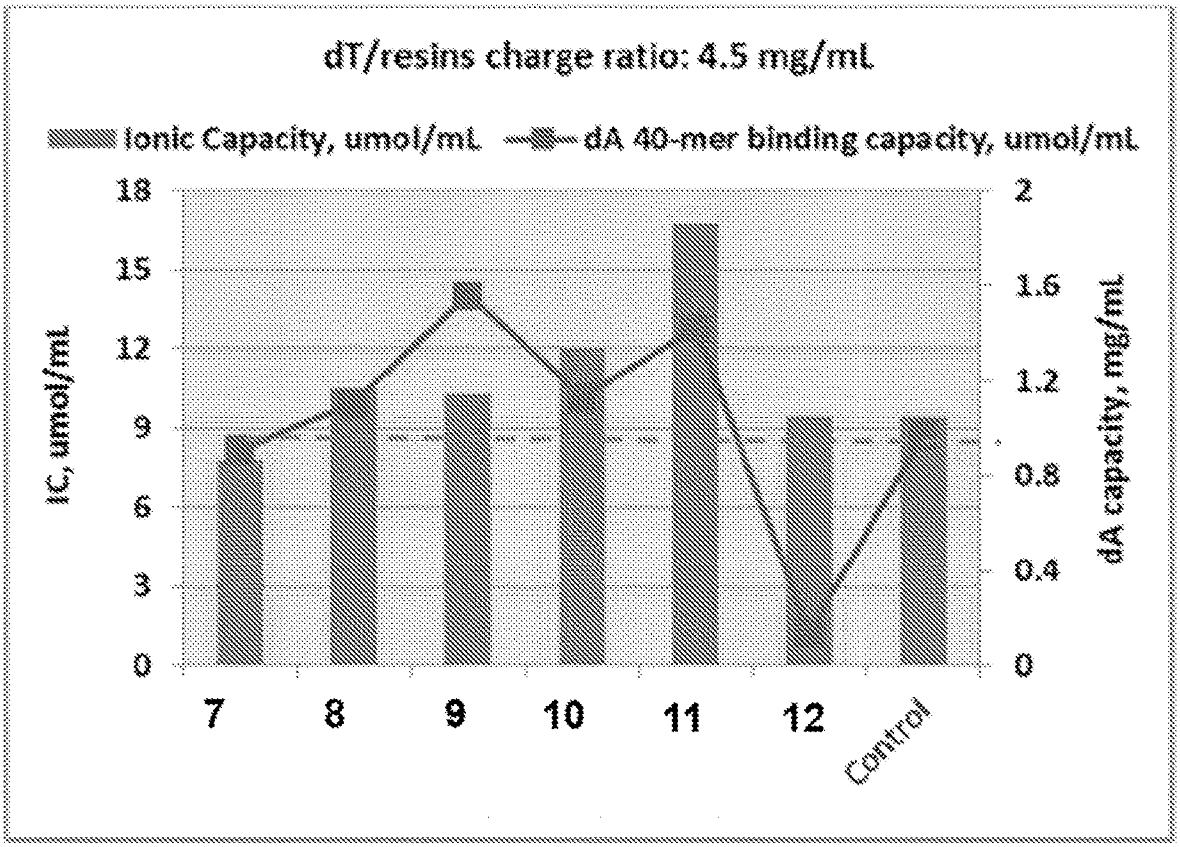
FIG. 18 is a graph depicting the ionic capacity and dA 40mer binding capacity of sample nos. 7-12 (Table 11). Sample No. 7 (base bead: OH150) showed the lowest ionic capacity and dA 40mer binding capacity, likely due to its lower specific area. Resins with smaller pore modes/sizes (e.g., sample 10 and sample 11) showed both higher ionic capacity and dA 40mer binding capacity values. However, sample 12 (with the smallest pore mode/size of 100 Å) showed the lowest dA 40mer binding capacity. Sample 9 (base bead: OH550) exhibited the highest dA 40mer binding capacity among conjugates synthesized using Condition 2.

EP resins with different particle sizes and pore modes (i.e., sizes) can be synthesized under defined coupling conditions. EP resins R1, R2, R3, R4, R5, and R6 (Table 9) were subjected to the following three coupling conditions (Table 10) with 20mer poly deoxythymidine oligonucleotide to evaluate the impact of resin morphologies on their oligonucleotide dT couplings and subsequent dA 40mer binding performances. The ionic capacity, dA 40mer binding capacity, and mean particle size of each resin R1, R2, R3, R4, R5, and R6 subjected to Conditions 1-3 (Table 10) are shown in the table below in Table 11 and in FIG. 17 and FIG. 18. Resin R1 is the base bead for EP150, and resin R2 is the base bead for EP450. Condition 1 is used to generate EP150, and condition 2 is used to generate EP450.

TABLE 9

| Resin No.* | Pore size (Å) | Particle size (μm) |
|---|---|---|
| R1 | 2000 | 50.0 |
| R2 | 1000 | 40.0 |
| R3 | 1200 | 50.0 |
| R4 | 400 | 40.0 |
| R5 | 300 | 30.0 |
| R6 | 100 | 35.0 |

*All resins carry epoxy functions on surfaces with epoxy density of about 20-30 μmol/mL.

TABLE 10

| | dT/resin charge (mg/mL) | Slurry (%) | Phosphate concentration (M) | pH | Time (hours) | Temperature (° C.) |
|---|---|---|---|---|---|---|
| Condition 1 | 3 | 40 | 2 | 9.4 | 24 | 65 |
| Condition 2 | 4.5 | 35 | 3 | 9.9 | 40 | 45 |
| Condition 3 | 5 | 40 | 3 | 9.9 | 48 | 25 |

TABLE 11

| Sample No. | Resin No. | Condition No. | Ionic Capacity (μmol/mL) | dA 40mer binding capacity (mg/mL) | Mean Particle Size (μm) | Particle Size S.D. (μm) | Particle Size (N < 20 μm, %) |
|---|---|---|---|---|---|---|---|
| 1 | R1 | Condition 1 | 5.1 | 0.69 | 51.6 | 11.8 | 10.7 |
| 2 | R2 | Condition 1 | 9.2 | 0.93 | 43.7 | 7.7 | 7.8 |
| 3 | R3 | Condition 1 | 8.2 | 1.05 | 50.3 | 13.3 | 7.5 |
| 4 | R4 | Condition 1 | 10.7 | 0.77 | 47.1 | 10.4 | 11.1 |
| 5 | R5 | Condition 1 | 15 | 0.88 | 36.2 | 4.5 | 7.3 |
| 6 | R6 | Condition 1 | 10.5 | 0.14 | 50.8 | 11.0 | 7.1 |
| 7 | R1 | Condition 2 | 7.8 | 0.91 | 49.9 | 11.5 | 8.3 |
| 8 | R2 | Condition 2 | 10.5 | 1.11 | 38.2 | 9.4 | 6.8 |
| 9 | R3 | Condition 2 | 10.3 | 1.56 | 50.5 | 11.0 | 7.6 |
| 10 | R4 | Condition 2 | 12 | 1.13 | 44.2 | 11.4 | 10.2 |
| 11 | R5 | Condition 2 | 16.8 | 1.42 | 35.5 | 2.3 | 4.9 |
| 12 | R6 | Condition 2 | 9.5 | 0.14 | 49.8 | 10.3 | 8.5 |
| 13 | R1 | Condition 3 | 6.7 | 0.79 | 51.1 | 11.1 | 8.5 |
| 14 | R2 | Condition 3 | 9.5 | 0.97 | 42.7 | 8.2 | 11.1 |

EP 450 resin (sample No. 14) showed consistent ionic capacity and dA 40mer binding capacity values under the three coupling conditions described in Table 10. Sample No. 11-1 and sample No. 11-7 showed lower ionic binding capacity and dA 40mer binding capacity values, likely due to their larger pore mode and lower surface area. Samples with pore mode at 100 Å showed the lowest dA 40mer binding capacity values, likely due to the limited access of dA 40mer oligonucleotides to the small pores. Sample No. 3 and sample No. 9 demonstrated the highest dA binding capacity values.

Example 6—Evaluation by Size Exclusion with mRNA of Different Lengths

Figure 19:
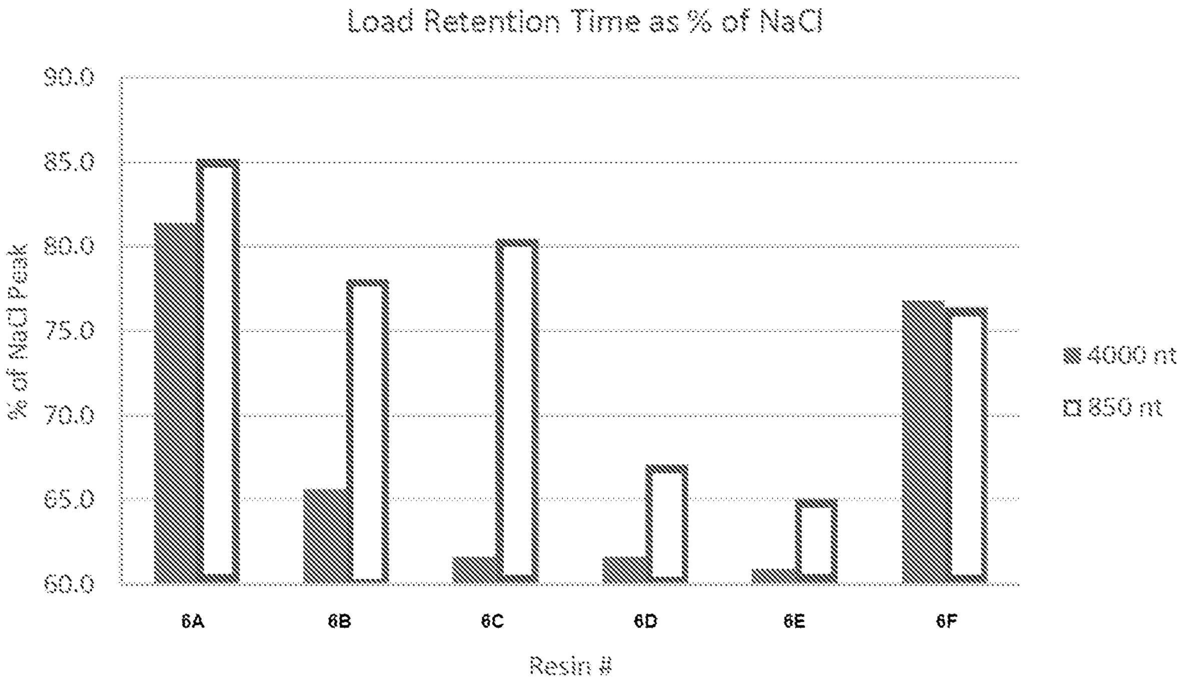
FIG. 19 illustrates the load retention times for the 850 nt and 4000 nt for each resin in Table 12.

Underivatized resins: Underivatized hydrophilized resins were packed into 2 mL columns and tested in a size exclusion mode with two model mRNAs (4,000 nt and 850 nt). The pore size and particle size of each resin is shown in Table 12 below. The load retention time as percentage of sodium chloride is shown in FIG. 19.

TABLE 12

| Resin Sample No. | Pore size (Å) | Particle size (μm) |
|---|---|---|
| 6A | 2000 | 50 |
| 6B | 1000 | 40 |
| 6C | 1200 | 50 |
| 6D | 400 | 40 |
| 6E | 300 | 30 |
| 6F | 100 | 35 |

Retention time of a 100 μL pulse was compared to that of salt. Larger pore size correlated with higher retention times, suggesting that mRNA partially diffuses into the pores.

Derivatized resins: The resin slurry (50 μL/well) was dispensed into 96-well 2 mL fritted plate (Seahorse BioScience, 25 μm PE frit) equilibrated with the loading buffer. 4000 nt mRNA and 850 nt mRNA were concentrated using 30K Centricons and formulated in the loading buffer into a 12-column reservoir according to Table 13 below.

TABLE 13

| | mRNA Stock Solution No. | LC (mg/mL) | C load (mg/mL) | V RNA (µL) | V LSW (µL) | V Water (µL) |
|---|---|---|---|---|---|---|
| 850 nt | 850-1 | 1 | 0.25 | 124.1 | 800.0 | 3075.9 |
| mRNA | 850-2 | 2 | 0.5 | 248.1 | 800.0 | 2951.9 |
| stock | 850-3 | 4 | 1 | 496.3 | 800.0 | 2703.7 |
| (mg/mL) | 850-4 | 6 | 1.5 | 744.4 | 800.0 | 2455.6 |
| 8.06 | 850-5 | 8 | 2 | 992.6 | 800.0 | 2207.4 |
| | 850-6 | 10 | 2.5 | 1240.7 | 800.0 | 1959.3 |
| 4000 nt | 4000-7 | 1 | 0.25 | 211.9 | 800.0 | 2988.1 |
| mRNA | 4000-8 | 2 | 0.5 | 423.7 | 800.0 | 2776.3 |
| stock | 4000-9 | 4 | 1 | 847.5 | 800.0 | 2352.5 |
| (mg/mL) | 4000-10 | 6 | 1.5 | 1271.2 | 800.0 | 1928.8 |
| 4.72 | 4000-11 | 8 | 2 | 1694.9 | 800.0 | 1505.1 |
| | 4000-12 | 10 | 2.5 | 2118.6 | 800.0 | 1081.4 |

Loaded 200 µL of adjusted loads/well and incubated on a shaking platform set at 1000 rpm for 20 minutes at ambient temperature (22° C.). Spun the plate at 1000 rpm for 2 minutes and collected the flow-through. The concentration of the flow-through corresponds to the free concentration ($C_S$), while the bound concentration ($C_R$) is calculated as: $C_R$=2000*($C_{Load}$–$C_S$)/50. The plate was eluted with 300 µL/well of the elution buffer heated to 70° C. The equilibrium mRNA concentration in the filtrate $C_S$ (mg/mL) was measured by UV and is shown in Table 14A (850 nt mRNA) and Table 14B (4000 nt mRNA) below.

TABLE 14A

| Sample No. | Resin Pore Size (Å) | Bead diameter (µm) | C load (mg/mL) of 850 nt mRNA 0.25 | 0.5 | 1 | 1.5 | 2 | 2.5 |
|---|---|---|---|---|---|---|---|---|
| 1 | 2000 | 50 | 0.001 | 0.004 | 0.081 | 0.415 | 0.758 | 1.119 |
| 2 | 1000 | 40 | 0.004 | 0.008 | 0.071 | 0.301 | 0.705 | 0.957 |
| 3 | 1200 | 50 | 0.002 | 0.005 | 0.064 | 0.328 | 0.642 | 0.969 |
| 4 | 400 | 40 | 0.019 | 0.093 | 0.366 | 0.750 | 1.079 | 1.426 |
| 5 | 300 | 30 | 0.042 | 0.145 | 0.448 | 0.837 | 1.163 | 1.523 |
| 6 | 100 | 35 | 0.226 | 0.463 | 0.907 | 1.333 | 1.694 | 2.104 |
| 7 | 2000 | 50 | 0.001 | 0.009 | 0.098 | 0.392 | 0.689 | 1.031 |
| 8 | 1000 | 40 | 0.002 | 0.020 | 0.054 | 0.211 | 0.466 | 0.789 |
| 9 | 1200 | 50 | 0.002 | 0.006 | 0.049 | 0.267 | 0.566 | 0.894 |
| 10 | 400 | 40 | 0.021 | 0.100 | 0.340 | 0.682 | 1.045 | 1.356 |
| 11 | 300 | 30 | 0.050 | 0.170 | 0.498 | 0.901 | 1.249 | 1.600 |
| 12 | 100 | 35 | 0.205 | 0.428 | 0.862 | 1.331 | 1.733 | 2.117 |
| 13 | 2000 | 50 | 0.002 | 0.007 | 0.089 | 0.379 | 0.684 | 1.021 |
| 14 | 1000 | 40 | 0.002 | 0.008 | 0.046 | 0.174 | 0.412 | 0.734 |
| 15 (Control: Resin 6B) | 1000 | 40 | 0.212 | 0.329 | 0.796 | 1.221 | 1.605 | 2.003 |
| 16 (Control: Resin 6F) | 100 | 35 | 0.206 | 0.430 | 0.781 | 1.282 | 1.621 | 1.998 |

TABLE 14B

| Resin Sample No. | Pore Size (Å) | Bead diameter (µm) | C load (mg/mL) of 4000 nt mRNA 0.25 | 0.5 | 1 | 1.5 | 2 |
|---|---|---|---|---|---|---|---|
| 1 | 2000 | 50 | 0.010 | 0.069 | 0.307 | 0.647 | 1.030 |
| 2 | 1000 | 40 | 0.057 | 0.183 | 0.485 | 0.777 | 1.138 |
| 3 | 1200 | 50 | 0.019 | 0.091 | 0.328 | 0.617 | 0.996 |
| 4 | 400 | 40 | 0.143 | 0.333 | 0.734 | 1.143 | 1.588 |
| 5 | 300 | 30 | 0.175 | 0.392 | 0.804 | 1.199 | 1.591 |
| 6 | 100 | 35 | 0.209 | 0.442 | 0.884 | 1.283 | 1.673 |
| 7 | 2000 | 50 | 0.013 | 0.083 | 0.345 | 0.680 | 1.024 |
| 8 | 1000 | 40 | 0.055 | 0.191 | 0.473 | 0.783 | 1.102 |
| 9 | 1200 | 50 | 0.021 | 0.100 | 0.334 | 0.604 | 0.955 |

TABLE 14B-continued

| Resin Sample No. | Pore Size (Å) | Bead diameter (µm) | C load (mg/mL) of 4000 nt mRNA 0.25 | 0.5 | 1 | 1.5 | 2 |
|---|---|---|---|---|---|---|---|
| 10 | 400 | 40 | 0.156 | 0.370 | 0.809 | 1.188 | 1.602 |
| 11 | 300 | 30 | 0.189 | 0.422 | 0.873 | 1.266 | 1.716 |
| 12 | 100 | 35 | 0.214 | 0.457 | 0.924 | 1.347 | 1.743 |
| 13 | 2000 | 50 | 0.017 | 0.094 | 0.375 | 0.708 | 1.072 |
| 14 | 1000 | 40 | 0.072 | 0.226 | 0.569 | 0.877 | 1.206 |

TABLE 14B-continued

| Resin Sample No. | Pore Size (Å) | Bead diameter (µm) | C load (mg/mL) of 4000 nt mRNA 0.25 | 0.5 | 1 | 1.5 | 2 |
|---|---|---|---|---|---|---|---|
| 15 (Control: Resin 6B) | 1000 | 40 | 0.226 | 0.445 | 0.928 | 1.315 | 1.677 |
| 16 (Control: Resin 6F) | 100 | 35 | 0.227 | 0.477 | 0.921 | 1.303 | 1.712 |

Figure 20A:
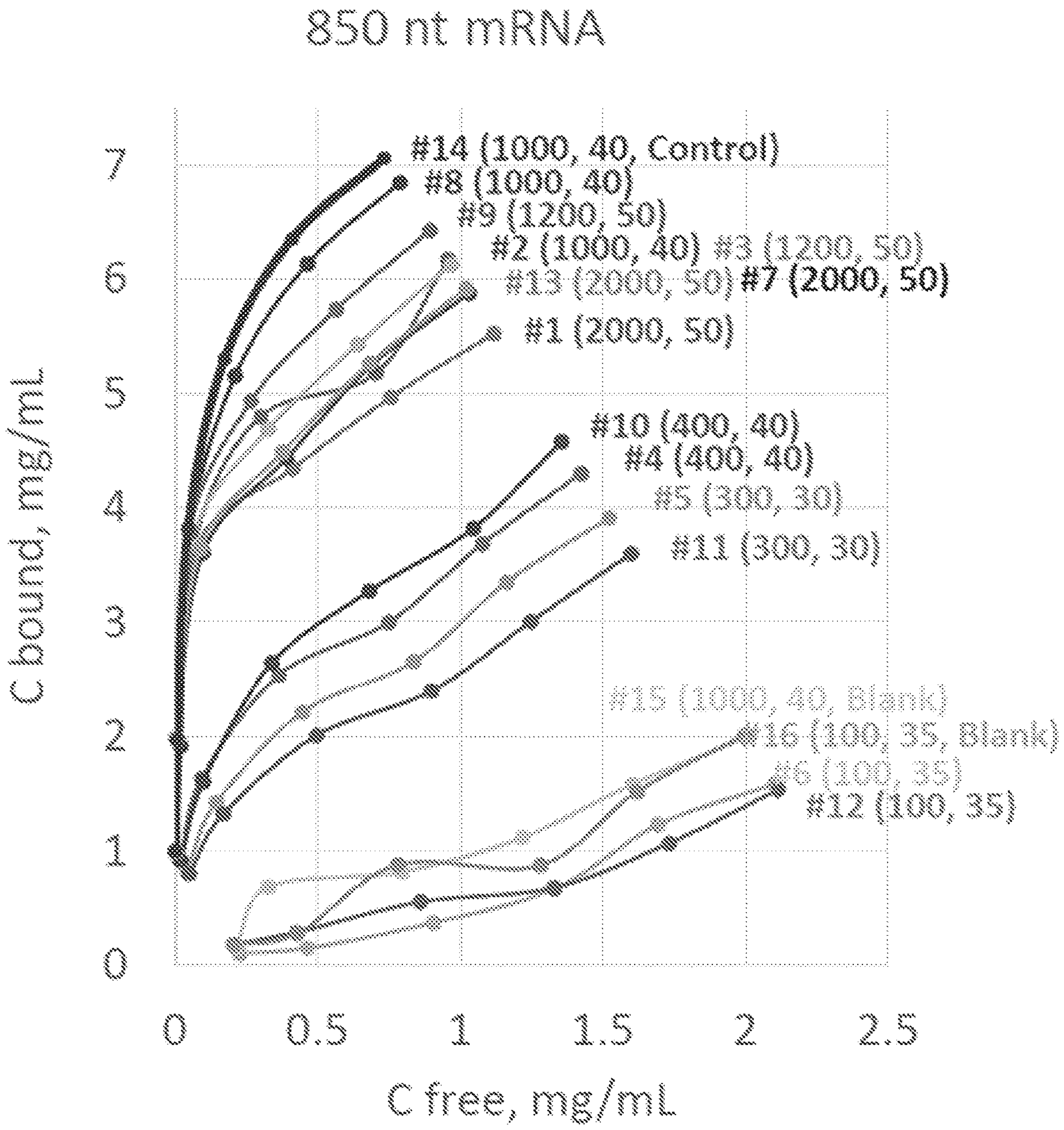
FIG. 20A and FIG. 20B illustrate the calculated bound concentrations ($C_S$) for the 850 nt mRNA (FIG. 20A) and 4000 nt mRNA (FIG. 20B) from the load concentrations ($C_{Load}$) and measured free concentration ($C_S$) shown in Table 14A and Table 14B.
Figure 20B:
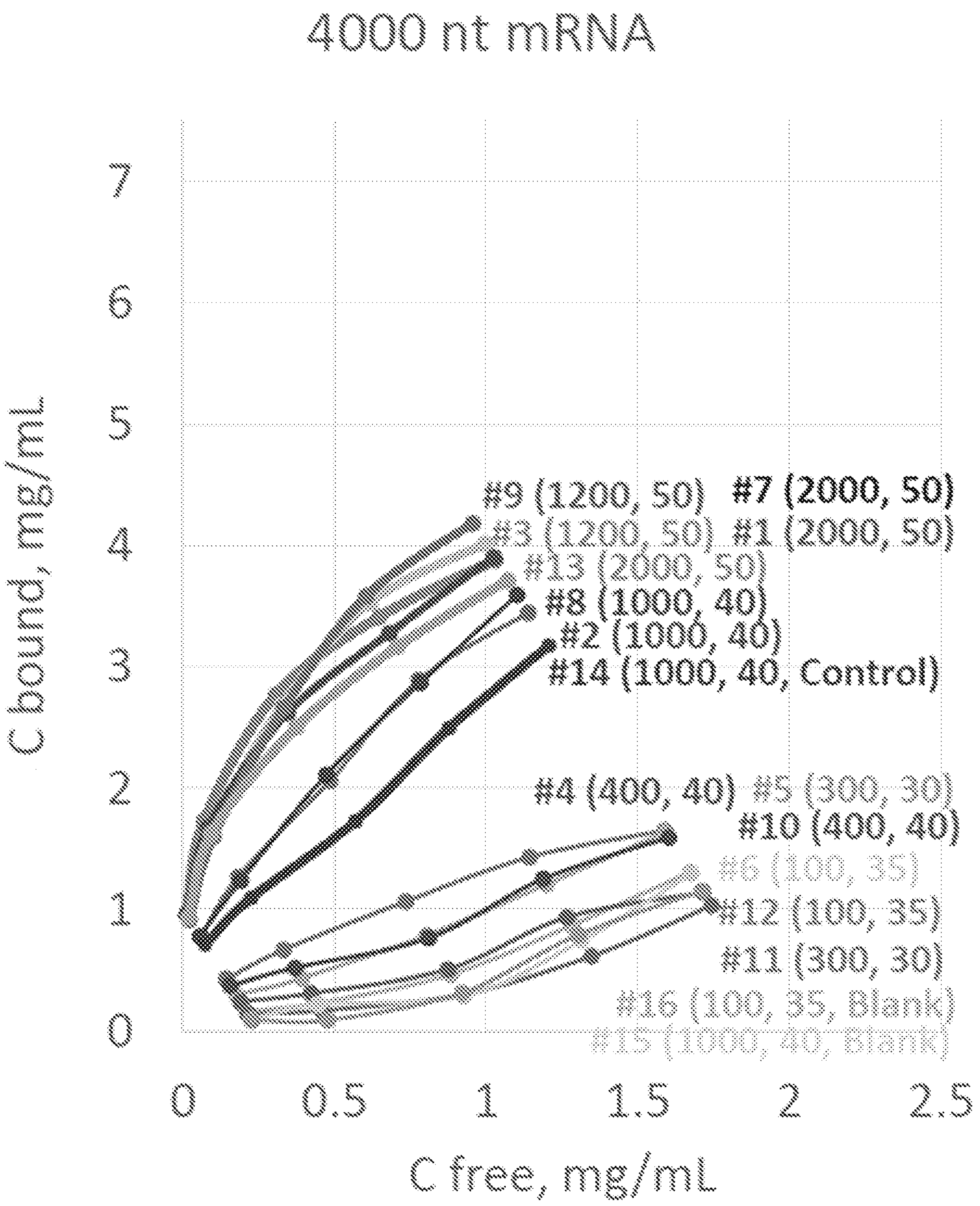

The calculated bound concentrations for the 850 nt mRNA and 4000 nt mRNA are shown in FIG. 20A and FIG.

Figure 21A:
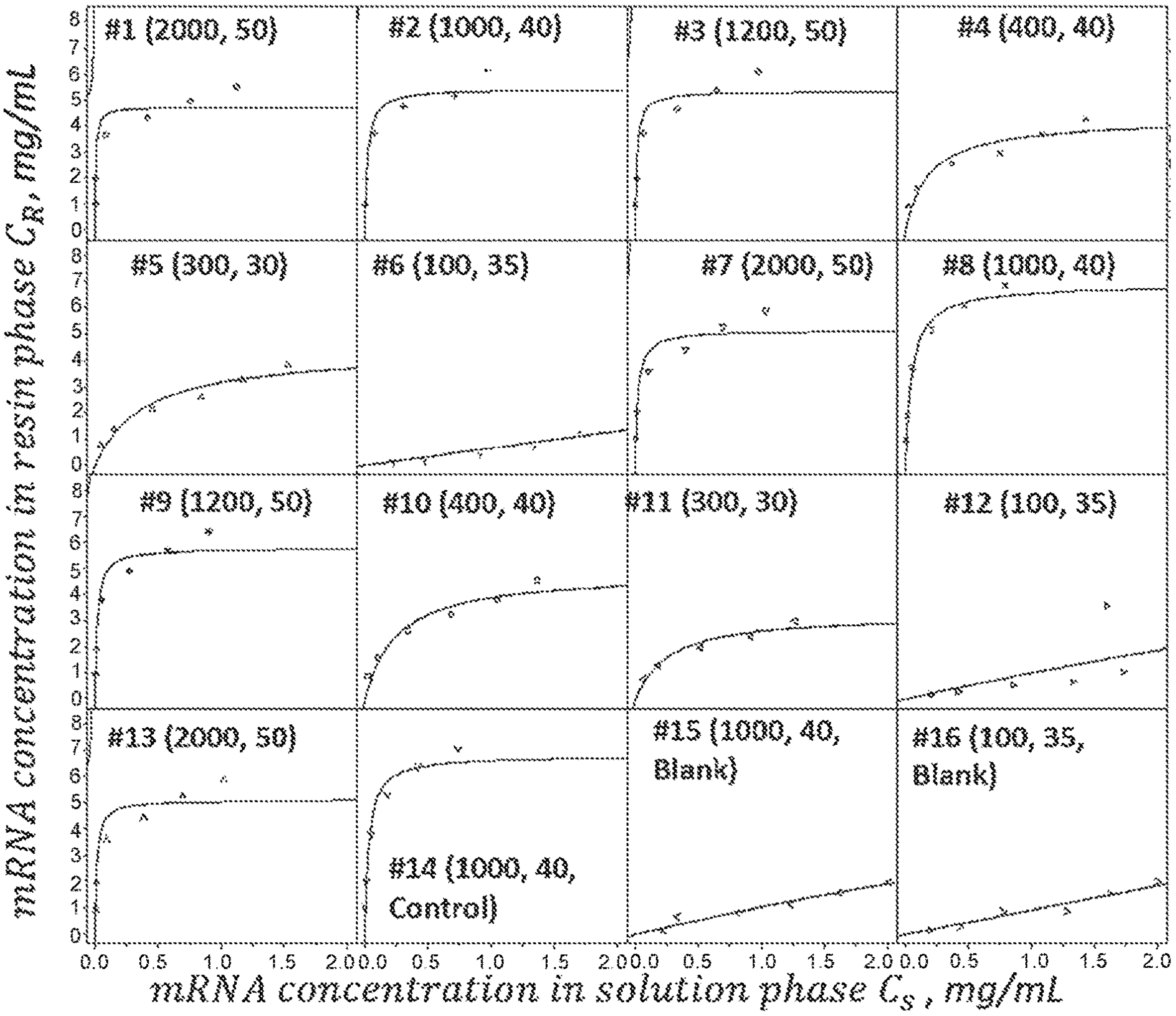
FIG. 21A and FIG. 21B illustrate the Langmuir model fit for the calculated dissociation constant ($K_d$) and max binding capacity ($Q_m$) for the 850 nt mRNA and 4000 nt mRNA to each of the resin samples.
Figure 21B:
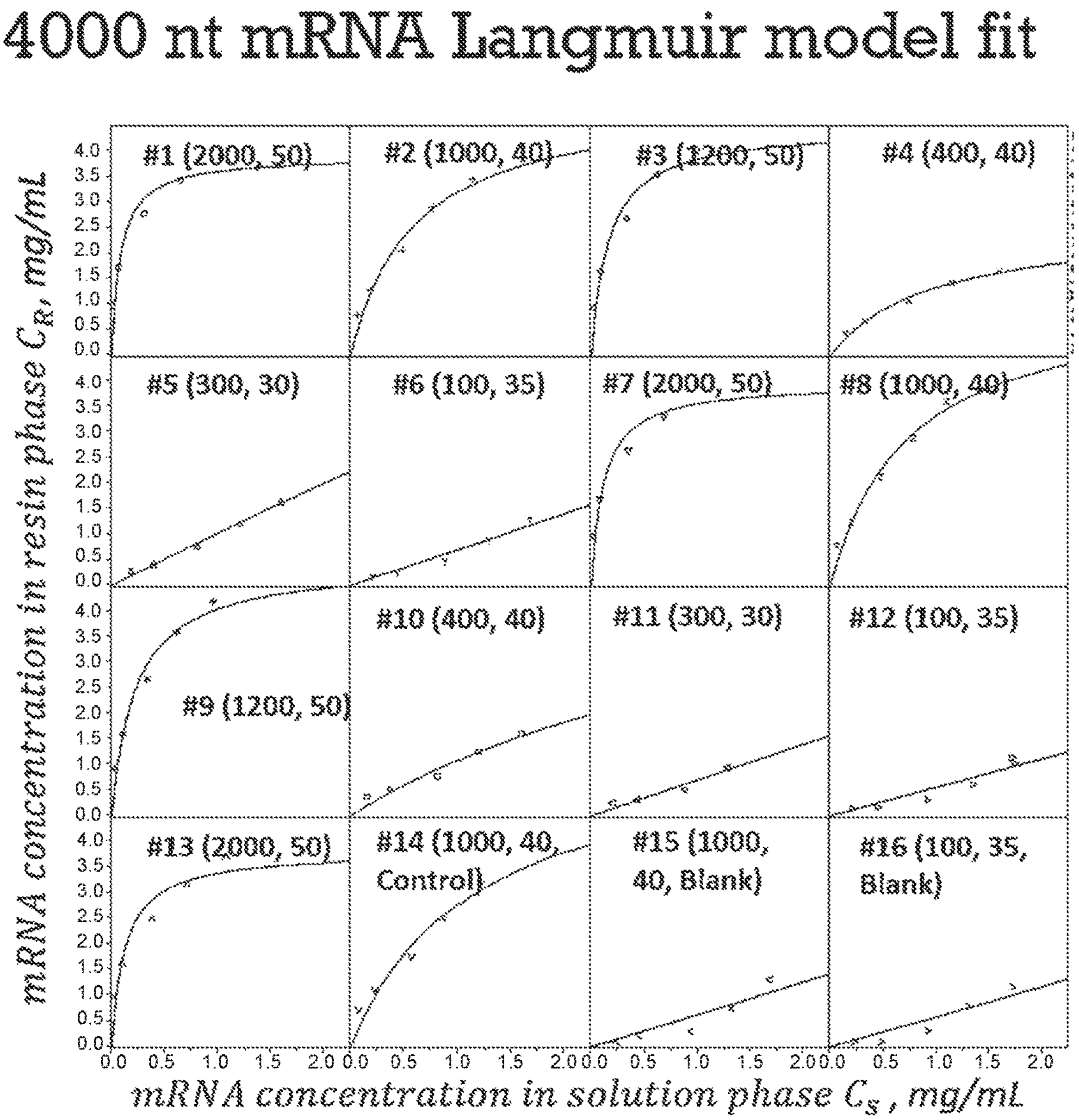

20B. The dissociation constant ($K_d$) and max binding capacity ($Q_m$) for the 850 nt mRNA and 4000 nt mRNA with the conjugate samples were calculated using Langmuir model fit (FIG. 21A and FIG. 21B) and are shown in Table 15A (850 nt mRNA) and Table 15B (4000 nt mRNA) below.

TABLE 15A

| Sample No. | $Q_m$, (mg/mL) | $K_d$, (mg/mL) |
|---|---|---|
| 1 | 4.8 | 0.01 |
| 2 | 5.5 | 0.02 |
| 3 | 5.4 | 0.01 |
| 4 | 4.3 | 0.19 |
| 5 | 4.5 | 0.39 |
| 6 | | |
| 7 | 5.2 | 0.02 |
| 8 | 6.9 | 0.05 |
| 9 | 5.8 | 0.02 |
| 10 | 4.9 | 0.24 |
| 11 | 3.3 | 0.25 |
| 12 | | |
| 13 | 5.1 | 0.01 |
| 14 | 6.8 | 0.03 |

TABLE 15B

| Sample No. | $Q_m$, (mg/mL) | $K_d$, (mg/mL) |
|---|---|---|
| 1 | 3.9 | 0.8 |
| 2 | 5.1 | 0.59 |
| 3 | 4.5 | 0.16 |
| 4 | 2.6 | 0.95 |
| 5 | | |
| 6 | | |
| 7 | 3.9 | 0.11 |
| 8 | 5.7 | 0.72 |
| 9 | 4.9 | 0.22 |
| 10 | 5.9 | 4.42 |
| 11 | | |
| 12 | | |
| 13 | 3.8 | 0.12 |
| 14 | 6.0 | 1.17 |

Figure 22A:
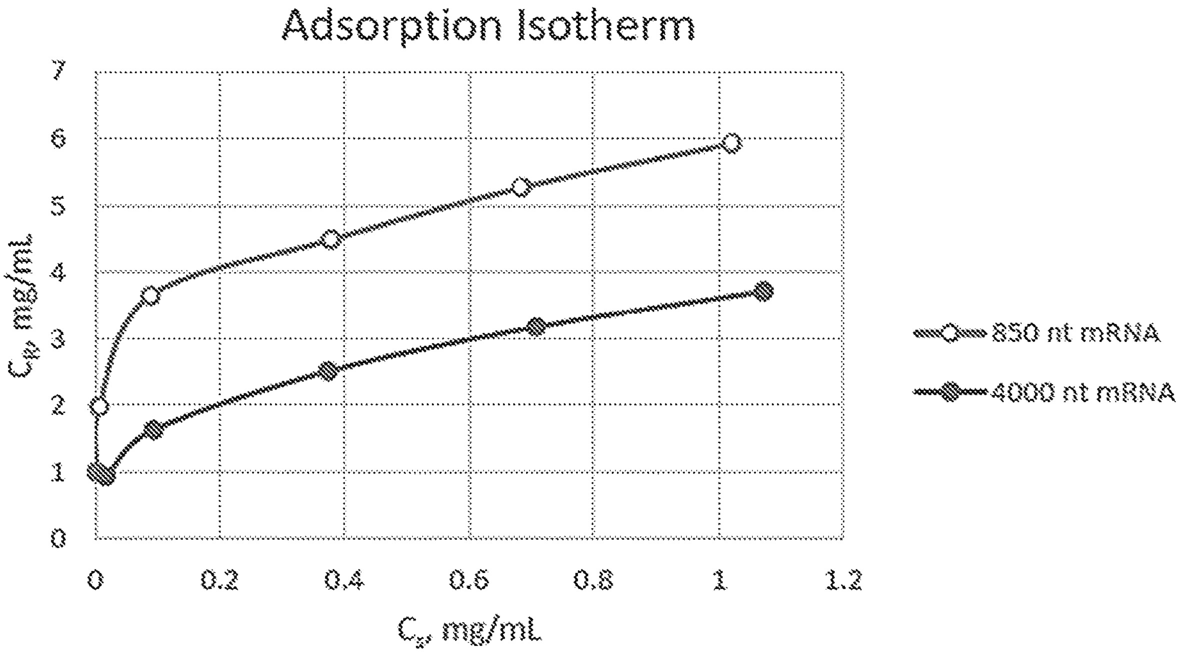
FIG. 22A and FIG. 22B illustrate the adsorption isotherm and double-reciprocal plot (application of Lineweaver-Burk double-reciprocal equation) for Resin Sample No. 13.
Figure 22B:
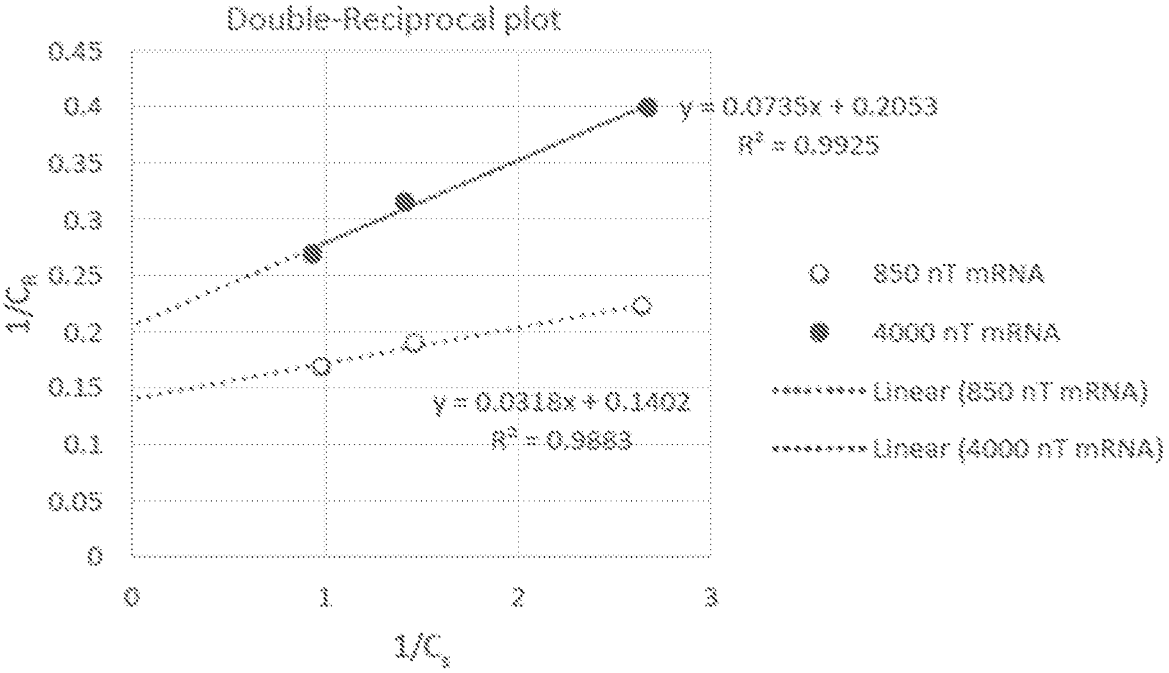

The adsorption isotherm for Resin Sample No. 13 (dT charge 5.0 mg/mL) is shown in FIG. 22A. The double-reciprocal plot of Resin Sample No. 13 is shown in FIG. 22B.

A table summarizing the dT/resin charge, ionic capacity, and SBC to dA 40mer oligonucleotide, and the calculated $K_d$ and $Q_m$ values for conjugate samples 1-14 is shown in FIG. 23.

From equilibrium batch-binding experiments, sample 14 performed best with 850 nt mRNA, and sample 3 and sample 9 (50 μm resin/bead particle size and 1200 Å resin/bead pore size), performed better than sample 14 for the 4000 nt mRNA. Column runs showed that DBC for the 4000 nt mRNA correlates with the pore size of the resin/bead.

Figure 24:
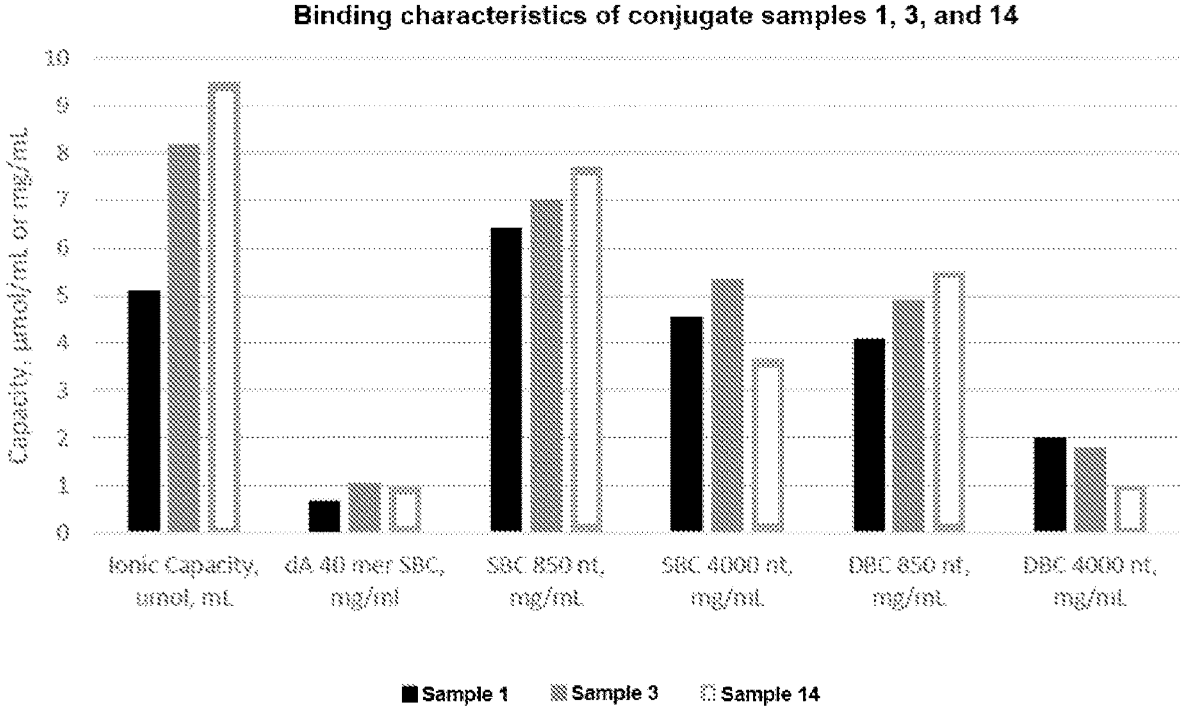
FIG. 24 is a graph illustrating the SBC, DBC, and ionic capacity of sample 1, sample 3, and sample 14 with the 850 nt mRNA and the 4000 nt mRNA.

Samples 1, 3, and 14: The ionic capacity, SBC, and DBC of sample No. 1, sample No. 3, and sample No. 14 for the 850 nt mRNA and the 4000 nt mRNA is shown in FIG. 24 and in Table 16 below.

TABLE 16

| Sample No. | Resin Pore Size (Å) | Ionic Capacity (μmol/mL) | dA 40mer SBC (mg/ml) | 850 nt SBC (mg/mL) | 4000 nt SBC (mg/mL) | 850 nt DBC (mg/mL) | 4000 nt DBC (mg/mL) |
|---|---|---|---|---|---|---|---|
| 1 | 2000 | 5.1 | 0.69 | 6.42 | 4.55 | 4.1 | 2.0 |
| 3 | 1200 | 8.2 | 1.05 | 7.02 | 5.35 | 4.9 | 1.8 |
| 14 | 1000 | 9.5 | 0.97 | 7.72 | 3.66 | 5.5 | 1.0 |

Small pore resins (100-400 Å) have low capacities to mRNA. The size cutoff for 40mer dA oligonucleotide is 100 Å and for mRNA is 400 Å. Resins with pore mode/size of 1000-2000 Å have higher capacity for mRNA. Diffusion of RNA into pores is required for maximizing binding of RNA (e.g., mRNA).

The optimized dT immobilization conditions (3 mg/mL ligand charge; 65° C. coupling temperature) result in resins with lower mRNA binding capacity compared to the control resin. The dynamic binding capacity (DBC) for mRNA with 850 nt correlates with the ionic capacity, but the DBC for mRNA with 4000 nt correlates with the pore size.

Resins with larger pore modes/sizes are useful for purification of a broad spectrum of mRNA. Lower ligand charge for resins OH150 and OH550 with 2000 Å and 1200 Å pores likely does not compromise the capacity for mRNA.

Example 7—Epoxy Density Level, Coupling Kinetics, Coupling Temperature

Procedure: Poros OH150 beads/resins were epoxy functionalized with five levels of base content (NaOH concentrations) to generate EP 150 resins. A concentration of 0.83% NaOH (% w) leads to the highest epoxy level (about 50 μmol/mL). Decreasing base content leads to lower epoxy density. Higher NaOH concentration facilitates the epoxy hydrolysis as a competitive side reaction, which leads to lower functions levels. The base concentration up to 1.5% triggers the crosslinking between b-epoxy molecules in reaction mixture, which causes the failure of epoxy functionalization (FIG. 25).

Figure 25:
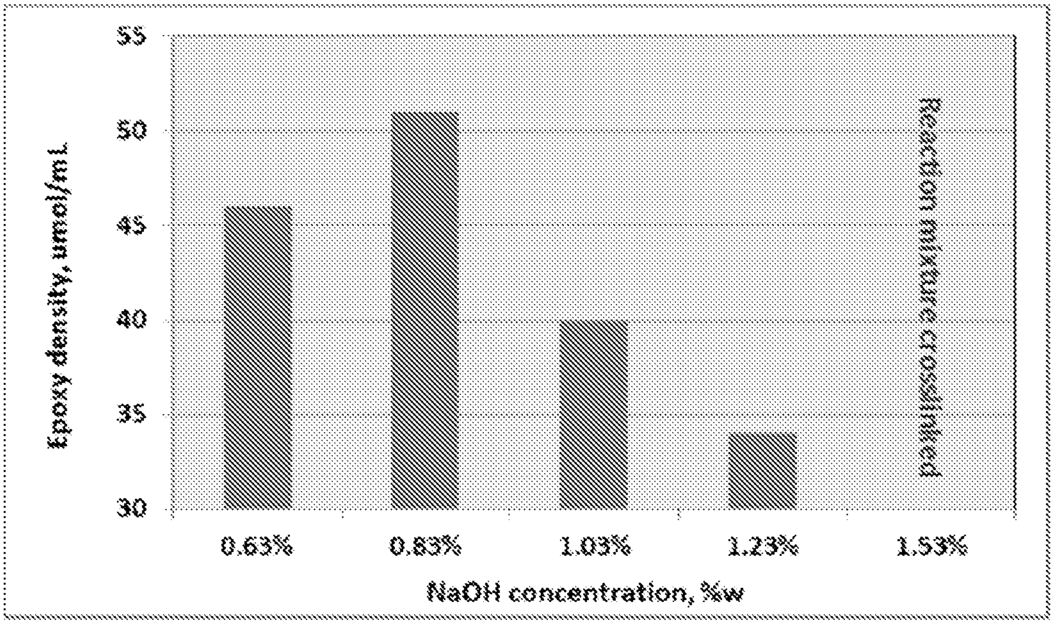
FIG. 25 is a graph illustrating the epoxy density level (μmol/mL) based on the NaOH concentration (% w) of the Poros OH150 resin.

EP 150 resins with four levels of epoxy densities ranging from 34 up to 51 μmol/mL were prepared to examine the effect of epoxy functions on coupling and resin performance (FIG. 25). The four resins were coupled with dT ligands and evaluated through ionic capacity test and 40mer dA HTP assay.

Results: The process for EP150/dT resins was studied by investigating the effect of epoxy density on bead surfaces, coupling kinetics, coupling dT ligand charge and temperature, as well as blocking time. The process tolerance window for epoxy density on bead surfaces was identified from 40 to 52 μmol/mL. This epoxy range can be realized by controlling the base content from 0.6% to 1.0% during the preparation EP 150 beads. The coupling time at 24±2 hours, coupling temperature at 65±2° C., dT/bead charge at 3±0.2 mg/mL and blocking time at 18±3 hours, are determined as the process tolerance windows to prepare EP150/dT resins.

Figure 26:
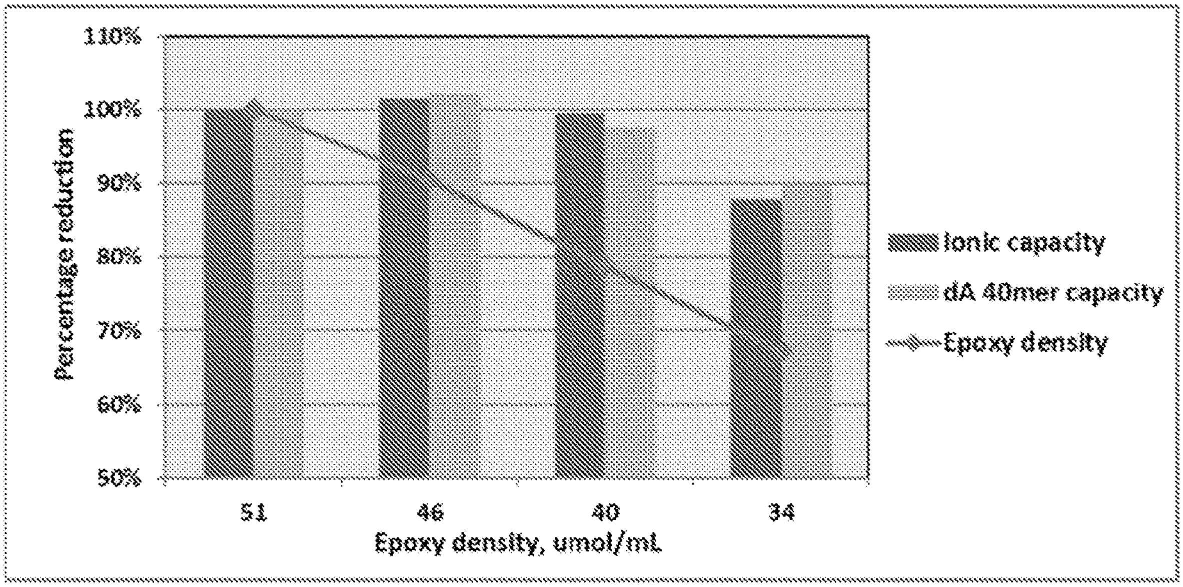
FIG. 26 illustrates the relationship between ionic capacity, and 40mer dA binding capacity with epoxy density.

Epoxy density level: As epoxy density decreases from 51 to 40 μmol/mL, both ionic capacity and 40mer dA binding capacity values remain at the same level (FIG. 26). Decreasing the epoxy density to 34 μmol/mL leads to both ionic capacity and 40mer dA binding capacity values decreasing about 10% (FIG. 26). About 0.5% epoxy functions are used for dT ligand coupling (coupled dT ligand density is <0.3 μmol/mL). An epoxy level higher than 40 μmol/mL is achieved by adjusting the base content to between 0.6% and 1.0%, but this epoxy level higher than 40 μmol/mL will not significantly impact the coupling process and resin performance.

Figure 27:
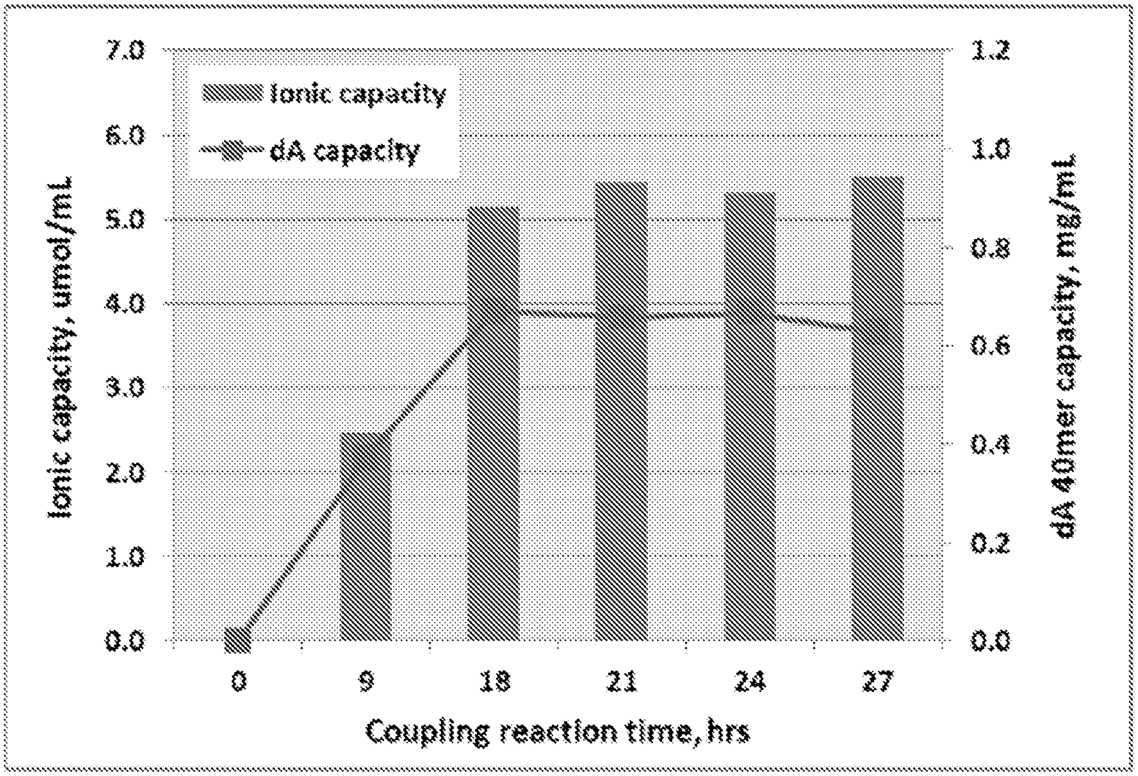
FIG. 27 is a graph illustrating the ionic capacity and 40mer dA binding capacity values over the course of the coupling reaction.

Coupling kinetics: Coupling time of 24±2 hours was used for the preparation of EP 150/dT20 resin. The dT coupling kinetics on EP 150 bead surfaces was studied by evaluating samples 9 hours, 18 hours, 21 hours, 24 hours, and 27 hours after the start of the coupling reaction (FIG. 27). Ionic capacity and 40mer dA binding capacity significantly increased within the first 18 hours of the coupling reaction. Both values reached a plateau between 18-27 hours. There was no impact to resin performance.

Figure 28:
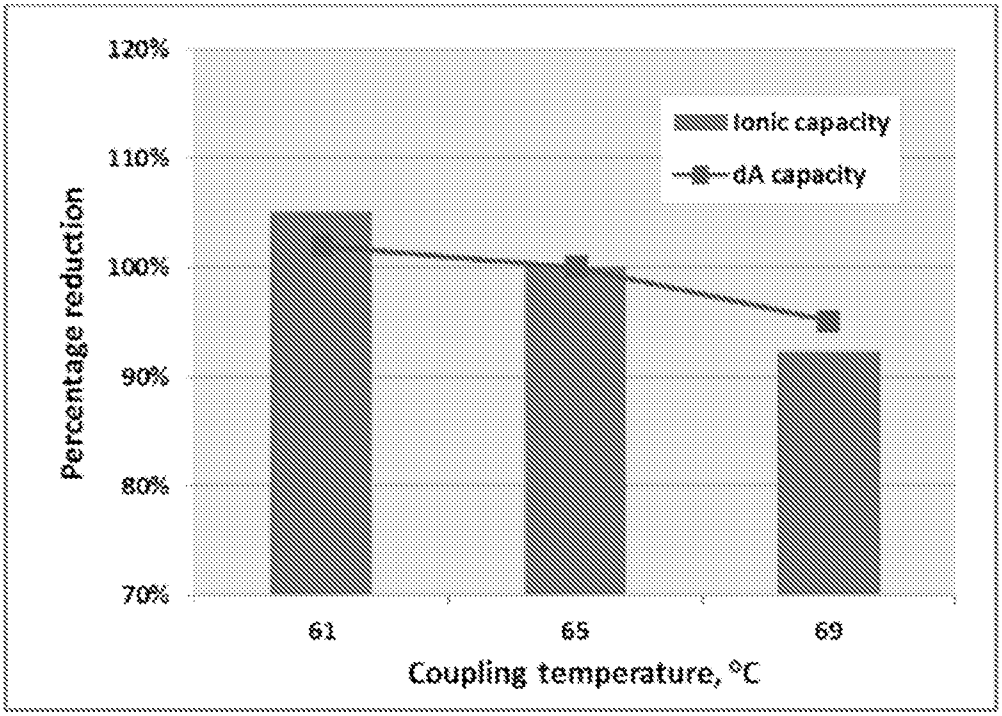
FIG. 28 is a graph illustrating the ionic capacity and 40mer dA binding capacity values at different coupling temperatures.
Figure 29:
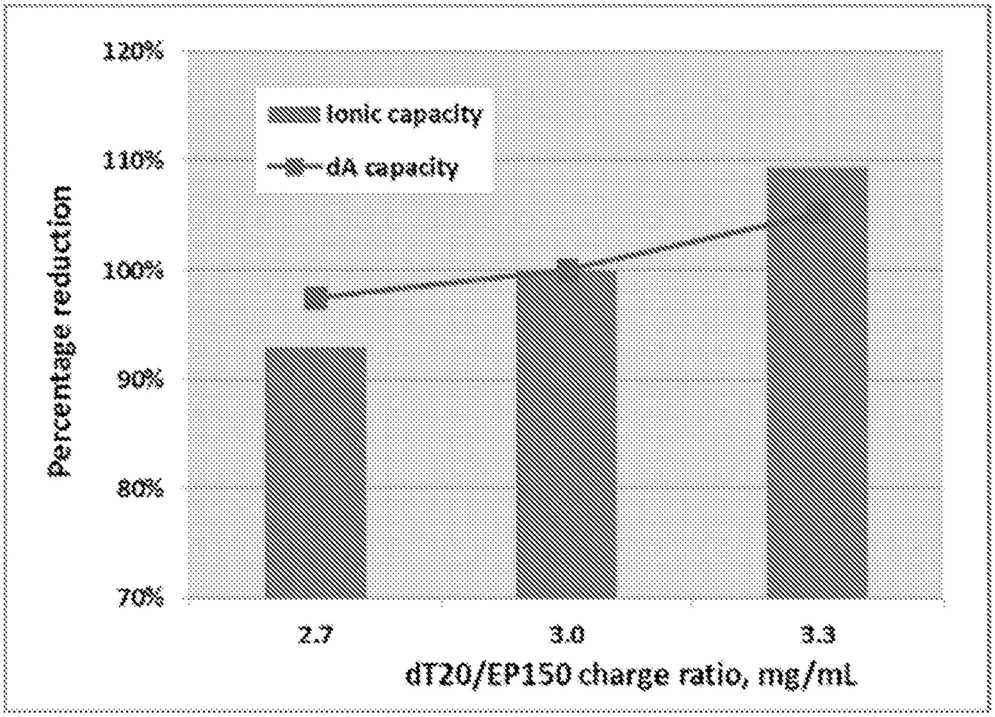
FIG. 29 is a graph illustrating the ionic capacity and 40mer dA binding capacity values at different ligand/bead charges.

Coupling temperatures: Coupling temperature of 65±3° C. was used for the preparation of EP150/dT20 resin. Samples were collected and evaluated at 61° C., 65° C., and 69° C. (FIG. 28).

dT ligand charge: dT ligand/beads charge of 3±0.2 mg/mL was used for the preparation of EP150/dT20 resin. Samples were collected and evaluated at 2.7 mg/mL, 3.0 mg/mL, and 3.3 mg/mL (FIG. 29).

Figure 30:
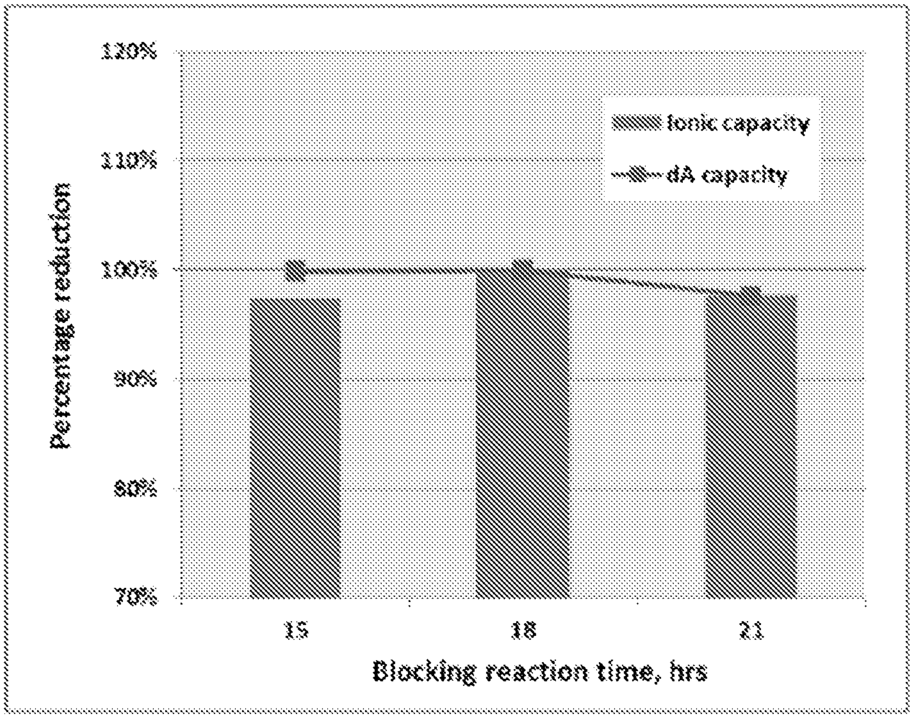
FIG. 30 is a graph illustrating the ionic capacity and 40mer dA binding capacity values at different blocking times.

Blocking time: Blocking time at 18±3 hours was used for the preparation of EP150/dT20 resin. Samples were collected and evaluated at 15 hours, 18 hours, and 21 hours (FIG. 30).

Example 8—Stability Assessment of Conjugate EP 150 (Conjugate 1) and Conjugate EP 450 (Conjugate 2)

Procedure: The stability of conjugate EP 150 and of conjugate EP 450 in 20% ethanol were studied under accelerated conditions (Kennon, L., Use of models determining chemical pharmaceutical stability J. of Pharmaceutical Sciences 5:815-818 (1964)). Accelerated stability samples were stored at 60° C. and control sample was stored at 2-8° C. (Table 17).

TABLE 17

| Test Condition | Predicted storage conditions | |
|---|---|---|
| Storage at 60° C. | Storage at 25° C. | Storage at 5° C. |
| 3 days | 3 months | 34 months |
| 11 days | 12 months | 138 months |
| 16 days | 18 months | 205 months |

The samples were evaluated through 40mer dA oligonucleotide binding capacity via HTP assay and through ionic capacity test. Extensive washing with water and 0.1 M NaCl solution was applied to eliminate any leached dT oligonucleotide ligand.

Results: Ionic capacity test and dA 40mer binding capacity assay showed the same trend for the same prototype with multiple lots, suggesting the data are reliable. Results of dA 40mer binding capacity assay suggests Conjugate 1 can be stored at 5° C. for 45 months to remain 90% of its original activity, indicating the good stability of Conjugate 1 prototypes. Conjugate 2 (new EP450/dT) has very similar stability as Conjugate 2 from a 10 L manufacturing batch.

Base bead type will impact stability. During the evaluated storage period, the reduction of ionic capacity is slower than dA binding capacity for all three resins. This indicates, although coupled dT ligand remains on resin surfaces, some original activity may be lost after a long storage period. Therefore, it may be valuable to further investigate and define a better storage solution for Poros Oligo dT resins.

Figure 31A:
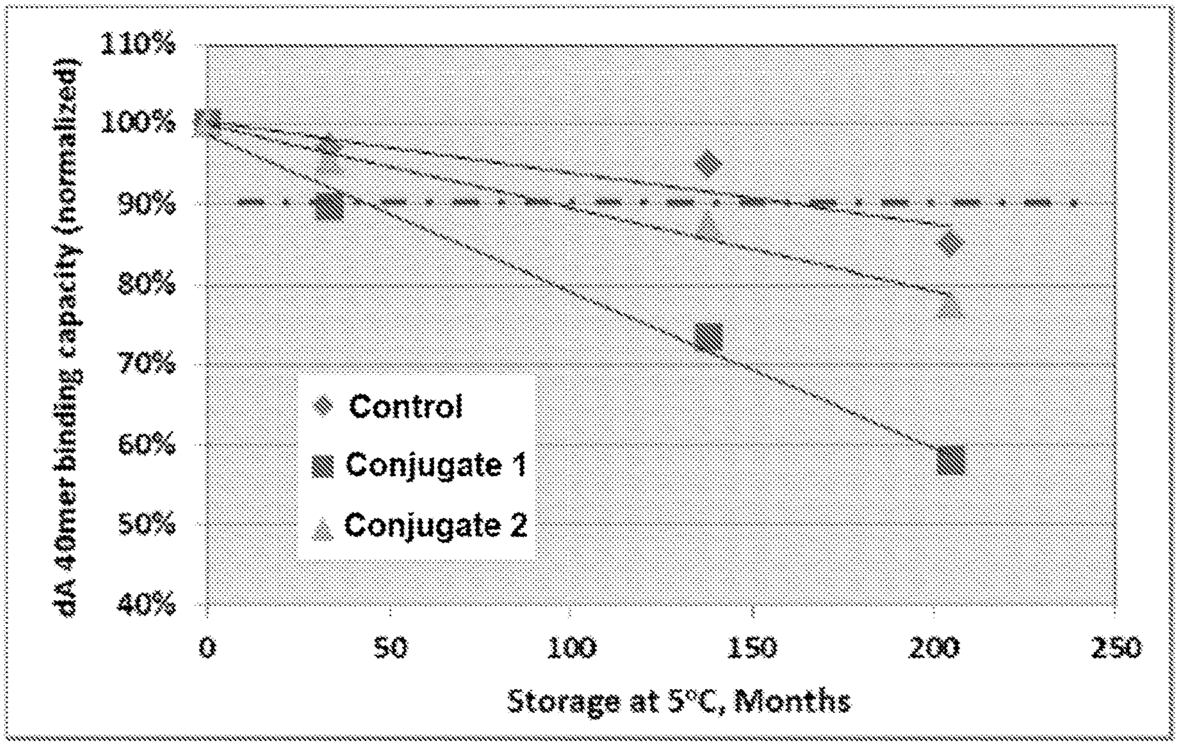
FIG. 31A and FIG. 31B illustrate the 40mer dA binding capacity of conjugate EP 150 and conjugate EP 450 samples stored at different temperatures.
Figure 31B:
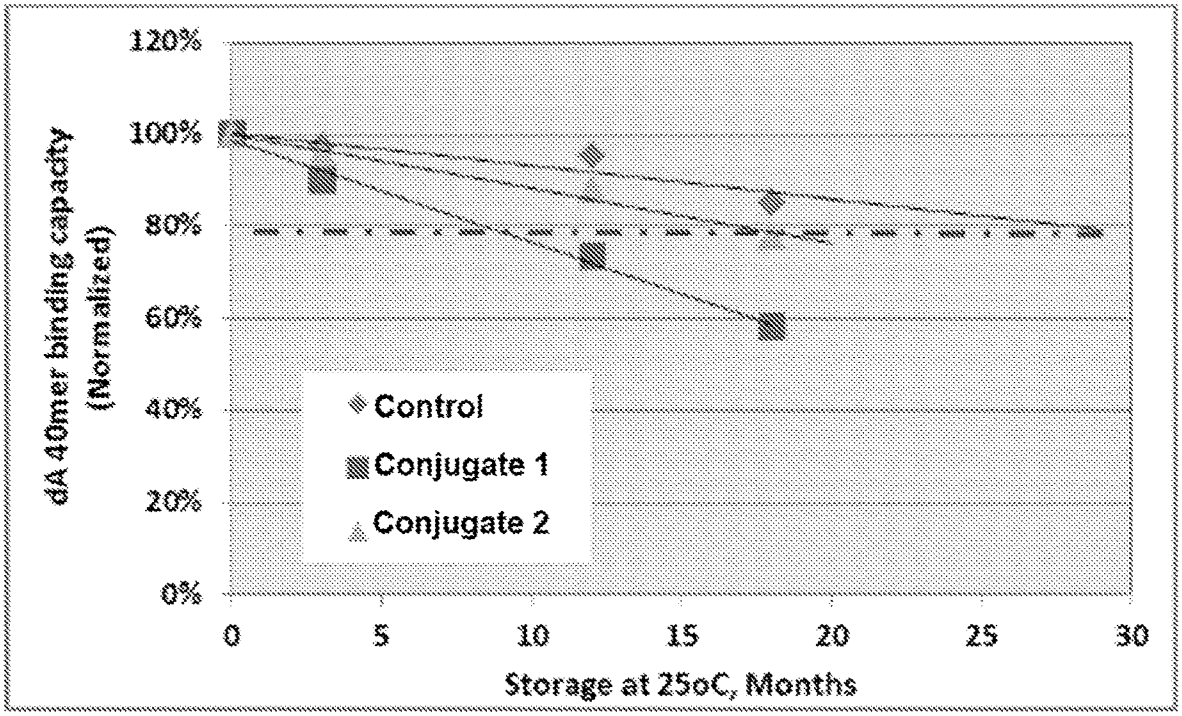

40mer dA SBC: Binding capacities were normalized based on each control sample and presented as percentage values for a better comparison. These data were plotted to predict the stability at two storage conditions, 5° C. and 25° C. (Table 18A, FIG. 31A, and FIG. 31B).

TABLE 18A

| | dA 40mer binding capacity after storage at 60° C. | | |
|---|---|---|---|
| Sample No. | 3 days | 11 days | 16 days |
| Conjugate 1 - Lot 1 | 90% | 73% | 57% |
| Conjugate 1 - Lot 2 | 89% | 74% | 59% |
| Conjugate 2 - Lot 1 | 97% | 89% | 81% |
| Conjugate 2 - Lot 2 | 94% | 86% | 74% |
| Conjugate 2 - Manufacturing batch (10 L) | 97% | 95% | 85% |

Figure 32A:
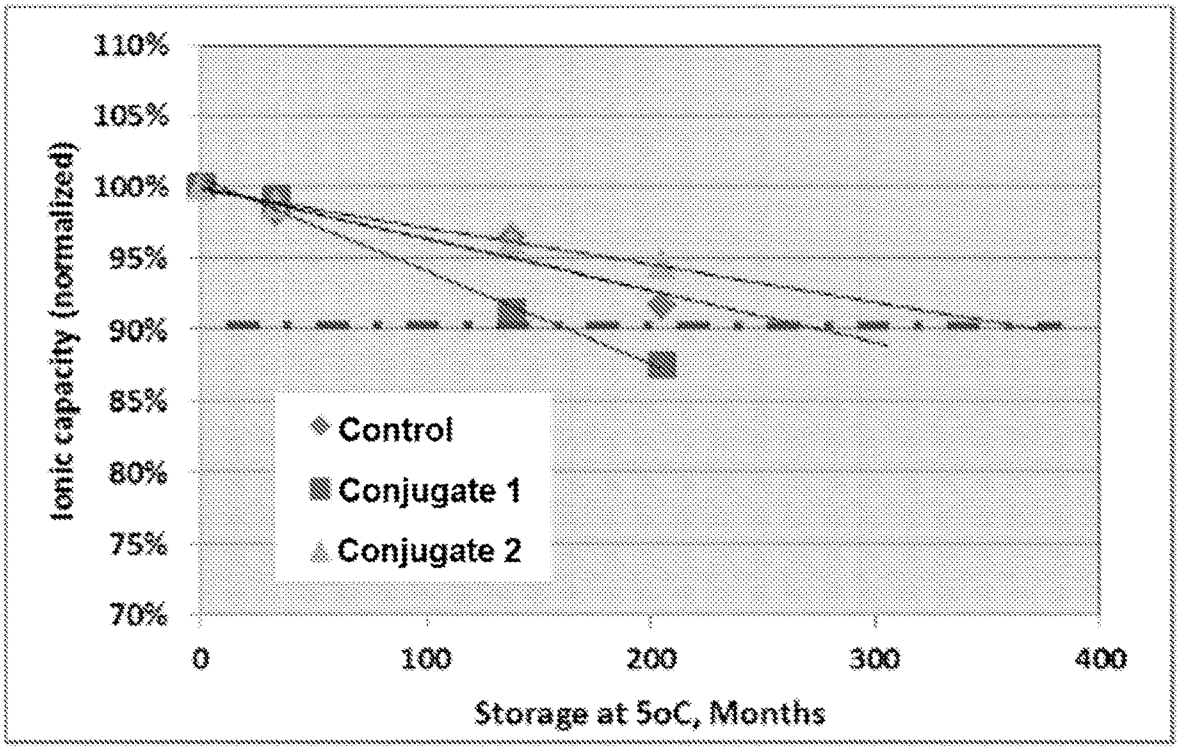
FIG. 32A and FIG. 32B illustrate the ionic capacity of conjugate EP 150 and conjugate EP 450 samples stored at different temperatures.
Figure 32B:
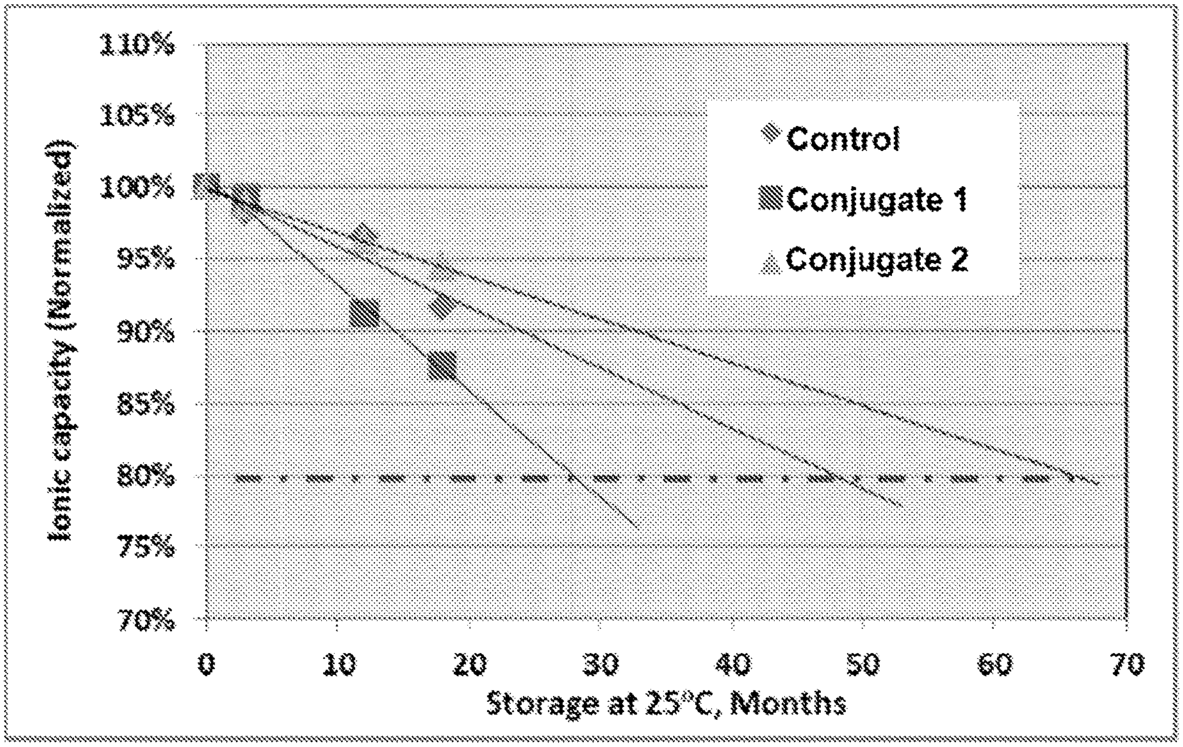

Ionic capacity: Ionic capacities were normalized based on each control sample and presented as percentage values for a better comparison. These data were plotted to predict the stability at two storage conditions, 5° C. and 25° C. (Table 18B, FIG. 32A, and FIG. 32B).

TABLE 18B

| | ionic capacity after storage at 60° C. | | |
|---|---|---|---|
| Sample No. | 3 days | 11 days | 16 days |
| Conjugate 1 - Lot 1 | 101% | 93% | 89% |
| Conjugate 1 - Lot 2 | 98% | 89% | 87% |
| Conjugate 2 - Lot 1 | 99% | 97% | 95% |
| Conjugate 2 - Lot 2 | 99% | 95% | 94% |
| Conjugate 2 - Manufacturing batch (10 L) | 98% | 97% | 92% |

Example 9—Large Pore Polystyrene Divinylbenzene Base Beads

Procedure: Polystyrene divinylbenzene base beads with pore modes of 3000 Å, 4000 Å, and 5000 Å were synthesized. Samples of each of the three polystyrene-co-divinylbenzene prototypes were coated with a hydrophilic coating (OH Polymer). Following both the standard procedure for OH-coating R150 and a modified version with a 20% reduction in mass of OH polymer charged to allow for a thinner coating on the surface. All samples were sized to remove fines <25 μm and stored as ~50% slurry in 20% ethanol/water (about 60 mL each)

Figure 33A:
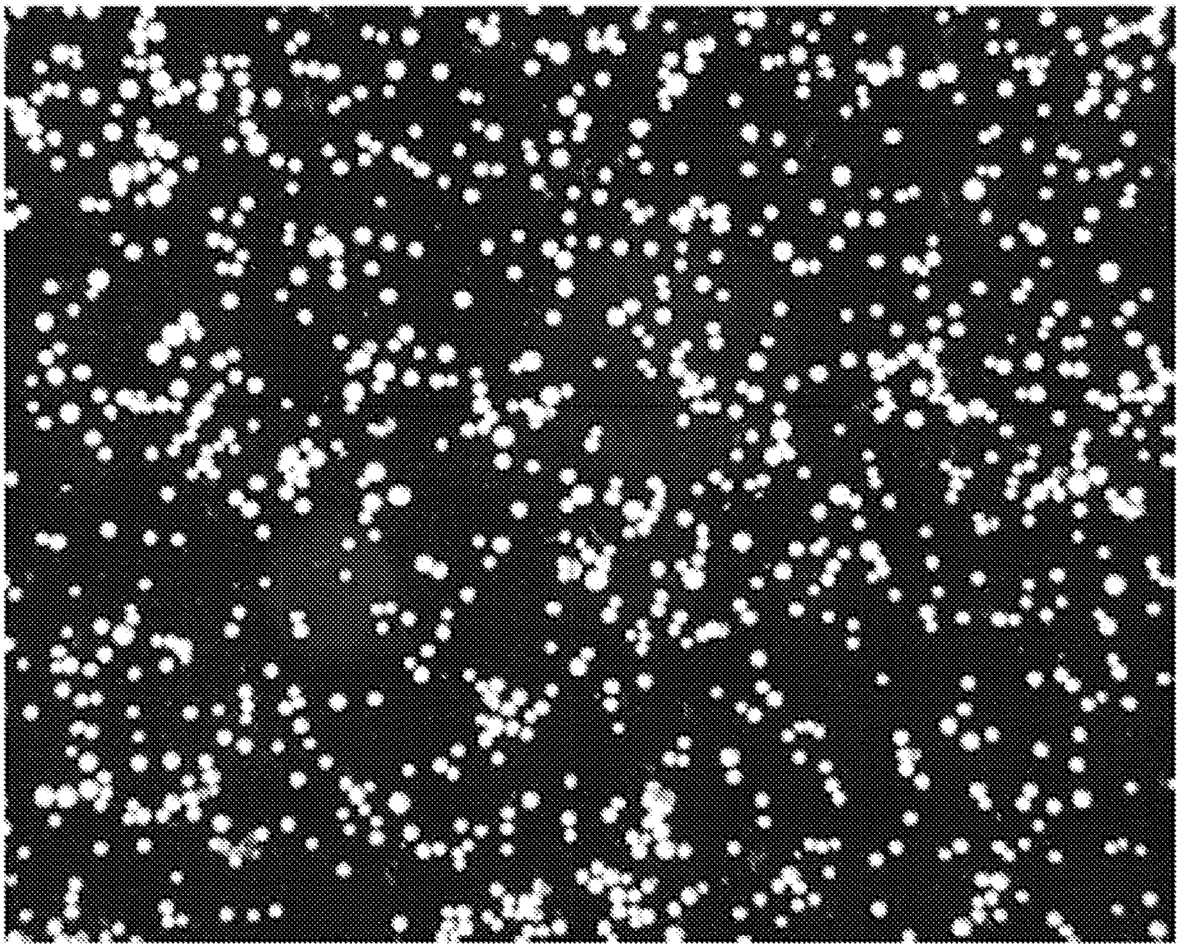
FIG. 33A, FIG. 33B, and FIG. 33C are images of the beads prepared using classical suspension polymerization of polystyrene and divinylbenzene.
Figure 33B:
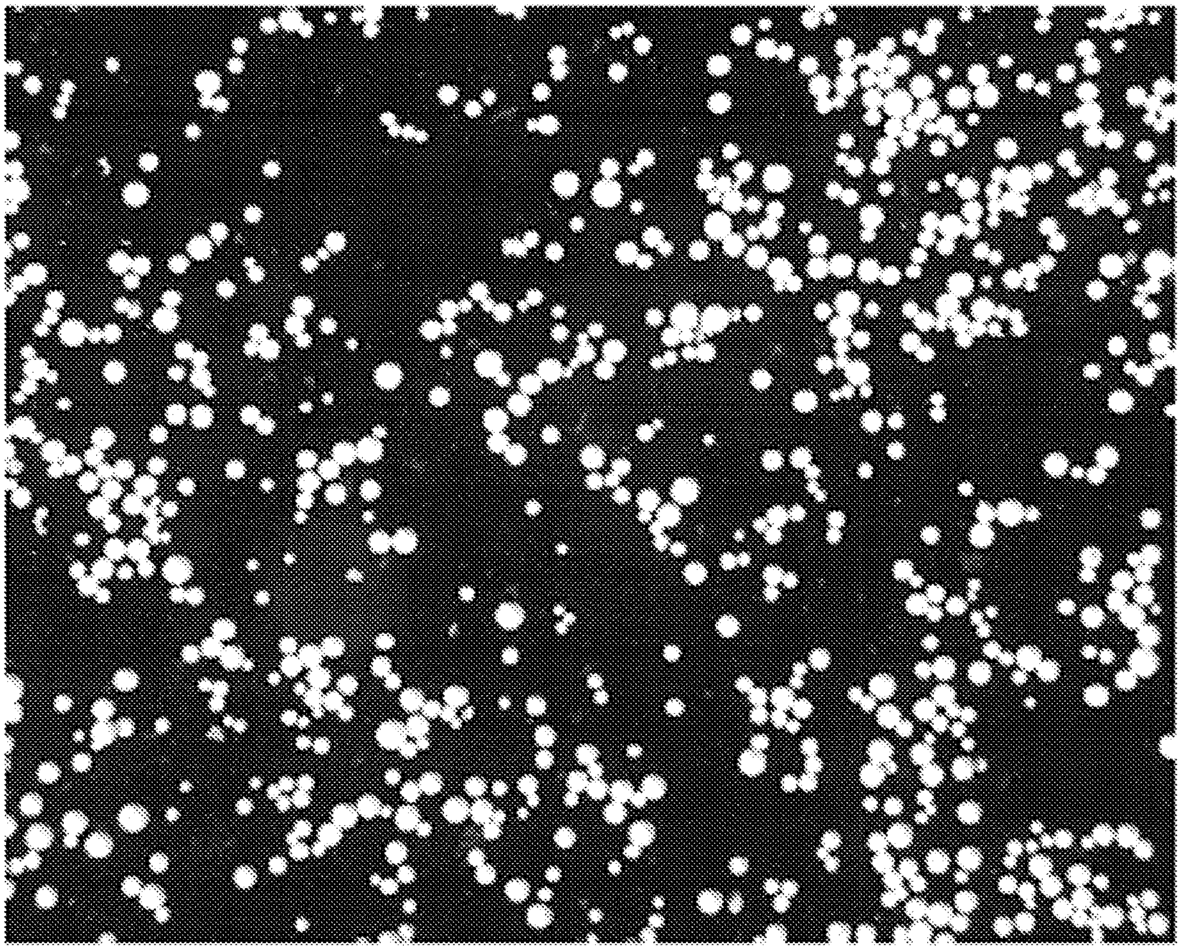
Figure 33C:
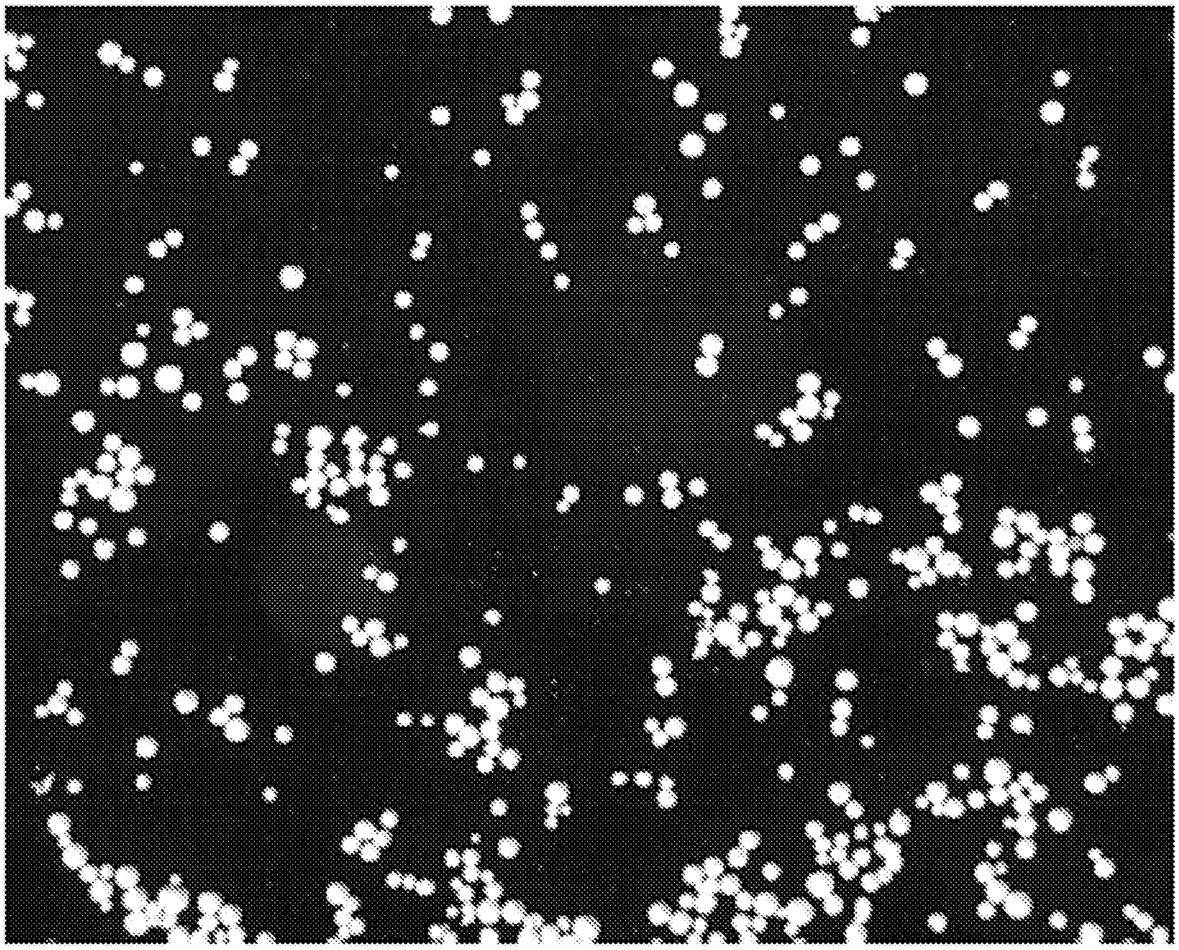

The beads (63.1% by wt porosity; 662.6% by wt cross-linker) were prepared using classical suspension polymerization of polystyrene and divinylbenzene (FIG. 33A, FIG. 33B, and FIG. 33C).

Figure 34:
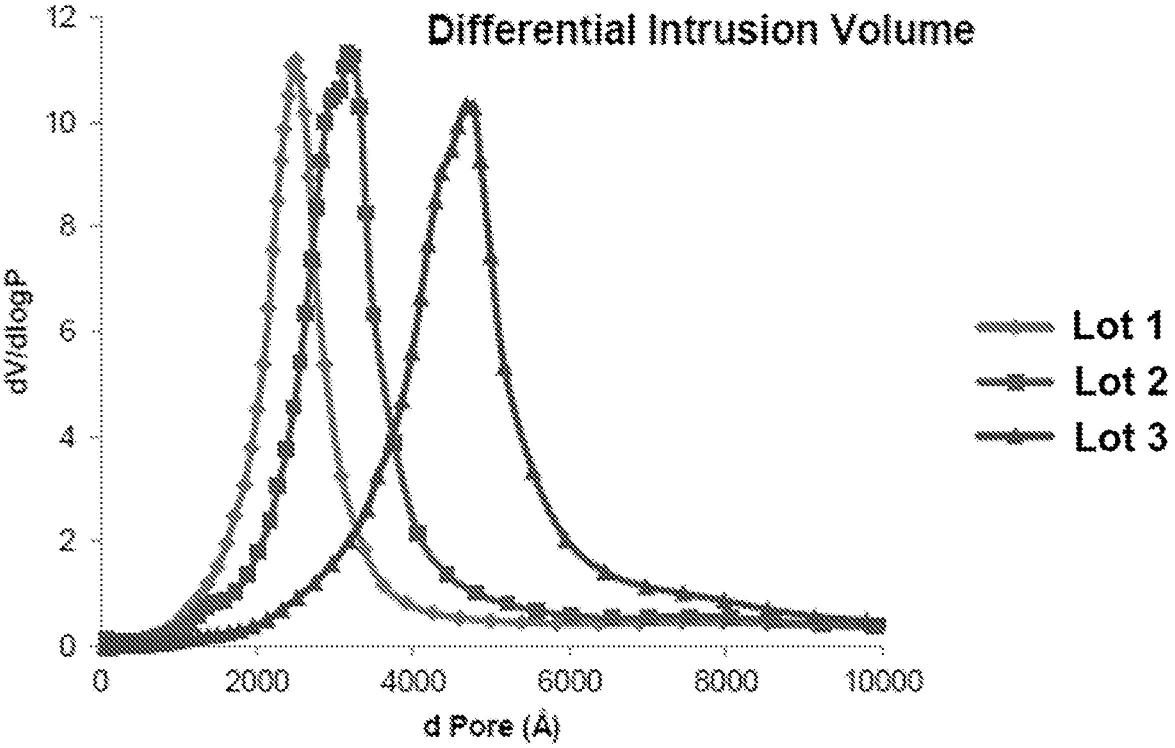
FIG. 34 illustrates the differential intrusion volume of the pore mode of Lot 1, Lot 2, and Lot 3 of the base beads synthesized in Example 9.

Results: The pore size of the base bead was measured using Prosimetery, and the results were expressed in terms of Pore Mode (Table 19 and FIG. 34). The pore size distribution widens as the pore mode is increased, and the range of pore modes is >2000 Å. The particle size of the base bead was measured via Coulter method. The mean particle size for all three samples were about 50 μm. All samples sized to remove fines <25 μm (Table 19).

TABLE 19

| Example 9 Base Bead Lot Number | Intraparticle Surface Area ($m^2$/g) | Pore Volume (mL/g) | Pore Mode (Å) | Particle Size Mean (μm) | Standard Deviation (μm) |
|---|---|---|---|---|---|
| Lot 1 | 47.8 | 2.36 | 2495 | 55.16 | 10.99 |
| Lot 2 | 45.3 | 2.46 | 3187 | 58.54 | 10.99 |
| Lot 3 | 22.2 | 2.02 | 4677 | 58.42 | 11.39 |

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims. Other embodiments are within the claims.

The invention claimed is:

1. A composition comprising a plurality of conjugates comprising the structure of Formula I:

A-L-B Formula I, wherein:

A is a surface comprising an epoxide functionalized polystyrene divinylbenzene (PSDVB) particle;

L is a linker comprising the structure:

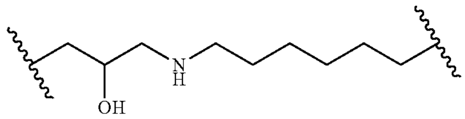

, and

B is an oligomer comprising a poly-deoxythymidine oligonucleotide consisting of 20 deoxythymidines;

and wherein the plurality of conjugates has an epoxide density of from 40 to 60 μmol/mL.

2. The composition of claim 1, wherein the plurality of conjugates has a poly-deoxythymidine oligonucleotide density of 0.1 to 0.5 μmol/mL.

3. The composition of claim 2 wherein the plurality of conjugates has a poly-deoxythymidine oligonucleotide density of about 0.3 μmol/mL.

4. The composition of claim 1, wherein the plurality of conjugates has a dT/resin charge of less than 5 mg/mL.

5. The composition of claim 4, wherein the plurality of conjugates has a dT/resin charge of about 3 mg/mL.

6. The composition of claim 1, wherein the plurality of conjugates has an ionic capacity of greater than 5 μmol/mL.

7. The composition of claim 1, wherein the plurality of conjugates has an ionic capacity of 5 to 10 μmol/mL.

8. The composition of claim 1, wherein the plurality of conjugates has a dynamic binding capacity of greater than 1.5 μmol/mL.

9. The composition of claim 1, wherein the plurality of conjugates has a mean particle size of 40 to 60 μm.

10. The composition of claim 9, wherein the plurality of conjugates has a mean particle size of about 50 μm.

11. The composition of claim 1, wherein the plurality of conjugates has a mean pore size of 1000 to 4000 Å.

12. The composition of claim 11, wherein the plurality of conjugates has a mean pore size of about 2000 Å.

13. A method of purifying a ribonucleic acid (RNA) transcript comprising a poly-adenosine tail, the method comprising:

(a) obtaining a first sample comprising the RNA transcript, wherein the first sample comprises at least 5% impurities;

(b) contacting the first sample with the composition of claim 1 under conditions such that the RNA transcript binds to a conjugate in the composition;

(c) eluting the RNA transcript from the composition; and (d) collecting the RNA transcript in a second sample, wherein the second sample comprises less than 5% impurities.

* * * * *

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1

tttttttttt tttttttttt                                        20
```